US009187738B2

(12) United States Patent
Miasnikov et al.

(10) Patent No.: US 9,187,738 B2
(45) Date of Patent: Nov. 17, 2015

(54) VARIANT LIPOLYTIC ENZYMES AND METHODS FOR EXPRESSION THEREOF

(75) Inventors: Andrei Miasnikov, Mountain View, CA (US); Richard R. Bott, Burlingame, CA (US); Jens Frisbæk Sørensen, Aarhus (DK)

(73) Assignee: DUPONT NUTRITION BIOSCIENCES APS, Copenhagen (DK)

(*) Notice: Subject to any disclaimer, the term of this patent is extended or adjusted under 35 U.S.C. 154(b) by 708 days.

(21) Appl. No.: 13/329,531

(22) Filed: Dec. 19, 2011

(65) Prior Publication Data

US 2012/0190072 A1 Jul. 26, 2012

Related U.S. Application Data

(63) Continuation-in-part of application No. PCT/IB2010/052868, filed on Jun. 23, 2010.

(60) Provisional application No. 61/220,288, filed on Jun. 25, 2009.

(51) Int. Cl.

*C12N 9/18* (2006.01)
*C12N 9/20* (2006.01)
*A21D 8/04* (2006.01)

(52) U.S. Cl.

CPC *C12N 9/20* (2013.01); *A21D 8/042* (2013.01); *C12N 9/18* (2013.01);

(Continued)

(58) Field of Classification Search

CPC ............ C12N 9/18; C12N 9/20; C12N 15/52; C12N 15/70; C12N 15/74; C12N 15/80

See application file for complete search history.

(56) References Cited

U.S. PATENT DOCUMENTS 5,658,871 A 8/1997 Batenburg et al.
6,323,322 B1 * 11/2001 Filpula et al. .............. 530/387.3

(Continued)

FOREIGN PATENT DOCUMENTS

WO WO91/00910 7/1990
WO WO 94/04035 3/1994

(Continued)

OTHER PUBLICATIONS

Caplan, S., et al., 1991, "Glycosylation and structure of the yeast MFα1 α-factor precursor is important for efficient transport through the secretory pathway", Journal of Bacteriology, vol. 173, No. 2, pp. 627-635.*

(Continued)

*Primary Examiner* — Manjunath Rao
*Assistant Examiner* — William W Moore
(74) *Attorney, Agent, or Firm* — Vedder Price P.C.; Thomas J. Kowalski; Michael B. Scher

(57) ABSTRACT

The present invention relates to a method for preparing a variant lipolytic enzyme comprising expressing in a host organism a nucleotide sequence which has at least 90% identity with a nucleotide sequence encoding a fungal lipolytic enzyme and comprises at least one modification at a position which corresponds in the encoded amino acid sequence to a) the introduction of at least one glycosylation site in the amino acid sequence compared with the original fungal lipolytic enzyme; b) the introduction of at least one amino acid at a surface position and at a location in an external loop distal to the active site of the enzyme which is more hydrophilic; or c) a substitution or insertion at one or more of positions disclosed herein or a deletion at one or more positions disclosed herein. The invention also relates to polypeptide produced by the method and to novel nucleic acids.

17 Claims, 27 Drawing Sheets

(52) U.S. Cl.
CPC .................. *C12Y 301/01003* (2013.01); *C12Y 301/01004* (2013.01); *C12Y 301/01026* (2013.01); *C12Y 301/01032* (2013.01)

(56) References Cited

U.S. PATENT DOCUMENTS

| | | | | |
|---|---|---|---|---|
| 7,368,108 | B2 * | 5/2008 | DeFrees et al. | 424/94.5 |
| 7,465,570 | B2 | 12/2008 | Borch et al. | |
| 7,629,145 | B2 * | 12/2009 | Lee et al. | 435/69.1 |
| 2008/0003619 | A1 * | 1/2008 | Lutz et al. | 435/7.4 |
| 2008/0026376 | A1 * | 1/2008 | Wang et al. | 435/6 |
| 2008/0038404 | A1 * | 2/2008 | Brunstedt et al. | 426/32 |
| 2009/0275083 | A1 * | 11/2009 | De Maria et al. | 435/69.2 |
| 2011/0027830 | A1 * | 2/2011 | Cervin et al. | 435/69.7 |
| 2011/0286916 | A1 * | 11/2011 | Aste-Amezaga et al. | 424/1.49 |

FOREIGN PATENT DOCUMENTS

| | | |
|---|---|---|
| WO | WO98/26057 | 6/1998 |
| WO | WO 02/00852 | 1/2002 |
| WO | WO 2004/099400 | 11/2004 |
| WO | WO 2005/087918 | 9/2005 |
| WO | WO 2007/087243 | 8/2007 |
| WO | WO 2009/106575 | 9/2009 |
| WO | WO 2009/107091 | 9/2009 |

OTHER PUBLICATIONS

Nagao, T. et al., 1994, “Cloning and nucleotide sequence of cDNA encoding a lipase from Fusarium heterosporum”, Journal of Biochemistry, vol. 116, No. 3, pp. 536-540.*

Sagt et al., Introduction of an N-glycosylation site increases secretion of heterologous proteins in yeasts, Appl Environ Microbiol. Nov. 2000;66(11):4940-4.

Toshihiro Nagao, et al., C-Terminal Peptide of Fusarium Heterosporum Lipase is Necessary for its Increasing Thermostability, J. Biochem. (1998) vol. 124, p. 1124-1129.

Abstract: 2nd European Symposium on Enzymes in Grain Processing ESEPG-2, Helsinki, Finland, Dec. 8-10, 1999: J. Qi Si, et al., Effects of Enzymes in Pasta and Noodle Production, p. 161-169.

Shu Zheng-Yu et al., Development of Novel Microbial Lipase Resources, Microbiology China, vol. 36 (5), p. 747-752 (May 20, 2009), English abstract and Figure legends only.

Shu Zheng-Yu et al., Development of Novel Microbial Lipase Resources, Microbiology China, vol. 36 (5), p. 747-752 (May 20, 2009) (English Translation), of only three paragraphs.

Shu Zhen-Yu, Doctoral Dissertation, Biochemical Characterization, Gene Cloning and Expression and Structure Prediction of Lipase from Aspergillus niger, 2007 (reference 48 in Shu 2009), English introduction only.

* cited by examiner

FIGURE 1

SEQ ID No. 1.
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAAGATCACCTGTTCC
AACAATGGTTGCCCAACGATTGAGTCCAACGGCGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTGCTGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGACGTTAT
AGGAGCGCCAAGCGTGAGAGCATCGACATGAGGGCTACCATGACAGACGCACAGTTGGAGGCCAAGCTCAAC
TCTTATGTTGCCATGGATCAGGAGTATGTCAAGACTCACCAAAACCGCACATGAGGCGCGCC

FIGURE 2

SEQ ID No: 2
MLLLSLLSAVTLAVASPVALEEYANSLEDRAVGVTSTDFTNFKFYIQHGAAAYCNSGTAAGAKITCSNNGCP
TIESNGVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRAAGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRRYRSAKRESIDMRATMTDAQLEAKLNSYVAMDQEYVKTHQNRT

FIGURE 3A

SEQ ID No: 3

AAGCTTAACTAGTACTTCTCGAGCTCTGTACATGTCCGGTCGCGACGTACGCGTATCGATGGCGCCAGCTGC
AGGCGGCCGCCTGCAGCCACTTGCAGTCCCGTGGAATTCTCACGGTGAATGTAGGCCTTTTGTAGGGTAGGA
ATTGTCACTCAAGCACCCCCAACCTCCATTACGCCTCCCCCATAGAGTTCCCAATCAGTGAGTCATGGCACT
GTTCTCAAATAGATTGGGGAGAAGTTGACTTCCGCCCAGAGCTGAAGGTCGCACAACCGCATGATATAGGGT
CGGCAACGGCAAAAAAGCACGTGGCTCACCGAAAAGCAAGATGTTTGCGATCTAACATCCAGGAACCTGGAT
ACATCCATCATCACGCACGACCACTTTGATCTGCTGGTAAACTCGTATTCGCCCTAAACCGAAGTGCGTGGT
AAATCTACACGTGGGCCCCTTTCGGTATACTGCGTGTGTCTTCTCTAGGTGCCATTCTTTTCCCTTCCTCTA
GTGTTGAATTGTTTGTGTTGGAGTCCGAGCTGTAACTACCTCTGAATCTCTGGAGAATGGTGGACTAACGAC
TACCGTGCACCTGCATCATGTATATAATAGTGATCCTGAGAAGGGGGGTTTGGAGCAATGTGGGACTTTGAT
GGTCATCAAACAAAGAACGAAGACGCCTCTTTTGCAAAGTTTTGTTTCGGCTACGGTGAAGAACTGGATACT
TGTTGTGTCTTCTGTGTATTTTTGTGGCAACAAGAGGCCAGAGACAATCTATTCAAACACCAAGCTTGCTCT
TTTGAGCTACAAGAACCTGTGGGGTATATATCTAGAGTTGTGAAGTCGGTAATCCCGCTGTATAGTAATACG
AGTCGCATCTAAATACTCCGAAGCTGCTGCGAACCCGGAGAATCGAGATGTGCTGGAAAGCTTCTAGCGAGC
GGCTAAATTAGCATGAAAGGCTATGAGAAATTCTGGAGACGGCTTGTTGAATCATGGCGTTCCATTCTTCGA
CAAGCAAAGCGTTCCGTCGCAGTAGCAGGCACTCATTCCCGAAAAAACTCGGAGATTCCTAAGTAGCGATGG
AACCGGAATAATATAATAGGCAATACATTGAGTTGCCTCGACGGTTGCAATGCAGGGGTACTGAGCTTGGAC
ATAACTGTTCCGTACCCCACCTCTTCTCAACCTTTGGCGTTTCCCTGATTCAGCGTACCCGTACAAGTCGTA
ATCACTATTAACCCAGACTGACCGGACGTGTTTTGCCCTTCATTTGGAGAAATAATGTCATTGCGATGTGTA
ATTTGCCTGCTTGACCGACTGGGGCTGTTCGAAGCCCGAATGTAGGATTGTTATCCGAACTCTGCTCGTAGA
GGCATGTTGTGAATCTGTGTCGGGCAGGACACGCCTCGAAGGTTCACGGCAAGGGAAACCACCGATAGCAGT
GTCTAGTAGCAACCTGTAAAGCCGCAATGCAGCATCACTGGAAAATACAAACCAATGGCTAAAAGTACATAA
GTTAATGCCTAAAGAAGTCATATACCAGCGGCTAATAATTGTACAATCAAGTGGCTAAACGTACCGTAATTT
GCCAACGGCTTGTGGGGTTGCAGAAGCAACGGCAAAGCCCCACTTCCCCACGTTTGTTTCTTCACTCAGTCC
AATCTCAGCTGGTGATCCCCCAATTGGGTCGCTTGTTTGTTCCGGTGAAGTGAAAGAAGACAGAGGTAAGAA
TGTCTGACTCGGAGCGTTTTGCATACAACCAAGGGCAGTGATGGAAGACAGTGAAATGTTGACATTCAAGGA
GTATTTAGCCAGGGATGCTTGAGTGTATCGTGTAAGGAGGTTTGTCTGCCGATACGACGAATACTGTATAGT
CACTTCTGATGAAGTGGTCCATATTGAAATGTAAGTCGGCACTGAACAGGCAAAAGATTGAGTTGAAACTGC
CTAAGATCTCGGGCCCTCGGGCCTTCGGCCTTTGGGTGTACATGTTTGTGCTCCGGGCAAATGCAAAGTGTG
GTAGGATCGAACACACTGCTGCCTTTACCAAGCAGCTGAGGGTATGTGATAGGCAAATGTTCAGGGGCCACT
GCATGGTTTCGAATAGAAAGAGAAGCTTAGCCAAGAACAATAGCCGATAAAGATAGCCTCATTAAACGGAAT
GAGCTAGTAGGCAAAGTCAGCGAATGTGTATATATAAAGGTTCGAGGTCCGTGCCTCCCTCATGCTCTCCCC
ATCTACTCATCAACTCAGATCCTCCAGGAGACTTGTACACCATCTTTTGAGGCACAGAAACCCAATAGTCAA
CCGCGGACTGCGCATCATGTATCGGAAGTTGGCCGTCATCTCGGCCTTCTTGGCCACACCTCGTGCTAGACT
AGGCGCGCCGCGCGCCAGCTCCGTGCGAAAGCCTGACGCACCGGTAGATTCTTGGTGAGCCCGTATCATGAC
GGCGGCGGGAGCTACATGGCCCCGGGTGATTTATTTTTTTTGTATCTACTTCTGACCCTTTTCAAATATACG
GTCAACTCATCTTTCACTGGAGATGCGGCCTGCTTGGTATTGCGATGTTGTCAGCTTGGCAAATTGTGGCTT
TCGAAAACACAAAACGATTCCTTAGTAGCCATGCATTTTAAGATAACGGAATAGAAGAAAGAGGAAATTAAA
AAAAAAAAAAAAACAAACATCCCGTTCATAACCCGTAGAATCGCCGCTCTTCGTGTATCCCAGTACCAGTTT
ATTTTGAATAGCTCGCCCGCTGGAGAGCATCCTGAATGCAAGTAACAACCGTAGAGGCTGACACGGCAGGTG
TTGCTAGGGAGCGTCGTGTTCTACAAGGCCAGACGTCTTCGCGGTTGATATATATGTATGTTTGACTGCAGG
CTGCTCAGCGACGACAGTCAAGTTCGCCCTCGCTGCTTGTGCAATAATCGCAGTGGGAAGCCACACCGTGA
CTCCCATCTTTCAGTAAAGCTCTGTTGGTGTTTATCAGCAATACACGTAATTTAAACTCGTTAGCATGGGGC
TGATAGCTTAATTACCGTTTACCAGTGCCATGGTTCTGCAGCTTTCCTTGGCCCGTAAAATTCGGCGAAGCC
AGCCAATCACCAGCTAGGCACCAGCTAAACCCTATAATTAGTCTCTTATCAACACCATCCGCTCCCCCGGGA
TCAATGAGGAGAATGAGGGGGATGCGGGGCTAAAGAAGCCTACATAACCCTCATGCCAACTCCCAGTTTACA
CTCGTCGAGCCAACATCCTGACTATAAGCTAACACAGAATGCCTCAATCCTGGGAAGAACTGGCCGCTGATA
AGCGCGCCCGCCTCGCAAAAACCATCCCTGATGAATGGAAAGTCCAGACGCTGCCTGCGGAAGACAGCGTTA
TTGATTTCCCAAAGAAATCGGGGATCCTTTCAGAGGCCGAACTGAAGATCACAGAGGCCTCCGCTGCAGATC
TTGTGTCCAAGC

FIGURE 3B

SEQ ID No: 3

TGGCGGCCGGAGAGTTGACCTCGGTGGAAGTTACGCTAGCATTCTGTAAACGGGCAGCAATCGCCCAGCAGT
TAGTAGGGTCCCCTCTACCTCTCAGGGAGATGTAACAACGCCACCTTATGGGACTATCAAGCTGACGCTGGC
TTCTGTGCAGACAAACTGCGCCCACGAGTTCTTCCCTGACGCCGCTCTCGCGCAGGCAAGGGAACTCGATGA
ATACTACGCAAAGCACAAGAGACCCGTTGGTCCACTCCATGGCCTCCCCATCTCTCTCAAAGACCAGCTTCG
AGTCAAGGTACACCGTTGCCCCTAAGTCGTTAGATGTCCCTTTTTGTCAGCTAACATATGCCACCAGGGCTA
CGAAACATCAATGGGCTACATCTCATGGCTAAACAAGTACGACGAAGGGGACTCGGTTCTGACAACCATGCT
CCGCAAAGCCGGTGCCGTCTTCTACGTCAAGACCTCTGTCCCGCAGACCCTGATGGTCTGCGAGACAGTCAA
CAACATCATCGGGCGCACCGTCAACCCACGCAACAAGAACTGGTCGTGCGGCGGCAGTTCTGGTGGTGAGGG
TGCGATCGTTGGGATTCGTGGTGGCGTCATCGGTGTAGGAACGGATATCGGTGGCTCGATTCGAGTGCCGGC
CGCGTTCAACTTCCTGTACGGTCTAAGGCCGAGTCATGGGCGGCTGCCGTATGCAAAGATGGCGAACAGCAT
GGAGGGTCAGGAGACGGTGCACAGCGTTGTCGGGCCGATTACGCACTCTGTTGAGGGTGAGTCCTTCGCCTC
TTCCTTCTTTTCCTGCTCTATACCAGGCCTCCACTGTCCTCCTTTCTTGCTTTTTATACTATATACGAGACC
GGCAGTCACTGATGAAGTATGTTAGACCTCCGCCTCTTCACCAAATCCGTCCTCGGTCAGGAGCCATGGAAA
TACGACTCCAAGGTCATCCCCATGCCCTGGCGCCAGTCCGAGTCGGACATTATTGCCTCCAAGATCAAGAAC
GGCGGGCTCAATATCGGCTACTACAACTTCGACGGCAATGTCCTTCCACACCCTCCTATCCTGCGCGGCGTG
GAAACCACCGTCGCCGCACTCGCCAAAGCCGGTCACACCGTGACCCCGTGGACGCCATACAAGCACGATTTC
GGCCACGATCTCATCTCCCATATCTACGCGGCTGACGGCAGCGCCGACGTAATGCGCGATATCAGTGCATCC
GGCGAGCCGGCGATTCCAAATATCAAAGACCTACTGAACCCGAACATCAAAGCTGTTAACATGAACGAGCTC
TGGGACACGCATCTCCAGAAGTGGAATTACCAGATGGAGTACCTTGAGAAATGGCGGGAGGCTGAAGAAAAG
GCCGGGAAGGAACTGGACGCCATCATCGCGCCGATTACGCCTACCGCTGCGGTACGGCATGACCAGTTCCGG
TACTATGGGTATGCCTCTGTGATCAACCTGCTGGATTTCACGAGCGTGGTTGTTCCGGTTACCTTTGCGGAT
AAGAACATCGATAAGAAGAATGAGAGTTTCAAGGCGGTTAGTGAGCTTGATGCCCTCGTGCAGGAAGAGTAT
GATCCGGAGGCGTACCATGGGGCACCGGTTGCAGTGCAGGTTATCGGACGGAGACTCAGTGAAGAGAGGACG
TTGGCGATTGCAGAGGAAGTGGGGAAGTTGCTGGGAAATGTGGTGACTCCATAGCTAATAAGTGTCAGATAG
CAATTTGCACAAGAAATCAATACCAGCAACTGTAAATAAGCGCTGAAGTGACCATGCCATGCTACGAAAGAG
CAGAAAAAAACCTGCCGTAGAACCGAAGAGATATGACACGCTTCCATCTCTCAAAGGAAGAATCCCTTCAGG
GTTGCGTTTCCAGTCTAGACACGTATAACGGCACAAGTGTCTCTCACCAAATGGGTTATATCTCAAATGTGA
TCTAAGGATGGAAAGCCCAGAATATCGATCGCGCGCAGATCCATATATAGGGCCCGGGTTATAATTACCTCA
GGTCGACGTCCCATGGCCATTCGAATTCGTAATCATGGTCATAGCTGTTTCCTGTGTGAAATTGTTATCCGC
TCACAATTCCACACAACATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTTG
GTAGCTCTTGATCCGGCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAGTTACCAATGCTTAATCAGTGAGGCAC
CTATCTCAGCGATCTGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCACCGGCTCCAGATTTAT
CAGCAATAAACCAGCC

FIGURE 3C

SEQ ID No: 3

AGCCGGAAGGGCCGAGCGCAGAAGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTGCCATTGCTACAGGCATCGTGGT
GTCACGCTCGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAACGTTCTTCGGGGCGAAA
ACTCTCAAGGATCTTACCGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCCGCAAAAAAGGGAATAAG
GGCGACACGGAAATGTTGAATACTCATACTCTTCCTTTTTCAATATTATTGAAGCATTTATCAGGGTTATTG
TCTCATGAGCGGATACATATTTGAATGTATTTAGAAAAATAAACAAATAGGGGTTCCGCGCACATTTCCCCG
AAAAGTGCCACCTGACGTCTAAGAAACCATTATTATCATGACATTAACCTATAAAAATAGGCGTATCACGAG
GCCCTTTCGTCTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTTGGCGGGTGTCG
GGGCTGGCTTAACTATGCGGCATCAGAGCAGATTGTACTGAGAGTGCACCATAAAATTGTAAACGTTAATAT
TTTGTTAAAATTCGCGTTAAATTTTTGTTAAATCAGCTCATTTTTTAACCAATAGGCCGAAATCGGCAAAAT
CCCTTATAAATCAAAAGAATAGCCCGAGATAGGGTTGAGTGTTGTTCCAGTTTGGAACAAGAGTCCACTATT
AAAGAACGTGGACTCCAACGTCAAAGGGCGAAAAACCGTCTATCAGGGCGATGGCCCACTACGTGAACCATC
ACCCAAATCAAGTTTTTTGGGGTCGAGGTGCCGTAAAGCACTAAATCGGAACCCTAAAGGGAGCCCCCGATT
TAGAGCTTGACGGGGAAAGCCGGCGAACGTGGCGAGAAAGGAAGGGAAGAAAGCGAAAGGAGCGGGCGCTAG
GGCGCTGGCAAGTGTAGCGGTCACGCTGCGCGTAACCACCACACCCGCCGCGCTTAATGCGCCGCTACAGGG
CGCGTACTATGGTTGCTTTGACGTATGCGGTGTGAAATACCGCACAGATGCGTAAGGAGAAAATACCGCATC
AGGCGCCATTCGCCATTCAGGCTGCGCAACTGTTGGGAAGGGCGATCGGTGCGGGCCTCTTCGCTATTACGC
CAGCTGGCGAAAGGGGGATGTGCTGCAAGGCGATTAAGTTGGGTAACGCCAGGGTTTTCCCAGTCACGACGT
TGTAAAACGACGGCCAGTGC

FIGURE 4

SEQ ID No: 4
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACGGCGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTGCTGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGATCTTAT
AGGAGCGCCAAGCGTGAGAGCATCGACATGAGGGCTACCATGACAGACGCACAGTTGGAGGCCAAGCTCAAC
TCTTATGTTGCCATGGATCAGGAGTATGTCAAGACTCACCAAAACCGCACATGAGGCGCGCC

FIGURE 5

SEQ ID No: 5
MLLLSLLSAVTLAVASPVALEEYANSLEDRAVGVTSTDFTNFKFYIQHGAAAYCNSGTAAGANITCSNNGCP
TIESNGVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRAAGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAKRESIDMRATMTDAQLEAKLNSYVAMDQEYVKTHQNRT

FIGURE 6

SEQ ID No: 6
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAAGATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTGCTGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGATCTTAT
AGGAGCGCCAAGCGTGAGAGCATCGACATGAGGGCTACCATGACAGACGCACAGTTGGAGGCCAAGCTCAAC
TCTTATGTTGCCATGGATCAGGAGTATGTCAAGACTCACCAAAACCGCACATGAGGCGCGCC

FIGURE 7

SEQ ID No: 7
MLLLSLLSAVTLAVASPVALEEYANSLEDRAVGVTSTDFTNFKFYIQHGAAAYCNSGTAAGAKITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRAAGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAKRESIDMRATMTDAQLEAKLNSYVAMDQEYVKTHQNRT

FIGURE 8

SEQ ID No: 8
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAAGATCACCTGTTCC
AACAATGGTTGCCCAACGATTGAGTCCAACGGCGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTAACGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGATCTTAT
AGGAGCGCCAAGCGTGAGAGCATCGACATGAGGGCTACCATGACAGACGCACAGTTGGAGGCCAAGCTCAAC
TCTTATGTTGCCATGGATCAGGAGTATGTCAAGACTCACCAAAACCGCACATGAGGCGCGCC

FIGURE 9

SEQ ID No: 9
MLLLSLLSAVTLAVASPVALEEYANSLEDRAVGVTSTDFTNFKFYIQHGAAAYCNSGTAAGAKITCSNNGCP
TIESNGVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAKRESIDMRATMTDAQLEAKLNSYVAMDQEYVKTHQNRT

FIGURE 10A

SEQ ID No: 10
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCG

FIGURE 10B

SEQ ID No: 10
GCGCTGTGGCCACACTGAGTGCTGCAAACCTTCGAGCTAACGGTACACCCGTCGACATCTACACATATGGTG
CTCCTCGAGTAGGAAACGCCGCGCTCTCTGCTTTCATCTCGAACCAGGCTGGCGGAGAATTTCGCGTTACGC
ACGACAAGGATCCCGTGCCTCGTCTTCCCCCTCTGATCTTCGGATACCGACACACAACCCCAGAGTACTGGC
TGTCTGGCGGCGGCGGCGACAAGGTTGACTACGCCATCAGCGACGTCAAGGTCTGTGAGGGTGCTGCCAATC
TCATGTGCAACGGTGGAACTCTGGGTCTGGATATTGATGCTCATCTGCACTACTTCCAGGCGACTGATGCTT
GCAACGCTGGTGGCTTCTCTTGGAGATCTTATAGGAGCGCCAAGCGTGAGAGCATCGACATGAGGGCTACCA
TGACAGACGCACAGTTGGAGGCCAAGCTCAACTCTTATGTTGCCATGGATCAGGAGTATGTCAAGACTCACC
AAAACCGCACATGAGGCGCGCC

FIGURE 11

SEQ ID No: 11
MLLLSLLSAVTLAVASPVALEEYANSLEDRAVGVTSTDFTNFKFYIQHGAAAYCNSGTAAGANITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAKRESIDMRATMTDAQLEAKLNSYVAMDQEYVKTHQNRT

FIGURE 12

SEQ ID No: 12
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTAACGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGATCTTAT
AGGAGCGCTGAGAGCATCGACATGAGGGCTACCATGACAGACGCACAGTTGGAGGCCAAGCTCAACTCTTAT
GTTGCCATGGATCAGGAGTATGTCAAGACTCACCAAAACCGCACATGAGGCGCGCCG

FIGURE 13

SEQ ID No: 13
MLLLSLLSAVTLAVASPVALEEYANSLEDRAVGVTSTDFTNFKFYIQHGAAAYCNSGTAAGANITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAESIDMRATMTDAQLEAKLNSYVAMDQEYVKTHQNRT

FIGURE 14

SEQ ID No: 14
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAAGATCACCTGTTCC
AACAATGGTTGCCCAACGATTGAGTCCAACGGCGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTGCTGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAGATCTTAT
AGGAGCGCTGAGAGCATCGACATGAGGGCTACCATGACAGACGCACAGTTGGAGGCCAAGCTCAACTCTTAT
GTTGCCATGGATCAGGAGTATGTCAAGACTCACCAAAACCGCACATGAGGCGCGCC

FIGURE 15

SEQ ID No: 15
MLLLSLLSAVTLAVASPVALEEYANSLEDRAVGVTSTDFTNFKFYIQHGAAAYCNSGTAAGAKITCSNNGCP
TIESNGVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRAAGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRRYRSAKRESIDMRATMTDAQLEAKLNSYVAMDQEYVKTHQNRT

FIGURE 16

SEQ ID No: 16
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTAACGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGCGCTCCACC
ATGACAGACGCACAGTTGGAGGCCAAGCTCAACTCTTATGTTGCCATGGATCAGGAGTATGTCAAGACTCAC
CAAAACCGCACATGAGGCGCGCC

FIGURE 17

SEQ ID No: 17
MLLLSLLSAVTLAVASPVALEEYANSLEDRAVGVTSTDFTNFKFYIQHGAAAYCNSGTAAGANITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSTMTDAQLEAKLNSYVAMDQEYVKTHQNRT

FIGURE 18

SEQ ID No: 18
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTAACGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGCGCTCCGAG
ATGACAGACGCACAGTTGGAGGCCAAGCTCAACTCTTATGTTGCCATGGATCAGGAGTATGTCAAGACTCAC
CAAAACCGCACATGAGGCGCGCC

FIGURE 19

SEQ ID No: 19
MLLLSLLSAVTLAVASPVALEEYANSLEDRAVGVTSTDFTNFKFYIQHGAAAYCNSGTAAGANITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSEMTDAQLEAKLNSYVAMDQEYVKTHQNRT

FIGURE 20

SEQ ID No: 20
CCGCGGACTGGCATCATGCTTCTTCTATCCCTCCTCTCGGCTGTCACCCTTGCGGTGGCCAGTCCTGTAGCC
CTCGAAGAATACGCCAACTCTCTTGAAGACAGAGCCGTTGGAGTCACCTCAACAGACTTCACCAACTTCAAG
TTCTACATCCAGCATGGCGCCGCAGCATACTGCAACTCCGGGACCGCAGCCGGTGCAAACATCACCTGTTCC
AACAATGGTTGCCCAACGATTGAGTCCAACAACGTGACTGTCGTGGCATCTTTCACTGGCTCCAAGACTGGC
ATCGGCGGGTACGTCTCGACAGATAGCTCCCGTAAAGAAATCGTCGTCGCGATCCGTGGTAGCAGCAACATC
CGCAACTGGCTTACAAACCTCGACTTTGACCAGTCCGACTGCAGTCTTGTCTCTGGCTGTGGTGTGCACTCT
GGCTTCCAGAACGCCTGGGCCGAGATCTCGGCGCAAGCAAGCGCTGCTGTAGCAAAAGCTCGCAAGGCGAAC
CCTTCCTTCAAGGTCGTCGCCACAGGCCACTCCCTCGGCGGCGCTGTGGCCACACTGAGTGCTGCAAACCTT
CGAGCTAACGGTACACCCGTCGACATCTACACATATGGTGCTCCTCGAGTAGGAAACGCCGCGCTCTCTGCT
TTCATCTCGAACCAGGCTGGCGGAGAATTTCGCGTTACGCACGACAAGGATCCCGTGCCTCGTCTTCCCCCT
CTGATCTTCGGATACCGACACACAACCCCAGAGTACTGGCTGTCTGGCGGCGGCGGCGACAAGGTTGACTAC
GCCATCAGCGACGTCAAGGTCTGTGAGGGTGCTGCCAATCTCATGTGCAACGGTGGAACTCTGGGTCTGGAT
ATTGATGCTCATCTGCACTACTTCCAGGCGACTGATGCTTGCAACGCTGGTGGCTTCTCTTGGAACTCCACC
ATGACAGACGCACAGTTGGAGGCCAAGCTCAACTCTTATGTTGCCATGGATCAGGAGTATGTCAAGACTCAC
CAAAACCGCACATGAGGCGCGCC

FIGURE 21

SEQ ID No: 21
MLLLSLLSAVTLAVASPVALEEYANSLEDRAVGVTSTDFTNFKFYIQHGAAAYCNSGTAAGANITCSNNGCP
TIESNNVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRANGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWNSTMTDAQLEAKLNSYVAMDQEYVKTHQNR

FIGURE 22

```
               1                                                                           60
   KLM1wt   (1) MLLLSLLSAVTLAVASPVALEEYANSLEDRAVGVTSTDFTNFKFYIQHGAAAYCNSGTAAGAKITCSNNGCPTIESNGVT
    MUT 1   (1) MLLLSLLSAVTLAVASPVALEEYANSLEDRAVNVTSTDFTNFKFYIQHGAAAYCNSGTAAGAKITCSNNGCPTIESNGVT
    MUT 3   (1) MLLLSLLSAVTLAVASPVALEEYANSLEDRAVGVTSTDFTNFKFYIQHGAAAYCNSGTAAGANITCSNNGCPTIESNGVT
    MUT 4   (1) MLLLSLLSAVTLAVASPVALEEYANSLEDRAVGVTSTDFTNFKFYIQHGAAAYCNSGTAAGAKITCSNNGCPTIESNNVT
    MUT 5   (1) MLLLSLLSAVTLAVASPVALEEYANSLEDRAVGVTSTDFTNFKFYIQHGAAAYCNSGTAAGAKITCSNNGCPTIESNGVT
    MUT 9   (1) MLLLSLLSAVTLAVASPVALEEYANSLEDRAVGVTSTDFTNFKFYIQHGAAAYCNSGTAAGAKITCSNNGCPTIESNGVT
  MUT 345   (1) MLLLSLLSAVTLAVASPVALEEYANSLEDRAVGVTSTDFTNFKFYIQHGAAAYCNSGTAAGANITCSNNGCPTIESNNVT
 MUT 3459   (1) MLLLSLLSAVTLAVASPVALEEYANSLEDRAVGVTSTDFTNFKFYIQHGAAAYCNSGTAAGANITCSNNGCPTIESNNVT
   MUT 10   (1) MLLLSLLSAVTLAVASPVALEEYANSLEDRAVGVTSTDFTNFKFYIQHGAAAYCNSGTAAGANITCSNNGCPTIESNNVT
   MUT 11   (1) MLLLSLLSAVTLAVASPVALEEYANSLEDRAVGVTSTDFTNFKFYIQHGAAAYCNSGTAAGANITCSNNGCPTIESNNVT
   MUT 12   (1) MLLLSLLSAVTLAVASPVALEEYANSLEDRAVGVISTDFTNFKFYIQHGAAAYCNSGTAAGANITCSNNGCPTIESNNVT
   F.ox US  (1) ------------------------------AVGVTTTDFSNFKFYI-HGAAAYCNSEAAAGSKITCSNNGCPTVQGNGAT
   F.ox EP  (1) MLLLPLLSAITLAVASPVALDDYVNSLEERAVGVTTTDFSNFKFYIQHGAAAYCNSEAAAGSKITCSNNGCPTVQGNGAT
               81                                                                             160
   KLM1wt  (81) VVASFTGSKTGIGGYVSTDSSRKEIVVAIRGSSNIRNWLTNLDFDQSDCSLVSGCGVHSGFQNAWAEISAQASAAVAKAR
    MUT 1  (81) VVASFTGSKTGIGGYVSTDSSRKEIVVAIRGSSNIRNWLTNLDFDQSDCSLVSGCGVHSGFQNAWAEISAQASAAVAKAR
    MUT 3  (81) VVASFTGSKTGIGGYVSTDSSRKEIVVAIRGSSNIRNWLTNLDFDQSDCSLVSGCGVHSGFQNAWAEISAQASAAVAKAR
    MUT 4  (81) VVASFTGSKTGIGGYVSTDSSRKEIVVAIRGSSNIRNWLTNLDFDQSDCSLVSGCGVHSGFQNAWAEISAQASAAVAKAR
    MUT 5  (81) VVASFTGSKTGIGGYVSTDSSRKEIVVAIRGSSNIRNWLTNLDFDQSDCSLVSGCGVHSGFQNAWAEISAQASAAVAKAR
    MUT 9  (81) VVASFTGSKTGIGGYVSTDSSRKEIVVAIRGSSNIRNWLTNLDFDQSDCSLVSGCGVHSGFQNAWAEISAQASAAVAKAR
  MUT 345  (81) VVASFTGSKTGIGGYVSTDSSRKEIVVAIRGSSNIRNWLTNLDFDQSDCSLVSGCGVHSGFQNAWAEISAQASAAVAKAR
 MUT 3459  (81) VVASFTGSKTGIGGYVSTDSSRKEIVVAIRGSSNIRNWLTNLDFDQSDCSLVSGCGVHSGFQNAWAEISAQASAAVAKAR
   MUT 10  (81) VVASFTGSKTGIGGYVSTDSSRKEIVVAIRGSSNIRNWLTNLDFDQSDCSLVSGCGVHSGFQNAWAEISAQASAAVAKAR
   MUT 11  (81) VVASFTGSKTGIGGYVSTDSSRKEIVVAIRGSSNIRNWLTNLDFDQSDCSLVSGCGVHSGFQNAWAEISAQASAAVAKAR
   MUT 12  (81) VVASFTGSKTGIGGYVSTDSSRKEIVVAIRGSSNIRNWLTNLDFDQSDCSLVSGCGVHSGFQNAWAEISAQASAAVAKAR
   F.ox US (81) IVTSFVGSKTGIGGYVATDSARKEIVVSFRGSINIRNWLTNLDFGQEDCSLVSGCGVHSGFQRAWNEIS-SATAAVASAR
   F.ox EP (81) IVTSFVGSKTGIGGYVATDSARKEIVVSFRGSINIRNWLTNLDFGQEDCSLVSGCGVHSGFQRAWNEISSQATAAVASAR
               161                                                                            240
   KLM1wt (161) KANPSFKVVATGHSLGGAVATLSAANLRAAGTPVDIYTYGAPRVGNAALSAFISNQAGGEFRVTHDKDPVPRLPPLIFGY
    MUT 1 (161) KANPSFKVVATGHSLGGAVATLSAANLRAAGTPVDIYTYGAPRVGNAALSAFISNQAGGEFRVTHDKDPVPRLPPLIFGY
    MUT 3 (161) KANPSFKVVATGHSLGGAVATLSAANLRAAGTPVDIYTYGAPRVGNAALSAFISNQAGGEFRVTHDKDPVPRLPPLIFGY
    MUT 4 (161) KANPSFKVVATGHSLGGAVATLSAANLRAAGTPVDIYTYGAPRVGNAALSAFISNQAGGEFRVTHDKDPVPRLPPLIFGY
    MUT 5 (161) KANPSFKVVATGHSLGGAVATLSAANLRANGTPVDIYTYGAPRVGNAALSAFISNQAGGEFRVTHDKDPVPRLPPLIFGY
    MUT 9 (161) KANPSFKVVATGHSLGGAVATLSAANLRAAGTPVDIYTYGAPRVGNAALSAFISNQAGGEFRVTHDKDPVPRLPPLIFGY
  MUT 345 (161) KANPSFKVVATGHSLGGAVATLSAANLRANGTPVDIYTYGAPRVGNAALSAFISNQAGGEFRVTHDKDPVPRLPPLIFGY
 MUT 3459 (161) KANPSFKVVATGHSLGGAVATLSAANLRANGTPVDIYTYGAPRVGNAALSAFISNQAGGEFRVTHDKDPVPRLPPLIFGY
   MUT 10 (161) KANPSFKVVATGHSLGGAVATLSAANLRANGTPVDIYTYGAPRVGNAALSAFISNQAGGEFRVTHDKDPVPRLPPLIFGY
   MUT 11 (161) KANPSFKVVATGHSLGGAVATLSAANLRANGTPVDIYTYGAPRVGNAALSAFISNQAGGEFRVTHDKDPVPRLPPLIFGY
   MUT 12 (161) KANPSFKVVATGHSLGGAVATLSAANLRANGTPVDIYTYGAPRVGNAALSAFISNQAGGEFRVTHDKDPVPRLPPLIFGY
  F.ox US (161) KANPSFNVLSTGHSLGGAVAVLAAANLRVGGTPVDIYTYGSPRVGN-ALSAFVSNQAGGEYRVTHADDPVPRLPPLIFGY
  F.ox EP (161) KANPSFNVLSTGHSLGGAVAVLAAANLRVGGTPVDIYTYGSPRVGNAQLSAFVSNQAGGEYRVTHADDPVPRLPPLIFGY
               241                                                                            320
   KLM1wt (241) RHTTPEYWLSGGGGDKVDYAISDVKVCEGAANLMCNGGTLGLDIDAHLHYFQATDACNAGGFSWRRYRSAKRESIDMRAT
    MUT 1 (241) RHTTPEYWLSGGGGDKVDYAISDVKVCEGAANLMCNGGTLGLDIDAHLHYFQATDACNAGGFSWRSYRSAKRESIDMRAT
    MUT 3 (241) RHTTPEYWLSGGGGDKVDYAISDVKVCEGAANLMCNGGTLGLDIDAHLHYFQATDACNAGGFSWRSYRSAKRESIDMRAT
    MUT 4 (241) RHTTPEYWLSGGGGDKVDYAISDVKVCEGAANLMCNGGTLGLDIDAHLHYFQATDACNAGGFSWRSYRSAKRESIDMRAT
    MUT 5 (241) RHTTPEYWLSGGGGDKVDYAISDVKVCEGAANLMCNGGTLGLDIDAHLHYFQATDACNAGGFSWRSYRSAKRESIDMRAT
    MUT 9 (241) RHTTPEYWLSGGGGDKVDYAISDVKVCEGAANLMCNGGTLGLDIDAHLHYFQATDACNAGGFSWRSYRSA--ESIDMRAT
  MUT 345 (241) RHTTPEYWLSGGGGDKVDYAISDVKVCEGAANLMCNGGTLGLDIDAHLHYFQATDACNAGGFSWRSYRSAKRESIDMRAT
 MUT 3459 (241) RHTTPEYWLSGGGGDKVDYAISDVKVCEGAANLMCNGGTLGLDIDAHLHYFQATDACNAGGFSWRSYRSA--ESIDMRAT
   MUT 10 (241) RHTTPEYWLSGGGGDKVDYAISDVKVCEGAANLMCNGGTLGLDIDAHLHYFQATDACNAGGFSWRS-------------T
   MUT 11 (241) RHTTPEYWLSGGGGDKVDYAISDVKVCEGAANLMCNGGTLGLDIDAHLHYFQATDACNAGGFSWRS-------------E
   MUT 12 (241) RHTTPEYWLSGGGGDKVDYAISDVKVCEGAANLMCNGGTLGLDIDAHLHYFQATDACNAGGFSWNS-------------T
  F.ox US (241) RHTTPEFWLSGGGGDKVDYTISDVKVCEGAANLGCNGGTLGLDIAAHLHYFQATDACNAGGFSWRRYRSA---SVDKR--
  F.ox EP (241) RHTTPEFWLSGGGGDKVDYTISDVKVCEGAANLGCNGGTLGLDIAAHLHYFQATDACNAGGFSWRRYRSA--ESVDKRAT
               321                        348
   KLM1wt (321) MTDAQLEAKLNSYVAMDQEYVKTHQNRT
    MUT 1 (321) MTDAQLEAKLNSYVAMDQEYVKTHQNRT
    MUT 3 (321) MTDAQLEAKLNSYVAMDQEYVKTHQNRT
    MUT 4 (321) MTDAQLEAKLNSYVAMDQEYVKTHQNRT
    MUT 5 (321) MTDAQLEAKLNSYVAMDQEYVKTHQNRT
    MUT 9 (321) MTDAQLEAKLNSYVAMDQEYVKTHQNRT
  MUT 345 (321) MTDAQLEAKLNSYVAMDQEYVKTHQNRT
 MUT 3459 (321) MTDAQLEAKLNSYVAMDQEYVKTHQNRT
   MUT 10 (321) MTDAQLEAKLNSYVAMDQEYVKTHQNRT
   MUT 11 (321) MTDAQLEAKLNSYVAMDQEYVKTHQNRT
   MUT 12 (321) MTDAQLEAKLNSYVAMDQEYVKTHQNRT
  F.ox US (321) ----------------------------
  F.ox EP (321) MTDAELEKKLNSYVQMDKEYVKNNQARS
```

FIGURE 30

SEQ ID No. 22

MLLLPLLSAITLAVASPVALDDYVNSLEERAVGVTTTDFSNFKFYIQHGAAAYCNSEAAAGSKITCSNNG
CPTVQGNGATIVTSFVGSKTGIGGYVATDSARKEIVVSFRGSINIRNWLTNLDFGQEDCSLVSGCGVHSG
FQRAWNEISSQATAAVASARKANPSFNVISTGHSLGGAVAVLAAANLRVGGTPVDIYTYGSPRVGNAQLS
AFVSNQAGGEYRVTHADDPVPRLPPLIFGYRHTTPEFWLSGGGGDKVDYTISDVKVCEGAANLGCNGGTL
GLDIAAHLHYFQATDACNAGGFSWRRYRSAESVDKRATMTDAELEKKLNSYVQMDKEYVKNNQARS

FIGURE 35

SEQ ID No. 23

AVGVTTTDFSNFKFYIHGAAAYCNSEAAAGSKITCSNNGCPTVQGNGATIVTSFVGSKTGIGGYVATDSA
RKEIVVSFRGSINIRNWLTNLDFGQEDCSLVSGCGVHSGFQRAWNEISSATAAVASARKANPSFNVISTG
HSLGGAVAVLAAANLRVGGTPVDIYTYGSPRVGNALSAFVSNQAGGEYRVTHADDPVPRLPPLIFGYRHT
TPEFWLSGGGGDKVDYTISDVKVCEGAANLGCNGGTLGLDIAAHLHYFQATDACNAGGFSWRRYRSASVD
KR

FIGURE 36

SEQ ID No. 24

```
TTGGAGAATA TTCCTTGTCA CG ATG CTT CTT CTA CCA CTC CTC TCG GCC ATC      52
ACC CTC GCG GTA GCC AGT CCT GTA GCT CTC GAC GAC TAC GTC AAC TCT      100
CTT GAG GAG CGA GCT GTT GGT GTC ACT ACA ACC GAC TTC AGC AAC TTC      148
AAG TTC TAC ATC CAA CAC GGC GCC GCA GCT TAC TGC AAC TCT GAA GCC      196
GCA GCT GGT TCC AAG ATC ACC TGC TCC AAC AAT GGC TGT CCA ACC GTT      244
CAG GGC AAC GGA GCG ACC ATC GTG ACA TCT TTC GTT GGC TCC AAG ACA      292
GGT ATC GGT GGC TAC GTC GCG ACA GAC TCT GCC CGA AAG GAA ATC GTC      340
GTC TCG TTC CGC GGA AGC ATC AAT ATT CGA AAC TGG CTT ACC AAC CTC      388
GAC TTC GGC CAG GAA GAC TGC AGT CTC GTC TCT GGA TGC GGT GTG CAC      436
TCT GGC TTC CAG CGA GCC TGG AAT GAG ATC TCG TCT CAA GCA ACC GCT      484
GCT GTT GCC TCC GCC CGC AAG GCG AAC CCT TCT TTC AAC GTC ATT TCT      532
ACA GGC CAC TCC CTT GGA GGT GCC GTG GCC GTT CTT GCT GCC GCA AAC      580
TTG AGA GTC GGT GGA ACA CCC GTC GAT ATT TAC ACC TAC GGC TCT CCC      628
CGT GTC GGA AAC GCG CAG CTC TCA GCC TTC GTC TCA AAC CAG GCT GGT      676
GGA GAG TAC CGC GTT ACA CAC GCT GAT GAC CCT GTC CCC CGT CTC CCT      724
CCT CTG ATC TTC GGA TAC AGG CAC ACA ACT CCT GAG TTC TGG CTG TCC      772
GGC GGT GGA GGC GAC AAG GTT GAC TAC ACC ATC AGC GAT GTC AAG GTC      820
TGT GAG GGT GCT GCC AAC CTT GGA TGC AAC GGT GGA ACT CTT GGT TTG      868
GAT ATT GCT GCT CAT CTG CAT TAC TTC CAG GCG ACT GAC GCC TGT AAC      916
GCT GGT GGC TTC TCT TGG CGA CGA TAC AGA AGC GCC GAG AGC GTC GAC      964
AAG AGG GCC ACC ATG ACT GAT GCC GAG CTT GAG AAG AAG CTG AAC TCT      1012
TAT GTC CAG ATG GAT AAG GAG TAT GTG AAG AAT AAC CAG GCC CGC TCT      1060
TAA CGAGGGTATG AGGTTTGATG GGAAATGACA TGATTCATGA ACGAAACCAT           1113
AGTACATATG ATGCAAATAG GATATAAAAA CATATTTCAT TCACTAGCTT TACACAA       1170
```

FIGURE 37

SEQ ID No. 25

MLLLSLLSAVTLAVASPVALEEYANSLEDRAVNVTSTDFTNFKFYIQHGAAAYCNSGTAAGAKITCSNNGCP
TIESNGVTVVASFTGSKTGIGGYVSTDSSRKEIVVAIRGSSNIRNWLTNLDFDQSDCSLVSGCGVHSGFQNA
WAEISAQASAAVAKARKANPSFKVVATGHSLGGAVATLSAANLRAAGTPVDIYTYGAPRVGNAALSAFISNQ
AGGEFRVTHDKDPVPRLPPLIFGYRHTTPEYWLSGGGGDKVDYAISDVKVCEGAANLMCNGGTLGLDIDAHL
HYFQATDACNAGGFSWRSYRSAKRESIDMRATMTDAQLEAKLNSYVAMDQEYVKTHQNRT

FIGURE 38

SEQ ID No. 26 ccgcggactggcatcatgcttcttctatccctcctctcggctgtcacccttgcggtggccagtcct
gtagccctcgaagaatacgccaactctcttgaagacagagccgttaacgtcacctcaacagacttc
accaacttcaagttctacatccagcatggcgccgcagcatactgcaactccgggaccgcagccggt
gcaaagatcacctgttccaacaatggttgcccaacgattgagtccaacggcgtgactgtcgtggca
tctttcactggctccaagactggcatcggcgggtacgtctcgacagatagctcccgtaaagaaatc
gtcgtcgcgatccgtggtagcagcaacatccgcaactggcttacaaacctcgactttgaccagtcc
gactgcagtcttgtctctggctgtggtgtgcactctggcttccagaacgcctgggccgagatctcg
gcgcaagcaagcgctgctgtagcaaaagctcgcaaggcgaacccttccttcaaggtcgtcgccaca
ggccactccctcggcggcgctgtggccacactgagtgctgcaaaccttcgagctgctggtacaccc
gtcgacatctacacatatggtgctcctcgagtaggaaacgccgcgctctctgctttcatctcgaac
caggctggcggagaatttcgcgttacgcacgacaaggatcccgtgcctcgtcttcccctctgatc
ttcggataccgacacacaaccccagagtactggctgtctggcggcggcggcgacaaggttgactac
gccatcagcgacgtcaaggtctgtgagggtgctgccaatctcatgtgcaacggtggaactctgggt
ctggatattgatgctcatctgcactacttccaggcgactgatgcttgcaacgctggtggcttctct
tggagatcttataggagcgccaagcgtgagagcatcgacatgagggctaccatgacagacgcacag
ttggaggccaagctcaactcttatgttgccatggatcaggagtatgtcaagactcaccaaaaccgc
acatgaggcgcgcc

SEQUENCE LISTING

```
<160> NUMBER OF SEQ ID NOS: 43

<210> SEQ ID NO 1
<211> LENGTH: 1070
<212> TYPE: DNA
<213> ORGANISM: Artificial Sequence
<220> FEATURE:
<223> OTHER INFORMATION: Description of Artificial Sequence: Synthetic
      polynucleotide encoding a lipolytic enzyme

<400> SEQUENCE: 1

ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaagatcacc tgttccaaca atggttgccc aacgattgag    240

tccaacggcg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctgctggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttccccct    720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga cgttatagga gcgccaagcg tgagagcatc    960

gacatgaggg ctaccatgac agacgcacag ttggaggcca agctcaactc ttatgttgcc   1020

atggatcagg agtatgtcaa gactcaccaa aaccgcacat gaggcgcgcc              1070


<210> SEQ ID NO 2
<211> LENGTH: 348
<212> TYPE: PRT
<213> ORGANISM: Fusarium heterosporum

<400> SEQUENCE: 2

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Lys Ile
    50                  55                  60

Thr Cys Ser Asn Asn Gly Cys Pro Thr Ile Glu Ser Asn Gly Val Thr
65                  70                  75                  80

Val Val Ala Ser Phe Thr Gly Ser Lys Thr Gly Ile Gly Gly Tyr Val
```

-continued

```
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345


<210> SEQ ID NO 3
<211> LENGTH: 8616
<212> TYPE: DNA
<213> ORGANISM: Artificial Sequence
<220> FEATURE:
<223> OTHER INFORMATION: Description of Artificial Sequence: Synthetic
      expression vector pTrex3

<400> SEQUENCE: 3

aagcttaact agtacttctc gagctctgta catgtccggt cgcgacgtac gcgtatcgat      60

ggcgccagct gcaggcggcc gcctgcagcc acttgcagtc ccgtggaatt ctcacggtga     120

atgtaggcct tttgtagggt aggaattgtc actcaagcac ccccaacctc cattacgcct     180

cccccataga gttcccaatc agtgagtcat ggcactgttc tcaaatagat tggggagaag     240

ttgacttccg cccagagctg aaggtcgcac aaccgcatga tatagggtcg gcaacggcaa     300

aaaagcacgt ggctcaccga aaagcaagat gtttgcgatc taacatccag gaacctggat     360

acatccatca tcacgcacga ccactttgat ctgctggtaa actcgtattc gccctaaacc     420

gaagtgcgtg gtaaatctac acgtgggccc ctttcggtat actgcgtgtg tcttctctag     480

gtgccattct tttcccttcc tctagtgttg aattgtttgt gttggagtcc gagctgtaac     540
```

-continued

```
tacctctgaa tctctggaga atggtggact aacgactacc gtgcacctgc atcatgtata    600
taatagtgat cctgagaagg ggggtttgga gcaatgtggg actttgatgg tcatcaaaca    660
aagaacgaag acgcctcttt tgcaaagttt tgtttcggct acggtgaaga actggatact    720
tgttgtgtct tctgtgtatt tttgtggcaa caagaggcca gagacaatct attcaaacac    780
caagcttgct cttttgagct acaagaacct gtggggtata tatctagagt tgtgaagtcg    840
gtaatcccgc tgtatagtaa tacgagtcgc atctaaatac tccgaagctg ctgcgaaccc    900
ggagaatcga gatgtgctgg aaagcttcta gcgagcggct aaattagcat gaaaggctat    960
gagaaattct ggagacggct tgttgaatca tggcgttcca ttcttcgaca agcaaagcgt   1020
tccgtcgcag tagcaggcac tcattcccga aaaaactcgg agattcctaa gtagcgatgg   1080
aaccggaata atataatagg caatacattg agttgcctcg acggttgcaa tgcaggggta   1140
ctgagcttgg acataactgt tccgtacccc acctcttctc aacctttggc gtttccctga   1200
ttcagcgtac ccgtacaagt cgtaatcact attaacccag actgaccgga cgtgttttgc   1260
ccttcatttg gagaaataat gtcattgcga tgtgtaattt gcctgcttga ccgactgggg   1320
ctgttcgaag cccgaatgta ggattgttat ccgaactctg ctcgtagagg catgttgtga   1380
atctgtgtcg ggcaggacac gcctcgaagg ttcacggcaa gggaaaccac cgatagcagt   1440
gtctagtagc aacctgtaaa gccgcaatgc agcatcactg gaaaatacaa accaatggct   1500
aaaagtacat aagttaatgc ctaaagaagt catataccag cggctaataa ttgtacaatc   1560
aagtggctaa acgtaccgta atttgccaac ggcttgtggg gttgcagaag caacggcaaa   1620
gccccacttc cccacgtttg tttcttcact cagtccaatc tcagctggtg atcccccaat   1680
tgggtcgctt gtttgttccg gtgaagtgaa agaagacaga ggtaagaatg tctgactcgg   1740
agcgttttgc atacaaccaa gggcagtgat ggaagacagt gaaatgttga cattcaagga   1800
gtatttagcc agggatgctt gagtgtatcg tgtaaggagg tttgtctgcc gatacgacga   1860
atactgtata gtcacttctg atgaagtggt ccatattgaa atgtaagtcg gcactgaaca   1920
ggcaaaagat tgagttgaaa ctgcctaaga tctcgggccc tcgggccttc ggcctttggg   1980
tgtacatgtt tgtgctccgg gcaaatgcaa agtgtggtag gatcgaacac actgctgcct   2040
ttaccaagca gctgagggta tgtgataggc aaatgttcag gggccactgc atggtttcga   2100
atagaaagag aagcttagcc aagaacaata gccgataaag atagcctcat taaacggaat   2160
gagctagtag gcaaagtcag cgaatgtgta tatataaagg ttcgaggtcc gtgcctccct   2220
catgctctcc ccatctactc atcaactcag atcctccagg agacttgtac accatctttt   2280
gaggcacaga aacccaatag tcaaccgcgg actgcgcatc atgtatcgga agttggccgt   2340
catctcggcc ttcttggcca cacctcgtgc tagactaggc gcgccgcgcg ccagctccgt   2400
gcgaaagcct gacgcaccgg tagattcttg gtgagcccgt atcatgacgg cggcgggagc   2460
tacatggccc cgggtgattt atttttttg tatctacttc tgaccctttt caaatatacg   2520
gtcaactcat ctttcactgg agatgcggcc tgcttggtat tgcgatgttg tcagcttggc   2580
aaattgtggc tttcgaaaac acaaaacgat tccttagtag ccatgcattt taagataacg   2640
gaatagaaga aagaggaaat taaaaaaaaa aaaaaaacaa acatcccgtt cataacccgt   2700
agaatcgccg ctcttcgtgt atcccagtac cagtttattt tgaatagctc gcccgctgga   2760
gagcatcctg aatgcaagta acaaccgtag aggctgacac ggcaggtgtt gctagggagc   2820
gtcgtgttct acaaggccag acgtcttcgc ggttgatata tatgtatgtt tgactgcagg   2880
ctgctcagcg acgacagtca agttcgccct cgctgcttgt gcaataatcg cagtggggaa   2940
```

-continued

```
gccacaccgt gactcccatc tttcagtaaa gctctgttgg tgtttatcag caatacacgt   3000

aatttaaact cgttagcatg gggctgatag cttaattacc gtttaccagt gccatggttc   3060

tgcagctttc cttggcccgt aaaattcggc gaagccagcc aatcaccagc taggcaccag   3120

ctaaacccta taattagtct cttatcaaca ccatccgctc cccgggatc aatgaggaga    3180

atgaggggga tgcggggcta aagaagccta cataaccctc atgccaactc ccagtttaca   3240

ctcgtcgagc caacatcctg actataagct aacacagaat gcctcaatcc tgggaagaac   3300

tggccgctga taagcgcgcc cgcctcgcaa aaaccatccc tgatgaatgg aaagtccaga   3360

cgctgcctgc ggaagacagc gttattgatt tcccaaagaa atcggggatc ctttcagagg   3420

ccgaactgaa gatcacagag gcctccgctg cagatcttgt gtccaagctg gcggccggag   3480

agttgacctc ggtggaagtt acgctagcat tctgtaaacg ggcagcaatc gcccagcagt   3540

tagtagggtc ccctctacct ctcagggaga tgtaacaacg ccaccttatg ggactatcaa   3600

gctgacgctg gcttctgtgc agacaaactg cgcccacgag ttcttccctg acgccgctct   3660

cgcgcaggca agggaactcg atgaatacta cgcaaagcac aagagacccg ttggtccact   3720

ccatggcctc cccatctctc tcaaagacca gcttcgagtc aaggtacacc gttgccccta   3780

agtcgttaga tgtccctttt tgtcagctaa catatgccac cagggctacg aaacatcaat   3840

gggctacatc tcatggctaa acaagtacga cgaaggggac tcggttctga caaccatgct   3900

ccgcaaagcc ggtgccgtct tctacgtcaa gacctctgtc ccgcagaccc tgatggtctg   3960

cgagacagtc aacaacatca tcgggcgcac cgtcaaccca cgcaacaaga actggtcgtg   4020

cggcggcagt tctggtggtg agggtgcgat cgttgggatt cgtggtggcg tcatcggtgt   4080

aggaacggat atcggtggct cgattcgagt gccggccgcg ttcaacttcc tgtacggtct   4140

aaggccgagt catgggcggc tgccgtatgc aaagatggcg aacagcatgg agggtcagga   4200

gacggtgcac agcgttgtcg ggccgattac gcactctgtt gagggtgagt ccttcgcctc   4260

ttccttcttt tcctgctcta taccaggcct ccactgtcct cctttcttgc tttttatact   4320

atatacgaga ccggcagtca ctgatgaagt atgttagacc tccgcctctt caccaaatcc   4380

gtcctcggtc aggagccatg gaaatacgac tccaaggtca tccccatgcc ctggcgccag   4440

tccgagtcgg acattattgc ctccaagatc aagaacggcg ggctcaatat cggctactac   4500

aacttcgacg gcaatgtcct tccacaccct cctatcctgc gcggcgtgga aaccaccgtc   4560

gccgcactcg ccaaagccgg tcacaccgtg accccgtgga cgccatacaa gcacgatttc   4620

ggccacgatc tcatctccca tatctacgcg gctgacggca gcgccgacgt aatgcgcgat   4680

atcagtgcat ccggcgagcc ggcgattcca aatatcaaag acctactgaa cccgaacatc   4740

aaagctgtta acatgaacga gctctgggac acgcatctcc agaagtggaa ttaccagatg   4800

gagtaccttg agaaatggcg ggaggctgaa gaaaaggccg ggaaggaact ggacgccatc   4860

atcgcgccga ttacgcctac cgctgcggta cggcatgacc agttccggta ctatgggtat   4920

gcctctgtga tcaacctgct ggatttcacg agcgtggttg ttccggttac ctttgcggat   4980

aagaacatcg ataagaagaa tgagagtttc aaggcggtta gtgagcttga tgccctcgtg   5040

caggaagagt atgatccgga ggcgtaccat ggggcaccgg ttgcagtgca ggttatcgga   5100

cggagactca gtgaagagag gacgttggcg attgcagagg aagtggggaa gttgctggga   5160

aatgtggtga ctccatagct aataagtgtc agatagcaat ttgcacaaga aatcaatacc   5220

agcaactgta aataagcgct gaagtgacca tgccatgcta cgaaagagca gaaaaaaacc   5280
```

-continued

```
tgccgtagaa ccgaagagat atgacacgct tccatctctc aaaggaagaa tcccttcagg   5340
gttgcgtttc cagtctagac acgtataacg gcacaagtgt ctctcaccaa atgggttata   5400
tctcaaatgt gatctaagga tggaaagccc agaatatcga tcgcgcgcag atccatatat   5460
agggcccggg ttataattac ctcaggtcga cgtcccatgg ccattcgaat tcgtaatcat   5520
ggtcatagct gtttcctgtg tgaaattgtt atccgctcac aattccacac aacatacgag   5580
ccggaagcat aaagtgtaaa gcctggggtg cctaatgagt gagctaactc acattaattg   5640
cgttgcgctc actgcccgct ttccagtcgg gaaacctgtc gtgccagctg cattaatgaa   5700
tcggccaacg cgcggggaga ggcggtttgc gtattgggcg ctcttccgct tcctcgctca   5760
ctgactcgct gcgctcggtc gttcggctgc ggcgagcggt atcagctcac tcaaaggcgg   5820
taatacggtt atccacagaa tcaggggata acgcaggaaa gaacatgtga gcaaaaggcc   5880
agcaaaaggc caggaaccgt aaaaaggccg cgttgctggc gtttttccat aggctccgcc   5940
cccctgacga gcatcacaaa aatcgacgct caagtcagag gtggcgaaac ccgacaggac   6000
tataaagata ccaggcgttt ccccctggaa gctccctcgt gcgctctcct gttccgaccc   6060
tgccgcttac cggatacctg tccgcctttc tcccttcggg aagcgtggcg ctttctcata   6120
gctcacgctg taggtatctc agttcggtgt aggtcgttcg ctccaagctg ggctgtgtgc   6180
acgaaccccc cgttcagccc gaccgctgcg ccttatccgg taactatcgt cttgagtcca   6240
acccggtaag acacgactta tcgccactgg cagcagccac tggtaacagg attagcagag   6300
cgaggtatgt aggcggtgct acagagttct tgaagtggtg gcctaactac ggctacacta   6360
gaagaacagt atttggtatc tgcgctctgc tgaagccagt taccttcgga aaaagagttg   6420
gtagctcttg atccggcaaa caaaccaccg ctggtagcgg tggttttttt gtttgcaagc   6480
agcagattac gcgcagaaaa aaaggatctc aagaagatcc tttgatcttt tctacggggt   6540
ctgacgctca gtggaacgaa aactcacgtt aagggatttt ggtcatgaga ttatcaaaaa   6600
ggatcttcac ctagatcctt ttaaattaaa aatgaagttt taaatcaatc taaagtatat   6660
atgagtaaac ttggtctgac agttaccaat gcttaatcag tgaggcacct atctcagcga   6720
tctgtctatt tcgttcatcc atagttgcct gactccccgt cgtgtagata actacgatac   6780
gggagggctt accatctggc cccagtgctg caatgatacc gcgagaccca cgctcaccgg   6840
ctccagattt atcagcaata aaccagccag ccggaagggc cgagcgcaga agtggtcctg   6900
caactttatc cgcctccatc cagtctatta attgttgccg ggaagctaga gtaagtagtt   6960
cgccagttaa tagtttgcgc aacgttgttg ccattgctac aggcatcgtg gtgtcacgct   7020
cgtcgtttgg tatggcttca ttcagctccg gttcccaacg atcaaggcga gttacatgat   7080
cccccatgtt gtgcaaaaaa gcggttagct ccttcggtcc tccgatcgtt gtcagaagta   7140
agttggccgc agtgttatca ctcatggtta tggcagcact gcataattct cttactgtca   7200
tgccatccgt aagatgcttt tctgtgactg gtgagtactc aaccaagtca ttctgagaat   7260
agtgtatgcg gcgaccgagt tgctcttgcc cggcgtcaat acgggataat accgcgccac   7320
atagcagaac tttaaaagtg ctcatcattg gaaaacgttc ttcggggcga aaactctcaa   7380
ggatcttacc gctgttgaga tccagttcga tgtaacccac tcgtgcaccc aactgatctt   7440
cagcatcttt tactttcacc agcgtttctg ggtgagcaaa aacaggaagg caaaatgccg   7500
caaaaaaggg aataagggcg acacggaaat gttgaatact catactcttc ctttttcaat   7560
attattgaag catttatcag ggttattgtc tcatgagcgg atacatattt gaatgtattt   7620
agaaaaataa acaaataggg gttccgcgca catttccccg aaaagtgcca cctgacgtct   7680
```

aagaaaccat tattatcatg acattaacct ataaaaatag gcgtatcacg aggccctttc 7740
gtctcgcgcg tttcggtgat gacggtgaaa acctctgaca catgcagctc ccggagacgg 7800
tcacagcttg tctgtaagcg gatgccggga gcagacaagc ccgtcagggc gcgtcagcgg 7860
gtgttggcgg gtgtcggggc tggcttaact atgcggcatc agagcagatt gtactgagag 7920
tgcaccataa aattgtaaac gttaatattt tgttaaaatt cgcgttaaat ttttgttaaa 7980
tcagctcatt ttttaaccaa taggccgaaa tcggcaaaat cccttataaa tcaaaagaat 8040
agcccgagat agggttgagt gttgttccag tttggaacaa gagtccacta ttaaagaacg 8100
tggactccaa cgtcaaaggg cgaaaaaccg tctatcaggg cgatggccca ctacgtgaac 8160
catcacccaa atcaagtttt ttggggtcga ggtgccgtaa agcactaaat cggaacccta 8220
aagggagccc ccgatttaga gcttgacggg gaaagccggc gaacgtggcg agaaaggaag 8280
ggaagaaagc gaaaggagcg ggcgctaggg cgctggcaag tgtagcggtc acgctgcgcg 8340
taaccaccac acccgccgcg cttaatgcgc cgctacaggg cgcgtactat ggttgctttg 8400
acgtatgcgg tgtgaaatac cgcacagatg cgtaaggaga aaataccgca tcaggcgcca 8460
ttcgccattc aggctgcgca actgttggga agggcgatcg gtgcgggcct cttcgctatt 8520
acgccagctg gcgaaagggg gatgtgctgc aaggcgatta agttgggtaa cgccagggtt 8580
ttcccagtca cgacgttgta aaacgacggc cagtgc 8616

<210> SEQ ID NO 4
<211> LENGTH: 1070
<212> TYPE: DNA
<213> ORGANISM: Artificial Sequence
<220> FEATURE:
<223> OTHER INFORMATION: Description of Artificial Sequence: Synthetic mutant lipolytic enzyme “mut 3”

<400> SEQUENCE: 4
ccgcggactg gcatcatgct tcttctatcc ctcctctcgg ctgtcaccct tgcggtggcc 60
agtcctgtag ccctcgaaga atacgccaac tctcttgaag acagagccgt tggagtcacc 120
tcaacagact tcaccaactt caagttctac atccagcatg gcgccgcagc atactgcaac 180
tccgggaccg cagccggtgc aaacatcacc tgttccaaca atggttgccc aacgattgag 240
tccaacggcg tgactgtcgt ggcatctttc actggctcca agactggcat cggcgggtac 300
gtctcgacag atagctcccg taaagaaatc gtcgtcgcga tccgtggtag cagcaacatc 360
cgcaactggc ttacaaacct cgactttgac cagtccgact gcagtcttgt ctctggctgt 420
ggtgtgcact ctggcttcca gaacgcctgg gccgagatct cggcgcaagc aagcgctgct 480
gtagcaaaag ctcgcaaggc gaacccttcc ttcaaggtcg tcgccacagg ccactccctc 540
ggcggcgctg tggccacact gagtgctgca aaccttcgag ctgctggtac acccgtcgac 600
atctacacat atggtgctcc tcgagtagga aacgccgcgc tctctgcttt catctcgaac 660
caggctggcg gagaatttcg cgttacgcac gacaaggatc ccgtgcctcg tcttccccct 720
ctgatcttcg gataccgaca cacaacccca gagtactggc tgtctggcgg cggcggcgac 780
aaggttgact acgccatcag cgacgtcaag gtctgtgagg gtgctgccaa tctcatgtgc 840
aacggtggaa ctctgggtct ggatattgat gctcatctgc actacttcca ggcgactgat 900
gcttgcaacg ctggtggctt ctcttggaga tcttatagga gcgccaagcg tgagagcatc 960
gacatgaggg ctaccatgac agacgcacag ttggaggcca agctcaactc ttatgttgcc 1020
atggatcagg agtatgtcaa gactcaccaa aaccgcacat gaggcgcgcc 1070

```
<210> SEQ ID NO 5
<211> LENGTH: 348
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 3"

<400> SEQUENCE: 5

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Gly Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345
```

<210> SEQ ID NO 6
<211> LENGTH: 1070
<212> TYPE: DNA
<213> ORGANISM: Artificial Sequence
<220> FEATURE:
<223> OTHER INFORMATION: Description of Artificial Sequence: Synthetic
mutant lipolytic enzyme “mut 4”

<400> SEQUENCE: 6

```
ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaagatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctgctggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccccct   720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgccaagcg tgagagcatc    960

gacatgaggg ctaccatgac agacgcacag ttggaggcca agctcaactc ttatgttgcc   1020

atggatcagg agtatgtcaa gactcaccaa aaccgcacat gaggcgcgcc              1070
```

<210> SEQ ID NO 7
<211> LENGTH: 348
<212> TYPE: PRT
<213> ORGANISM: Artificial Sequence
<220> FEATURE:
<223> OTHER INFORMATION: Description of Artificial Sequence: Synthetic
mutant lipolytic enzyme “mut 4”

<400> SEQUENCE: 7

```
Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Lys Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
```

```
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345
```

<210> SEQ ID NO 8
<211> LENGTH: 1070
<212> TYPE: DNA
<213> ORGANISM: Artificial Sequence
<220> FEATURE:
<223> OTHER INFORMATION: Description of Artificial Sequence: Synthetic mutant lipolytic enzyme “mut 5”

<400> SEQUENCE: 8

```
ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaagatcacc tgttccaaca atggttgccc aacgattgag    240

tccaacggcg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccct     720
```

```
ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgccaagcg tgagagcatc    960

gacatgaggg ctaccatgac agacgcacag ttggaggcca agctcaactc ttatgttgcc   1020

atggatcagg agtatgtcaa gactcaccaa aaccgcacat gaggcgcgcc              1070
```

```
<210> SEQ ID NO 9
<211> LENGTH: 348
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 5"

<400> SEQUENCE: 9

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Lys Ile
    50                  55                  60

Thr Cys Ser Asn Asn Gly Cys Pro Thr Ile Glu Ser Asn Gly Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300
```

-continued

```
Arg Ser Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345


<210> SEQ ID NO 10
<211> LENGTH: 1070
<212> TYPE: DNA
<213> ORGANISM: Artificial Sequence
<220> FEATURE:
<223> OTHER INFORMATION: Description of Artificial Sequence: Synthetic
      mutant lipolytic enzyme "mut 345"

<400> SEQUENCE: 10

ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaacatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccccct    720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgccaagcg tgagagcatc    960

gacatgaggg ctaccatgac agacgcacag ttggaggcca agctcaactc ttatgttgcc   1020

atggatcagg agtatgtcaa gactcaccaa aaccgcacat gaggcgcgcc              1070


<210> SEQ ID NO 11
<211> LENGTH: 348
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 345"

<400> SEQUENCE: 11

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60
```

```
Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345
```

```
<210> SEQ ID NO 12
<211> LENGTH: 1065
<212> TYPE: DNA
<213> ORGANISM: Artificial Sequence
<220> FEATURE:
<223> OTHER INFORMATION: Description of Artificial Sequence: Synthetic
      mutant lipolytic enzyme "mut 3459"

<400> SEQUENCE: 12

ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaacatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420
```

```
ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccccct   720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgctgagag catcgacatg    960

agggctacca tgacagacgc acagttggag gccaagctca actcttatgt tgccatggat   1020

caggagtatg tcaagactca ccaaaaccgc acatgaggcg cgccg                   1065
```

<210> SEQ ID NO 13
<211> LENGTH: 346
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 3459"

<400> SEQUENCE: 13

```
Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240
```

-continued

```
Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Glu Ser Ile Asp Met Arg Ala Thr Met Thr
305                 310                 315                 320

Asp Ala Gln Leu Glu Ala Lys Leu Asn Ser Tyr Val Ala Met Asp Gln
                325                 330                 335

Glu Tyr Val Lys Thr His Gln Asn Arg Thr
            340                 345
```

<210> SEQ ID NO 14
<211> LENGTH: 1064
<212> TYPE: DNA
<213> ORGANISM: Artificial Sequence
<220> FEATURE:
<223> OTHER INFORMATION: Description of Artificial Sequence: Synthetic mutant lipolytic enzyme "mut 9"

<400> SEQUENCE: 14

```
ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaagatcacc tgttccaaca atggttgccc aacgattgag    240

tccaacggcg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctgctggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttccccct    720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgctgagag catcgacatg    960

agggctacca tgacagacgc acagttggag gccaagctca actcttatgt tgccatggat   1020

caggagtatg tcaagactca ccaaaaccgc acatgaggcg cgcc                    1064
```

<210> SEQ ID NO 15
<211> LENGTH: 348
<212> TYPE: PRT
<213> ORGANISM: Artificial Sequence
<220> FEATURE:
<223> OTHER INFORMATION: Description of Artificial Sequence: Synthetic mutant lipolytic enzyme "mut 9"

<400> SEQUENCE: 15

-continued

```
Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Lys Ile
    50                  55                  60

Thr Cys Ser Asn Asn Gly Cys Pro Thr Ile Glu Ser Asn Gly Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345
```

```
<210> SEQ ID NO 16
<211> LENGTH: 1031
<212> TYPE: DNA
<213> ORGANISM: Artificial Sequence
<220> FEATURE:
<223> OTHER INFORMATION: Description of Artificial Sequence: Synthetic
      mutant lipolytic enzyme "mut 10"

<400> SEQUENCE: 16

ccgcggactg gcatcatgct tcttctatcc ctcctctcgg ctgtcaccct tgcggtggcc      60
```

-continued

```
agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaacatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttccccct    720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggcgc tccaccatga cagacgcaca gttggaggcc    960

aagctcaact cttatgttgc catggatcag gagtatgtca agactcacca aaaccgcaca   1020

tgaggcgcgc c                                                        1031
```

```
<210> SEQ ID NO 17
<211> LENGTH: 335
<212> TYPE: PRT
<213> ORGANISM: Artificial Sequence
<220> FEATURE:
<223> OTHER INFORMATION: Description of Artificial Sequence: Synthetic
      mutant lipolytic enzyme “mut10”

<400> SEQUENCE: 17

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
```

-continued

```
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Thr Met Thr Asp Ala Gln Leu Glu Ala Lys Leu Asn Ser Tyr
305                 310                 315                 320

Val Ala Met Asp Gln Glu Tyr Val Lys Thr His Gln Asn Arg Thr
                325                 330                 335


<210> SEQ ID NO 18
<211> LENGTH: 1031
<212> TYPE: DNA
<213> ORGANISM: Artificial Sequence
<220> FEATURE:
<223> OTHER INFORMATION: Description of Artificial Sequence: Synthetic
      mutant lipolytic enzyme "mut 11"

<400> SEQUENCE: 18

ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaacatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccct     720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggcgc tccgagatga cagacgcaca gttggaggcc    960

aagctcaact cttatgttgc catggatcag gagtatgtca agactcacca aaaccgcaca   1020

tgaggcgcgc c                                                        1031


<210> SEQ ID NO 19
<211> LENGTH: 335
```

<212> TYPE: PRT
<213> ORGANISM: Artificial Sequence
<220> FEATURE:
<223> OTHER INFORMATION: Description of Artificial Sequence: Synthetic
mutant lipolytic enzyme “mut 11”

<400> SEQUENCE: 19

```
Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Glu Met Thr Asp Ala Gln Leu Glu Ala Lys Leu Asn Ser Tyr
305                 310                 315                 320

Val Ala Met Asp Gln Glu Tyr Val Lys Thr His Gln Asn Arg Thr
                325                 330                 335
```

<210> SEQ ID NO 20
<211> LENGTH: 1031
<212> TYPE: DNA
<213> ORGANISM: Artificial Sequence
<220> FEATURE:
<223> OTHER INFORMATION: Description of Artificial Sequence: Synthetic
mutant lipolytic enzyme “mut 12”

<400> SEQUENCE: 20

```
ccgcggactg gcatcatgct tcttctatcc ctcctctcgg ctgtcaccct tgcggtggcc     60

agtcctgtag ccctcgaaga atacgccaac tctcttgaag acagagccgt tggagtcacc    120

tcaacagact tcaccaactt caagttctac atccagcatg gcgccgcagc atactgcaac    180

tccgggaccg cagccggtgc aaacatcacc tgttccaaca atggttgccc aacgattgag    240

tccaacaacg tgactgtcgt ggcatctttc actggctcca agactggcat cggcgggtac    300

gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctaacggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccccct    720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaac tccaccatga cagacgcaca gttggaggcc    960

aagctcaact cttatgttgc catggatcag gagtatgtca agactcacca aaaccgcaca   1020

tgaggcgcgc c                                                         1031
```

<210> SEQ ID NO 21
<211> LENGTH: 334
<212> TYPE: PRT
<213> ORGANISM: Artificial Sequence
<220> FEATURE:
<223> OTHER INFORMATION: Description of Artificial Sequence: Synthetic
      mutant lipolytic enzyme “mut 12”

<400> SEQUENCE: 21

```
Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160
```

```
Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Asn Ser Thr Met Thr Asp Ala Gln Leu Glu Ala Lys Leu Asn Ser Tyr
305                 310                 315                 320

Val Ala Met Asp Gln Glu Tyr Val Lys Thr His Gln Asn Arg
                325                 330


<210> SEQ ID NO 22
<211> LENGTH: 346
<212> TYPE: PRT
<213> ORGANISM: Fusarium oxysporum

<400> SEQUENCE: 22

Met Leu Leu Leu Pro Leu Leu Ser Ala Ile Thr Leu Ala Val Ala Ser
1               5                   10                  15

Pro Val Ala Leu Asp Asp Tyr Val Asn Ser Leu Glu Glu Arg Ala Val
            20                  25                  30

Gly Val Thr Thr Thr Asp Phe Ser Asn Phe Lys Phe Tyr Ile Gln His
        35                  40                  45

Gly Ala Ala Ala Tyr Cys Asn Ser Glu Ala Ala Ala Gly Ser Lys Ile
    50                  55                  60

Thr Cys Ser Asn Asn Gly Cys Pro Thr Val Gln Gly Asn Gly Ala Thr
65                  70                  75                  80

Ile Val Thr Ser Phe Val Gly Ser Lys Thr Gly Ile Gly Gly Tyr Val
                85                  90                  95

Ala Thr Asp Ser Ala Arg Lys Glu Ile Val Val Ser Phe Arg Gly Ser
            100                 105                 110

Ile Asn Ile Arg Asn Trp Leu Thr Asn Leu Asp Phe Gly Gln Glu Asp
        115                 120                 125

Cys Ser Leu Val Ser Gly Cys Gly Val His Ser Gly Phe Gln Arg Ala
    130                 135                 140

Trp Asn Glu Ile Ser Ser Gln Ala Thr Ala Ala Val Ala Ser Ala Arg
145                 150                 155                 160

Lys Ala Asn Pro Ser Phe Asn Val Ile Ser Thr Gly His Ser Leu Gly
                165                 170                 175

Gly Ala Val Ala Val Leu Ala Ala Ala Asn Leu Arg Val Gly Gly Thr
            180                 185                 190

Pro Val Asp Ile Tyr Thr Tyr Gly Ser Pro Arg Val Gly Asn Ala Gln
```

```
        195                 200                 205

Leu Ser Ala Phe Val Ser Asn Gln Ala Gly Gly Glu Tyr Arg Val Thr
    210                 215                 220

His Ala Asp Asp Pro Val Pro Arg Leu Pro Pro Leu Ile Phe Gly Tyr
225                 230                 235                 240

Arg His Thr Thr Pro Glu Phe Trp Leu Ser Gly Gly Gly Gly Asp Lys
                245                 250                 255

Val Asp Tyr Thr Ile Ser Asp Val Lys Val Cys Glu Gly Ala Ala Asn
            260                 265                 270

Leu Gly Cys Asn Gly Gly Thr Leu Gly Leu Asp Ile Ala Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
            340                 345


<210> SEQ ID NO 23
<211> LENGTH: 282
<212> TYPE: PRT
<213> ORGANISM: Fusarium oxysporum

<400> SEQUENCE: 23

Ala Val Gly Val Thr Thr Thr Asp Phe Ser Asn Phe Lys Phe Tyr Ile
1               5                   10                  15

His Gly Ala Ala Ala Tyr Cys Asn Ser Glu Ala Ala Ala Gly Ser Lys
            20                  25                  30

Ile Thr Cys Ser Asn Asn Gly Cys Pro Thr Val Gln Gly Asn Gly Ala
        35                  40                  45

Thr Ile Val Thr Ser Phe Val Gly Ser Lys Thr Gly Ile Gly Gly Tyr
    50                  55                  60

Val Ala Thr Asp Ser Ala Arg Lys Glu Ile Val Val Ser Phe Arg Gly
65                  70                  75                  80

Ser Ile Asn Ile Arg Asn Trp Leu Thr Asn Leu Asp Phe Gly Gln Glu
                85                  90                  95

Asp Cys Ser Leu Val Ser Gly Cys Gly Val His Ser Gly Phe Gln Arg
            100                 105                 110

Ala Trp Asn Glu Ile Ser Ser Ala Thr Ala Ala Val Ala Ser Ala Arg
        115                 120                 125

Lys Ala Asn Pro Ser Phe Asn Val Ile Ser Thr Gly His Ser Leu Gly
    130                 135                 140

Gly Ala Val Ala Val Leu Ala Ala Ala Asn Leu Arg Val Gly Gly Thr
145                 150                 155                 160

Pro Val Asp Ile Tyr Thr Tyr Gly Ser Pro Arg Val Gly Asn Ala Leu
                165                 170                 175

Ser Ala Phe Val Ser Asn Gln Ala Gly Gly Glu Tyr Arg Val Thr His
            180                 185                 190

Ala Asp Asp Pro Val Pro Arg Leu Pro Pro Leu Ile Phe Gly Tyr Arg
        195                 200                 205

His Thr Thr Pro Glu Phe Trp Leu Ser Gly Gly Gly Gly Asp Lys Val
    210                 215                 220
```

-continued

```
Asp Tyr Thr Ile Ser Asp Val Lys Val Cys Glu Gly Ala Ala Asn Leu
225                 230                 235                 240

Gly Cys Asn Gly Gly Thr Leu Gly Leu Asp Ile Ala Ala His Leu His
                245                 250                 255

Tyr Phe Gln Ala Thr Asp Ala Cys Asn Ala Gly Gly Phe Ser Trp Arg
            260                 265                 270

Arg Tyr Arg Ser Ala Ser Val Asp Lys Arg
        275                 280


<210> SEQ ID NO 24
<211> LENGTH: 1170
<212> TYPE: DNA
<213> ORGANISM: Fusarium oxysporum

<400> SEQUENCE: 24

ttggagaata ttccttgtca cgatgcttct tctaccactc ctctcggcca tcaccctcgc     60

ggtagccagt cctgtagctc tcgacgacta cgtcaactct cttgaggagc gagctgttgg    120

tgtcactaca accgacttca gcaacttcaa gttctacatc caacacggcg ccgcagctta    180

ctgcaactct gaagccgcag ctggttccaa gatcacctgc tccaacaatg gctgtccaac    240

cgttcagggc aacggagcga ccatcgtgac atctttcgtt ggctccaaga caggtatcgg    300

tggctacgtc gcgacagact ctgcccgaaa ggaaatcgtc gtctcgttcc gcggaagcat    360

caatattcga aactggctta ccaacctcga cttcggccag gaagactgca gtctcgtctc    420

tggatgcggt gtgcactctg gcttccagcg agcctggaat gagatctcgt ctcaagcaac    480

cgctgctgtt gcctccgccc gcaaggcgaa cccttctttc aacgtcattt ctacaggcca    540

ctcccttgga ggtgccgtgg ccgttcttgc tgccgcaaac ttgagagtcg gtggaacacc    600

cgtcgatatt tacacctacg gctctccccg tgtcggaaac gcgcagctct cagccttcgt    660

ctcaaaccag gctggtggag agtaccgcgt tacacacgct gatgaccctg tcccccgtct    720

ccctcctctg atcttcggat acaggcacac aactcctgag ttctggctgt ccggcggtgg    780

aggcgacaag gttgactaca ccatcagcga tgtcaaggtc tgtgagggtg ctgccaacct    840

tggatgcaac ggtggaactc ttggtttgga tattgctgct catctgcatt acttccaggc    900

gactgacgcc tgtaacgctg gtggcttctc ttggcgacga tacagaagcg ccgagagcgt    960

cgacaagagg gccaccatga ctgatgccga gcttgagaag aagctgaact cttatgtcca   1020

gatggataag gagtatgtga agaataacca ggcccgctct taacgagggt atgaggtttg   1080

atgggaaatg acatgattca tgaacgaaac catagtacat atgatgcaaa taggatataa   1140

aaacatattt cattcactag ctttacacaa                                    1170


<210> SEQ ID NO 25
<211> LENGTH: 348
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 1"

<400> SEQUENCE: 25

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Asn Val Thr Ser Thr Asp Phe Thr Asn Phe Lys Phe Tyr Ile Gln His
        35                  40                  45
```

```
Gly Ala Ala Ala Tyr Cys Asn Ser Gly Thr Ala Ala Gly Ala Lys Ile
    50                  55                  60

Thr Cys Ser Asn Asn Gly Cys Pro Thr Ile Glu Ser Asn Gly Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Lys Arg Glu Ser Ile Asp Met Arg Ala Thr
305                 310                 315                 320

Met Thr Asp Ala Gln Leu Glu Ala Lys Leu Asn Ser Tyr Val Ala Met
                325                 330                 335

Asp Gln Glu Tyr Val Lys Thr His Gln Asn Arg Thr
            340                 345
```

<210> SEQ ID NO 26
<211> LENGTH: 1070
<212> TYPE: DNA
<213> ORGANISM: Artificial Sequence
<220> FEATURE:
<223> OTHER INFORMATION: Description of Artificial Sequence: Synthetic mutant lipolytic enzyme “mut 1”

<400> SEQUENCE: 26

```
ccgcggactg gcatcatgct tcttctatcc ctcctctcgg ctgtcaccct tgcggtggcc      60

agtcctgtag ccctcgaaga atacgccaac tctcttgaag acagagccgt taacgtcacc     120

tcaacagact tcaccaactt caagttctac atccagcatg gcgccgcagc atactgcaac     180

tccgggaccg cagccggtgc aaagatcacc tgttccaaca atggttgccc aacgattgag     240

tccaacggcg tgactgtcgt ggcatctttc actggctcca agactggcat cggcgggtac     300
```

-continued

```
gtctcgacag atagctcccg taaagaaatc gtcgtcgcga tccgtggtag cagcaacatc    360

cgcaactggc ttacaaacct cgactttgac cagtccgact gcagtcttgt ctctggctgt    420

ggtgtgcact ctggcttcca gaacgcctgg gccgagatct cggcgcaagc aagcgctgct    480

gtagcaaaag ctcgcaaggc gaacccttcc ttcaaggtcg tcgccacagg ccactccctc    540

ggcggcgctg tggccacact gagtgctgca aaccttcgag ctgctggtac acccgtcgac    600

atctacacat atggtgctcc tcgagtagga aacgccgcgc tctctgcttt catctcgaac    660

caggctggcg gagaatttcg cgttacgcac gacaaggatc ccgtgcctcg tcttcccccct   720

ctgatcttcg gataccgaca cacaacccca gagtactggc tgtctggcgg cggcggcgac    780

aaggttgact acgccatcag cgacgtcaag gtctgtgagg gtgctgccaa tctcatgtgc    840

aacggtggaa ctctgggtct ggatattgat gctcatctgc actacttcca ggcgactgat    900

gcttgcaacg ctggtggctt ctcttggaga tcttatagga gcgccaagcg tgagagcatc    960

gacatgaggg ctaccatgac agacgcacag ttggaggcca agctcaactc ttatgttgcc   1020

atggatcagg agtatgtcaa gactcaccaa aaccgcacat gaggcgcgcc              1070


<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

ctgatatcct ggcatggtga atctccgtg                                        29


<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

catggcgcgc cgaggcagat aggcggacga ag                                    32


<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

catggcgcgc cgtgtaagtg cgtggctgca g                                     31


<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

ctgatatcga tcgagtcgaa ctgtcgcttc                                       30
```

```
<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

gtttcgcatg gcgcgcctga gacaatgg                                          28


<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

cacaggcgcg ccgatcgcca tcccgtcgcg tc                                     32


<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

ctatgacatg ccctgaggcg atgctggcca ggtacgagct g                           41


<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

cagcctcgcg gtcacagtga gaggaacggg gtgaagtcgt ataag                       45


<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

ctagcgatcg cgtgtgcaca taggtgagtt ctcc                                   34


<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

ctagcgatcg cgcagactgg catgcctcaa tcac                                   34


<210> SEQ ID NO 37
```

-continued

<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
ctcgccatct gacaacctac aaatc 25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
ctagtaccct gagttgtctc gcctcc 26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
cctctaccat aacaggatcc atctg 25

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
cgtgagctga tgaaggagag aacaaagg 28

<210> SEQ ID NO 41
<211> LENGTH: 346
<212> TYPE: PRT
<213> ORGANISM: Artificial Sequence
<220> FEATURE:
<223> OTHER INFORMATION: Description of Artificial Sequence: Synthetic
mutant lipolytic enzyme "mut 9"

<400> SEQUENCE: 41

Met Leu Leu Leu Ser Leu Leu Ser Ala Val Thr Leu Ala Val Ala Ser
1 5 10 15

Pro Val Ala Leu Glu Glu Tyr Ala Asn Ser Leu Glu Asp Arg Ala Val
20 25 30

Gly Val Thr Ser Thr Asp Phe Thr Asn Phe Lys Phe Tyr Ile Gln His
35 40 45

Gly Ala Ala Ala Tyr Cys Asn Ser Gly Thr Ala Ala Gly Ala Lys Ile
50 55 60

Thr Cys Ser Asn Asn Gly Cys Pro Thr Ile Glu Ser Asn Gly Val Thr
65 70 75 80

Val Val Ala Ser Phe Thr Gly Ser Lys Thr Gly Ile Gly Gly Tyr Val
85 90 95

```
Ser Thr Asp Ser Ser Arg Lys Glu Ile Val Val Ala Ile Arg Gly Ser
            100                 105                 110

Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Ala Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Arg Ser Tyr Arg Ser Ala Glu Ser Ile Asp Met Arg Ala Thr Met Thr
305                 310                 315                 320

Asp Ala Gln Leu Glu Ala Lys Leu Asn Ser Tyr Val Ala Met Asp Gln
                325                 330                 335

Glu Tyr Val Lys Thr His Gln Asn Arg Thr
            340                 345


<210> SEQ ID NO 42
<211> LENGTH: 335
<212> TYPE: PRT
<213> ORGANISM: Artificial Sequence
<220> FEATURE:
<223> OTHER INFORMATION: Description of Artificial Sequence: Synthetic
      mutant lipolytic enzyme "mut 12"

<400> SEQUENCE: 42

Met Leu Leu Leu Ser Leu Leu Ser Ala Val Thr Leu Ala Val Ala Ser
1               5                   10                  15

Pro Val Ala Leu Glu Glu Tyr Ala Asn Ser Leu Glu Asp Arg Ala Val
            20                  25                  30

Gly Val Thr Ser Thr Asp Phe Thr Asn Phe Lys Phe Tyr Ile Gln His
        35                  40                  45

Gly Ala Ala Ala Tyr Cys Asn Ser Gly Thr Ala Ala Gly Ala Asn Ile
    50                  55                  60

Thr Cys Ser Asn Asn Gly Cys Pro Thr Ile Glu Ser Asn Asn Val Thr
65                  70                  75                  80

Val Val Ala Ser Phe Thr Gly Ser Lys Thr Gly Ile Gly Gly Tyr Val
                85                  90                  95

Ser Thr Asp Ser Ser Arg Lys Glu Ile Val Val Ala Ile Arg Gly Ser
            100                 105                 110
```

-continued

```
Ser Asn Ile Arg Asn Trp Leu Thr Asn Leu Asp Phe Asp Gln Ser Asp
        115                 120                 125

Cys Ser Leu Val Ser Gly Cys Gly Val His Ser Gly Phe Gln Asn Ala
    130                 135                 140

Trp Ala Glu Ile Ser Ala Gln Ala Ser Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ser Ala Ala Asn Leu Arg Ala Asn Gly Thr
            180                 185                 190

Pro Val Asp Ile Tyr Thr Tyr Gly Ala Pro Arg Val Gly Asn Ala Ala
        195                 200                 205

Leu Ser Ala Phe Ile Ser Asn Gln Ala Gly Gly Glu Phe Arg Val Thr
    210                 215                 220

His Asp Lys Asp Pro Val Pro Arg Leu Pro Pro Leu Ile Phe Gly Tyr
225                 230                 235                 240

Arg His Thr Thr Pro Glu Tyr Trp Leu Ser Gly Gly Gly Gly Asp Lys
                245                 250                 255

Val Asp Tyr Ala Ile Ser Asp Val Lys Val Cys Glu Gly Ala Ala Asn
            260                 265                 270

Leu Met Cys Asn Gly Gly Thr Leu Gly Leu Asp Ile Asp Ala His Leu
        275                 280                 285

His Tyr Phe Gln Ala Thr Asp Ala Cys Asn Ala Gly Gly Phe Ser Trp
    290                 295                 300

Asn Ser Thr Met Thr Asp Ala Gln Leu Glu Ala Lys Leu Asn Ser Tyr
305                 310                 315                 320

Val Ala Met Asp Gln Glu Tyr Val Lys Thr His Gln Asn Arg Thr
                325                 330                 335


<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 43

His His His His His His
1               5
```

VARIANT LIPOLYTIC ENZYMES AND METHODS FOR EXPRESSION THEREOF

RELATED APPLICATIONS AND INCORPORATION BY REFERENCE

This application is a continuation-in-part application of international patent application Serial No. PCT/IB2010/52868 filed Jun. 23, 2010, which published as PCT Publication No. WO 2010/150213 on Dec. 29, 2010, which claims benefit of U.S. provisional patent application Ser. No. 61/220,288 filed Jun. 25, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jun. 24, 2014, is named 43049.01.2090_SL.txt and is 79,734 bytes in size.

FIELD OF THE INVENTION

The present invention relates to novel (variant) lipolytic enzymes and to one or more polynucleotides encoding one or more novel lipolytic enzymes. The invention also relates to methods of producing lipolytic enzymes, and uses thereof. The present invention further relates to the preparation of an improved foodstuff, in particular to the preparation of improved bakery products. Specifically, the invention provides lipolytic enzymes, which enzymes are capable of conferring improved characteristics to food products, including bakery products.

TECHNICAL BACKGROUND

The beneficial use of lipolytic enzymes (E.C. 3.1.1.x) in food and/or feed industrial applications has been known for many years.

For instance, in EP 0 585 988 it is claimed that lipase addition to dough resulted in an improvement in the antistaling effect. It is suggested that a lipase obtained from *Rhizopus arrhizus* when added to dough can improve the quality of the resultant bread when used in combination with shortening/fat. WO94/04035 teaches that an improved bread softness can be obtained by adding a lipase to dough without the addition of any additional fat/oil to the dough. Castello, P. ESEGP 89-10 Dec. 1999 Helsinki, shows that exogenous lipases can modify bread volume.

The substrate for lipases in wheat flour is 1.5-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

Lipolytic enzymes hydrolyse one or more of the fatty acids from lipids present in the food which can result in the formation of powerful emulsifier molecules within the foodstuff which provide commercially valuable functionality. The molecules which contribute the most significant emulsifier characteristics are the partial hydrolysis products, such as lysophospholipids, lyso-glycolipids and mono-glyceride molecules. The polar lipid hydrolysis products, namely lysophospholipids and lyso-glycolipids, are particularly advantageous. In bread making, such in situ derived emulsifiers can give equivalent functionality as added emulsifiers, such as DATEM.

However, the activity of lipolytic enzymes has also been found to result in accumulation of free fatty acids, which can lead to detrimental functionality in the foodstuff. This inherent activity of lipolytic enzymes limits their functionality.

The negative effect on bread volume is often explained by overdosing. Overdosing can lead to a decrease in gluten elasticity which results in a dough which is too stiff and thus results in reduced volumes. In addition, or alternatively, such lipases can degrade shortening, oil or milk fat added to the dough, resulting in off-flavour in the dough and baked product. Overdosing and off-flavour have been attributed to the accumulation of free fatty acids in the dough, particularly short chain fatty acids.

The presence of high levels of free fatty acids (FFA) in raw materials or food products is generally recognised as a quality defect and food processors and customers will usually include a maximum FFA level in the food specifications. The resulting effects of excess FFA levels can be in organoleptic and/or functional defects.

In WO2005/087918 novel fungal lipolytic enzymes were identified from *Fusarium* species, such as *Fusarium heterosporum* CBS 782.83 which were shown to have a superior quality in certain applications. These enzymes were expressed in *Hansenula polymorpha* and were found to hydrolyse primarily fatty acids in the sn-1 position of galactolipids and phospholipids in dough.

The problem with some fungal lipolytic enzymes is that expression of the enzyme may be limited and therefore may be costly to produce. For example expression of the enzyme in high amounts suitable for commercial scale activities may be limited. The industry is interested in finding novel lipolytic enzymes which show enhanced expression, particularly if this can be achieved without compromising functionality and/or activity.

Citation or identification of any document in this application is not an admission that such document is available as prior art to the present invention.

SUMMARY OF THE INVENTION

It has surprisingly been found that the new variant lipolytic enzymes of the present invention show increased expression compared with the wild type enzyme(s) from which they were prepared. Notably the increased expression is achieved without compromising the enzymes functionality and/or activity and/or application performance. In addition the new variant lipolytic enzymes may show improved functionality and/or activity compared with the wild type enzyme(s).

The inventors have found that by modifying (substituting or inserting) one or more surface amino acids located in an external loop(s) distal to the active site (catalytic triad) of the lipolytic enzyme to replace the surface amino acid with an amino acid which is more hydrophilic (compared with the original amino acid) or to introduce hydrophilic amino acids or to introduce a glycosylation site then it is possible to substantially and surprisingly increase the expression and/or functionality and/or activity of the variant enzyme compared with the wild type enzyme. Preferably, the surface amino acid is replaced with an Asn, Ser and/or Thr (or a combination thereof) for the purpose of introducing one or more glycosylation sites. Alternatively or in addition, an external loop(s) distal to the active site can be modified by inserting one or more amino acids selected from Asn, Ser and/or Thr to introduce one or more glycosylation sites. Lipolytic enzymes typically work in an interphase between fat and water (i.e. between a hydrophilic environment and a hydrophobic environment) and hence the performance of lipolytic enzymes in certain applications is very dependent upon this interphase as well as water activity. Without wishing to be bound by theory, by changing the hydrophilicity of the surface of the lipolytic enzyme at a position which is remote the active site of the enzyme (i.e. in the loops distal the active site of the enzyme) it is possible to control the orientation of the enzyme within the fat/water interphase, such that the active site is orientated towards the substrate for the enzyme, i.e. the fat. Thus it is possible to modify the lipolytic enzyme to optimally orientate the enzyme in the interphase to increase the activity of the enzyme. In addition, or alternatively, by introducing glycosylation sites it may be possible to enhance the folding and expression and/or secretion of the enzyme from a host organism, thus enhancing expression of the variant enzymes.

In addition to or alternatively, the present inventors have also found a number of specific modifications which surprisingly increase expression and/or functionality and/or activity of the lipolytic enzyme substantially. These may include addition of glycosylation sites and/or stabilisation of the C-terminus region of the enzyme. In some embodiments the specific modifications increase expression without comprising the functionality and/or activity of the lipolytic enzyme. Hence some of the specific modifications increase expression without compromising application performance of the variant enzymes compared with the wild-type (KLM1) enzyme the propresequence of which is shown herein as SEQ ID No. 2 (the mature form of which is amino acids 31-305 of SEQ ID No. 2).

Therefore in one aspect of the present invention there is provided a method for preparing a variant lipolytic enzyme comprising expressing in a host organism a nucleotide sequence which has at least 90% identity with a nucleotide sequence encoding a fungal lipolytic enzyme or which differs from a nucleotide sequence encoding a fungal lipolytic enzyme by one or several nucleic acid additions, deletions or substitutions and comprises at least one modification at a position which corresponds in the encoded amino acid sequence to a) the introduction of at least one glycosylation site (or one additional glycosylation site) in the amino acid sequence compared with the original fungal lipolytic enzyme; b) the introduction of at least one amino acid at a surface position on the polypeptide and at a location in an external loop distal to the active site (catalytic triad) of the enzyme which is more hydrophilic (compared with the original amino acid); or c) a substitution or insertion at one or more of positions 33, 63, 78, 190, 305, 306 or 320 or a deletion at one or more positions 311-312 or 307-319, wherein each amino acid position corresponds to the position of the amino acid sequence when aligned with SEQ ID No. 2; wherein when the nucleotide sequence has at least 90% identity with a nucleotide sequence encoding the fungal lipolytic enzyme shown in SEQ ID No. 22 or SEQ ID No. 23, or differs by one or several nucleic acid additions, deletions or substitutions from a nucleotide sequence encoding the fungal lipolytic enzyme shown in SEQ ID No. 22 or SEQ ID No. 23, the modification is not a substitution at position 63 and the deletion is not at position 311-312 (wherein the amino acid position numbering is that shown in respect of SEQ ID No. 2 when aligned).

The method may introduce at least one amino acid at a surface position on the polypeptide by substituting or inserting one or more amino acids at the surface position wherein the substitution or insertion is with an amino acid which is more hydrophilic (compared with the original amino acid).

In another embodiment the present invention provides a method of producing a variant lipolytic enzyme comprising expressing in a host organism a nucleotide sequence which has at least 90% identity with SEQ ID No. 1 or which differs from SEQ ID No. 1 by one or several nucleic acid additions, deletions or substitutions, and comprises at least one modification at a position which corresponds in the encoded amino acid sequence to a) the introduction of at least one glycosylation site in the amino acid sequence; b) the introduction of at least one hydrophilic amino acid at a surface position on the polypeptide and at a location in an external loop distal to the active site (catalytic triad) of the enzyme; or c) a substitution or insertion at one or more of positions 33, 63, 78, 190, 305, 306 or 320 or a deletion at one or more positions 311-312 or 307-319, wherein each amino acid position corresponds to the position of the amino acid sequence of SEQ ID No. 2.

The present invention further provides a method of producing a lipolytic enzyme comprising expressing in a host organism a nucleotide sequence comprising SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleotide sequence having at least 98% (preferably at least 99%, suitably at least 99.5% such as at least 99.8%) identity therewith; or a nucleic acid which differs by one or several nucleotide additions, deletions or substitutions from or which is related to the nucleotide sequence of SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26 by the degeneration of the genetic code.

There is also provided a method of preparing a lipolytic enzyme the method comprising transforming a host cell with a recombinant nucleic acid coding for a polypeptide having hydrolytic activity towards an ester bond in a polar lipid, which nucleic acid comprises a nucleotide sequence comprising SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleotide sequence having at least 98% (preferably at least 99%, suitably at least 99.5% such as at least 99.8%) identity with SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 or SEQ ID No. 26; or a nucleic acid which differs by one or several nucleotide additions, deletions or substitutions from or which is related to the nucleotide sequence of SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26 by the degeneration of the genetic code, the host cell being capable of expressing the nucleotide sequence coding for the polypeptide, cultivating the transformed host cell under conditions where the nucleic acid is expressed and harvesting the lipolytic enzyme.

The present invention provides an enhanced expression of the nucleic acids according to the present invention and thus an improved method of production of variant polypeptides.

In a further aspect the present invention provides a polypeptide (prepro-polypeptide or mature lipolytic enzyme) obtained by the method according to the present invention.

In a yet further aspect there is provided a nucleic acid comprising a nucleotide sequence encoding a lipolytic enzyme and which nucleotide sequence comprises at least one modification at a position which corresponds in the encoded amino acid sequence to a) the introduction of at least one glycosylation site in the amino acid sequence; b) the introduction of at least one hydrophilic amino acid at a surface position on the polypeptide and at a location in an external loop distal to the active site (catalytic triad) of the enzyme; or c) a substitution or insertion at one or more of positions 33, 63, 78, 190, 305, 306 or 320 or a deletion at one or more positions 311-312 or 307-319, wherein each amino acid position corresponds to the position of the amino acid sequence of SEQ ID No. 2, wherein when the nucleotide sequence encodes the fungal lipolytic enzyme shown as SEQ ID No. 22 or SEQ ID No. 23 the modification is not a substitution at position 63 and the deletion is not at position 311-312 (wherein the amino acid position numbering is that shown in respect of SEQ ID No. 2 when aligned).

In a further aspect the present invention provides a nucleic acid comprising a nucleotide sequence which has at least 90% identity with SEQ ID No. 1, or which differs from SEQ ID No. 1 by one or several nucleotide additions, deletions or substitutions, and which nucleotide sequence comprises at least one modification at a position which corresponds in the encoded amino acid sequence to a) the introduction of at least one glycosylation site in the amino acid sequence; b) the introduction of at least one hydrophilic amino acid at a surface position on the polypeptide and at a location in an external loop distal to the active site (catalytic triad) of the enzyme; or c) a substitution or insertion at one or more of positions 33, 63, 78, 190, 305, 306 or 320 or a deletion at one or more positions 311-312 or 307-319, wherein each amino acid position corresponds to the position of the amino acid sequence of SEQ ID No. 2

The present invention further provides a nucleotide sequence encoding a polypeptide having hydrolytic activity towards an ester bond in a polar lipid which nucleotide sequence comprises SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleotide sequence having at least 98% (preferably at least 99%, preferably at least 99.5%, such as at least 99.8%) identity with SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleic acid which differs by one or several nucleotide additions, deletions or substitutions from or which is related to the nucleotide sequence of SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20 or SEQ ID No. 26 by the degeneration of the genetic code.

In one embodiment the preferred nucleotide sequence is that shown in SEQ ID No. 8 (mutant 5) or a nucleotide sequence which is related to SEQ ID No. 8 by the degeneration of the genetic code.

In a further aspect the present invention provides a variant polypeptide encoded by the nucleic acid or nucleotide sequence according to the present invention.

Another aspect of the present invention provides a variant polypeptide which has hydrolytic activity towards an ester bond in a polar lipid and comprises an amino acid sequence which has at least 90% identity with amino acids 33-296 of SEQ ID No. 2, or differs by one or several amino acid additions, deletions or substitutions from amino acids 33-296 of SEQ ID No. 2, and which has been modified compared with the sequence shown in SEQ ID No. 2 to a) introduce at least one glycosylation site in the amino acid sequence; b) introduce at least one hydrophilic amino acid at a surface position on the polypeptide and at a location in an external loop distal to the active site (catalytic triad) of the enzyme; or c) substitute or insert an amino acid at least one or more of positions 33, 63, 78 or 190 wherein each amino acid position corresponds to the position of the amino acid sequence shown in SEQ ID No. 2.

In another aspect the present invention provides a polypeptide which has hydrolytic activity towards an ester bond in a polar lipid and comprises an amino acid sequence shown as amino acids 33-296 (or amino acids 31-305) of SEQ ID No. 5, SEQ ID No. 7, SEQ ID No. 9, SEQ ID No. 11, SEQ ID No. 13, SEQ ID No. 17, SEQ ID No. 19, SEQ ID No. 21 or SEQ ID No. 25.

In a yet further aspect the present invention provides a prepro-polypeptide which when post-translationally processed in a host organism produces a polypeptide which has hydrolytic activity towards an ester bond in a polar lipid, wherein the prepropolypeptide comprises an amino acid sequence shown as SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25.

In one aspect the present invention further provides a polypeptide which has hydrolytic activity towards an ester bond in a polar lipid, which polypeptide is obtainable from a prepro-polypeptide comprising an amino acid sequence shown as SEQ ID No. 9, SEQ ID No. 7, SEQ ID No. 5, SEQ ID No. 11, SEQ ID No. 13, SEQ ID No. 15, SEQ ID No. 17, SEQ ID No. 19 SEQ ID No. 21 or SEQ ID No. 25.

Depending on the host organism prepro-sequences often go through post-translational modification. With the present enzymes it is relatively common for the organism to remove the N-terminal region of the prepro sequence, i.e. remove all or part of the amino acids 1-30 of SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25. In some embodiments the host organism may remove slightly more amino acids than those shown as amino acids 1-30 of SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25, such as removing amino acids 1-31 or 1-32 or 1-33 for instance. In some instances the host organism may introduce an alternative N-terminal sequence which may encompass all or part of the amino acids shown as amino acids 1-30 or may comprise a completely different N-terminal sequence (such as EAEA or EA for instance). In some cases the mature enzyme produced from the prepro-sequence by the host organism may be a heterogen at its N-terminus end. In some embodiments the post-translational modification may mean modification in the C-terminal region of the prepro sequence. For example, all or part of the amino acids 306-348 may be removed from SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25 in the mature form. In some embodiments the host organism may remove slightly more amino acids than those shown as amino acids 306-348 of SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25, such as removing amino acids 305-348 or 304-348 or 303-348 for instance. In some cases the mature enzyme produced from the prepro-sequence by the host organism may be a heterogen at its C-terminus end. It is envisaged that the present invention encompasses all mature forms of the protein obtainable from a prepro-polypeptide comprising an amino acid sequence shown as SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 or SEQ ID No. 25, particularly those obtained from the host organism *Trichoderma reesei.*

The present invention yet further provides the use of a nucleic acid according to the present invention to enhance expression of a lipolytic enzyme from a host organism. Suitably the host organism may be a fungi, preferably *Trichoderma* spp., preferably *Trichoderma reesei*. Suitably the expression is enhanced between about 2-fold up to about 25-fold compared with the wild type nucleic acid (i.e. the nucleic acid without any modifications in accordance with the present invention).

The present invention further provides a method of making a foodstuff comprising adding a polypeptide according to the present invention to one or more ingredients of the foodstuff.

In another aspect the present invention provides a method of making a baked product comprising adding a polypeptide according to the present invention to a dough and baking the dough to make the baked product.

The present invention further provides a method of preparing a lyso-phospholipid comprising treating a phospholipid with a polypeptide according to the present invention to produce the lyso-phospholipid.

In a yet further embodiment the present invention provides a method of preparing a lyso-glycolipid comprising treating a glycolipid with a polypeptide according to the present invention to produce a lyso-glycolipid.

The present invention further provides a process of enzymatic degumming of vegetable or edible oils, comprising treating the edible or vegetable oil with a polypeptide according to the present invention so as to hydrolyse a major part of the polar lipids present therein.

In another aspect the present invention provides a foodstuff or a baked product obtained by the method of the present invention.

Aspects of the present invention are presented in the claims and in the following commentary.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequence for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

For the ease of reference, these and further aspects of the present invention are now discussed under appropriate section headings. However, the teachings under each section are not necessarily limited to each particular section.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DISCLOSURE OF INVENTION

All reference to amino acid positions as used herein is made by reference to the amino acid sequence SEQ ID No. 2. In other words, when the numbering of an amino acid position is considered this can be determined by alignment of the amino acid sequence with SEQ ID No. 2 and by referring to the position numbering of the aligned sequences using SEQ ID No. 2 as the reference sequence (see for example FIG. 22 which shows an alignment of SEQ ID No. 2 (designated therein as KLM1) with other sequences taught herein).

Suitably, the host organism used in accordance with the present invention may be a fungi, preferably from the genus *Trichoderma*, more preferably from the species *Trichoderma reesei.*

In one embodiment the fungal lipolytic enzyme before modification does not comprise any glycosylation sites. In other words, the methods of the present invention may be used to introduce at least one glycosylation site into a lipolytic enzyme which originally or naturally does not contain any glycosylation sites Suitably the variant polypeptide of the present invention may comprise at least two, suitably at least three, glycosylation sites.

Preferably the nucleotide sequence of the present invention or used in the methods of the present invention has at least 90% identity (preferably at least 95%, more preferably at least 98%, suitably at least 99%, such as at least 99.5% identity) with SEQ ID No. 1 or with SEQ ID No. 24, or with a nucleotide sequence shown in positions 23-106 of SEQ ID No. 24, or with a nucleotide sequence shown in positions 113-1063 of SEQ ID No. 24 or with a nucleotide sequence shown in positions 113-929 of SEQ ID No 24 except that it comprises at least one modification compared with SEQ ID No. 1 or with SEQ ID No. 24, or with a nucleotide sequence shown in positions 23-106 of SEQ ID No. 24, or with a nucleotide sequence shown in positions 113-1063 of SEQ ID No. 24 or with a nucleotide sequence shown in positions 113-929 of SEQ ID No. 24 respectively or with a nucleotide sequence which differs from one of the recited sequences by one or several nucleotide additions, deletions or substitutions.

In one embodiment when the nucleotide sequence has at least 90% identity with nucleotide sequence encoding the fungal lipolytic enzyme shown in SEQ ID No. 22 or SEQ ID No. 23, or which differs from a nucleotide sequence encoding the fungal lipolytic enzyme shown in SEQ ID No. 22 or SEQ ID No. 23 by one or several nucleotide additions, deletions or substitutions, then the modification is not a substitution at position 63 (e.g. it is not the substation K63N) and the deletion is not at position 311-312. The nucleotide sequence encoding the fungal lipolytic enzyme shown in SEQ ID No. 22 or SEQ ID No. 23 is shown herein as SEQ ID No 24 or a portion thereof (such as a nucleotide sequence shown in positions 23-106 of SEQ ID No. 24, or a nucleotide sequence shown in positions 113-1063 of SEQ ID No. 24 or a nucleotide sequence shown in positions 113-929 of SEQ ID No. 24.

In one embodiment preferably the modification in accordance with the present invention corresponds with the introduction of at least one glycosylation site at a surface position on the polypeptide and at a location in an external loop distal to the active site of the enzyme.

Preferably the nucleotide sequence is modified such that one or more amino acids located at a surface position on the polypeptide and at a location in an external loop which is distal to the active site of the enzyme is substituted with an amino acid which is more hydrophilic than the original amino acid.

Alternatively, the nucleotide sequence may be modified such that one or more hydrophilic amino acids are inserted at a surface position on the polypeptide and at a location in the external loop distal to the active site of the enzyme.

In one preferable embodiment the nucleotide sequence is modified such that in the encoded amino acid one or more amino acids are substituted or inserted to provide one or more consensus sequences Asn-Xxx-Ser or Asn-Xxx-Thr, where Xxx could be any amino acid except Pro.

In one embodiment the nucleotide sequence is modified such that in the encoded amino acid sequence one or more Asn, Ser or Thr are introduced. In other words the nucleotide sequence according to the present invention comprises a modification corresponding with the introduction of one or more of Asn, Ser or Thr into the encoded protein.

Suitably in the method or nucleic acid of the present invention least two, suitably at least three, glycosylation sites may be introduced.

The nucleotide sequence of the present invention and in the methods of the present invention may be further modified to enhance C-terminal processing of the protein compared with the original lipolytic enzyme, for example compared with a lipolytic enzyme comprising SEQ ID No. 2 or amino acids 33-296 (or 31-305) thereof.

Suitably, the nucleotide sequence or the polypeptide may include C-terminal processing, preferably to render the polypeptide more stable.

In the present case C-terminus of the polypeptide is considered to be from amino acid position 306 onwards, wherein said position corresponds to the position in the amino acid sequence of SEQ ID No. 2 when aligned.

Suitably the C-terminal processing as taught in the present invention comprises one or more of the following: a substitution or insertion at positions 306 or 320 or a deletion at one or more KEX2 positions in the C-terminus, wherein each position corresponds to the position of the amino acid sequence of SEQ ID No. 2. Suitably the C-terminal processing may comprise removal of at least one of the C-terminal KEX2 sites. Without wishing to be bound by theory it is thought that removal of the KEX2 site causes cessation or a decrease in the rate of proteolytic processing and improved stability of the enzyme without compromising its activity. One KEX2 site may be found at position 306 (when aligned with SEQ ID No. 2). Another KEX2 site may be found at positions 311-312 (when aligned with SEQ ID No. 2).

Preferably, nucleotide sequence according to the present invention or for use in the present invention is modified such that there is a substitution at one or more of positions 33, 63, 78, 190 and 305, wherein the amino acid is substituted with N.

Suitably the nucleotide sequence according to the present invention or for use in the present invention may be modified such that there is a substitution at one or more of positions 63, 78, 190 and 305, wherein the amino acid is substituted with N.

In one embodiment the nucleotide sequence according to the present invention or for use in the present invention may be modified such that a glycosylation site is introduced at positions 190, 191 and 192 (such that the glycosylation site comprises the consensus sequence Asn-Xxx-Ser or Asn-Xxx-Thr, where Xxx is any amino acid except Pro).

In another embodiment the nucleotide sequence according to the present invention or for use in the present invention may be modified such that a glycosylation site is introduced at positions 33, 34 and 35 (such that the glycosylation site comprises the consensus sequence Asn-Xxx-Ser or Asn-Xxx-Thr, where Xxx is any amino acid except Pro).

In another embodiment the nucleotide sequence according to the present invention or for use in the present invention may be modified such that a glycosylation site is introduced at positions 63, 64 and 65 (such that the glycosylation site comprises the consensus sequence Asn-Xxx-Ser or Asn-Xxx-Thr, where Xxx is any amino acid except Pro).

In another embodiment the nucleotide sequence according to the present invention or for use in the present invention may be modified such that a glycosylation site is introduced at positions 78, 79 and 80 (such that the glycosylation site comprises the consensus sequence Asn-Xxx-Ser or Asn-Xxx-Thr, where Xxx is any amino acid except Pro).

The glycosyolation site may be introduced by modifying (e.g. inserting or substituting) a single amino acid. Alternatively more than one amino acid (e.g. 2 or 3 amino acids) may be modified (e.g. inserted or substituted) in order to introduce the glycosylation site.

Suitably, the nucleotide sequence according to the present invention or for use in the present invention may be modified such that there is a substitution at position 190, wherein the amino acid is substituted with N.

In one embodiment preferably the nucleotide sequence according to the present invention comprises the whole or part of the nucleotide sequence shown here as SEQ ID No. 8 (or a nucleotide sequence which is related to SEQ ID No. 8 by the degeneration of the genetic code). The present invention yet further provides a polypeptide encoded by this nucleotide sequence.

In one embodiment the variant polypeptide of the present invention or for use in the present invention comprises an amino acid sequence as shown in amino acids 33-296 (or 31-304 or 31-305) of SEQ ID No. 9.

Suitably, the nucleotide sequence according to the present invention or for use in the present invention may be modified such that there is a substitution at position 306, wherein the amino acid is substituted with any amino acid other than K or R or A, preferably the substitution at position 306 is with amino acid S.

Suitably, the nucleotide sequence according to the present invention or for use in the present invention may be modified such that there is a substitution at position 320, wherein the amino acid is substituted with any amino acid other than T, preferably the substitution at position 320 is with amino acid E.

The variant polypeptide according to the present invention or encoded by the nucleic acid of the present invention or produced by a method of the present invention preferably has phospholipase activity or galactolipase activity.

In some embodiments preferably the modifications made to the variant polypeptide or the nucleic acid encoding same are modifications which add at least one glycosylation site (or multiple glycosylation sites) to the variant polypeptide and/or relate to C-terminal processing, such as to stabilise the C-terminus of the variant polypeptide.

Suitably the polypeptide may comprise a substitution at one or more of positions 33, 63, 78, 190, suitably 63, 78 or 190. Suitably the substitution may be with N.

In one embodiment the variant polypeptide according to the present invention may comprises at least one substitution at position 306. Preferably the substitution at position 306 is with any amino acid other than K or R. Preferably the substitution at position 306 is with any amino acid other than K or R or A. In one embodiment the substitution at position 306 is preferably with a non-charged and/or hydrophilic amino acid. Suitably the substation at position 306 may be with amino acid S.

In one embodiment, the nucleotide sequence according to the present invention or for use in the present invention may be modified such that positions which may be modified in the encoded amino acid sequences are as follows:

R306S + G33N;
R306S + K63N;
R306S + G78N;
R306S + A190N;
R306S + K63N + G78N + A190N;
R306S + ΔKR311-312;
R306S + K63N + G78N + A190N + Δ311-312;
R306S + K63N + G78N + A190N + Δ307-319;
R306S + K63N + G78N + A190N + Δ307-319 + T320E; or
R306S + K63N + G78N + A190N + Δ307-319 + R305N

As one skilled in the art will readily appreciate when the backbone is not KLM1 wt (shown herein as SEQ ID No. 2) then the amino acid shown in the table as the starting amino acid may vary in the alternative backbone at the same position when aligned with SEQ ID No. 2.

For the avoidance of doubt the symbol "A" as used herein means deletion of those amino acids listed after the symbol.

In some embodiments, the introduction of at least one amino acid at a surface position on the polypeptide and at a location in an external loop distal to the active site (catalytic triad) of the enzyme which is more hydrophilic (compared with the original amino acid) is preferably by the introduction of at least one glycosylation site (or one additional glycosylation site) at a surface position on the polypeptide and at a location in an external loop distal to the active site (catalytic triad) of the enzyme. In other words adding a glycosylation site renders the enzyme more hydrophilic in the region where the glycosylation site has been added.

In another aspect the present invention provides the use of a variant polypeptide enzyme according to the present invention in the manufacture of a foodstuff, such as for instance a dough, a baked product, an egg, an egg-based product, a noodle product, a cheese product, a tortilla product, an animal feed product, a vegetable oil or an edible oil. Advantageously, the addition of an enzyme of the present invention to the foodstuff may lead to improved emulsification with lower accumulation of free fatty acids.

In a further aspect the present invention provides the use of variant polypeptide enzyme according to the present invention in the manufacture of a dough and/or a baked product, comprising adding said lipolytic enzyme to a dough, and (optionally) baking the dough to make a baked product for one or more of the following: reducing stickiness of the dough; improving machinability of the dough; reducing blistering during baking of the baked product; improving bread volume and/or softness; prolonging shelf life of the baked product and/or dough; improving antistaling effect of the baked product and/or dough; improving crumb structure of the baked product; reducing pore heterogeneity of the baked product; improving pore homogeneity of the baked product; reducing mean pore size of the baked product; improving flavour and/or odour of the baked product, improving the colour of the crust of the baked product.

In a further aspect of the present invention provides the use of a variant polypeptide enzyme according to the present invention in the manufacture of egg-based products for improving texture, reducing mean particle size, reducing mean particle distribution, improving heat stability, improving microwave performance and/or stability.

In another aspect of the present invention, there is provided a method of treating egg or egg-based product, which method comprises adding a variant polypeptide enzyme according to the present invention to an egg or egg-based product.

In another aspect of the invention, there is provided a method of making noodles, or a noodle dough or a noodle-based product, which method comprises adding a variant polypeptide enzyme according to the present invention to the noodle, noodle dough or noodle-based product.

In one aspect of the present invention, there is provided a use of a variant polypeptide enzyme according to the present invention in the manufacture of a noodle or a noodle-based product for one or more of improving colour/yellowness, stabilising colour characteristics, reducing brightness, reducing fat content, improving texture and bite (chewiness), reducing water activity, reducing breakage, increasing core firmness and improving shape retention during processing In another aspect of the invention, there is provided a method of making a tortilla or tortilla dough, which method comprises adding a variant polypeptide enzyme according to the present invention to the tortilla or tortilla dough.

A further aspect of the present invention provides the use of a variant polypeptide enzyme according to the present invention in the manufacture of a tortilla or a tortilla dough for improving the rollability of a tortilla, increasing pliability of a tortilla, improving antistaling properties of the tortilla and/or tortilla dough, improving softness and/or reducing off-flavour in the tortilla and/or tortilla dough.

The functionality of the lipolytic enzyme in tortilla and/or noodles may be improved by combination with emulsifiers such as DATEM.

In another aspect of the invention, there is provided a method of treating milk, cheese milk, cheese or a cheese-based product, which method comprises adding a variant polypeptide enzyme according to the present invention to the cheese or cheese-based product.

The present invention yet further provides use of a variant polypeptide enzyme according to the present invention in the manufacture of a cheese or a cheese-based product for one or more of improving flavour, texture and/or stability, decreasing in the oiling-off effect in cheese and/or to increase cheese yield in cheese production.

In another aspect of the invention, there is provided a method of treating animal feed, which method comprises adding a variant polypeptide enzyme according to the present invention to the animal feed.

The present invention further provides the use of a variant polypeptide enzyme according to the present invention in the manufacture of animal feed for enhancing one or more of: feed utilisation and/or conversion efficiency, body weight gain, digestibility nitrogen uptake, metabolisability of dry matter and palatability.

In a further aspect of the present invention provides the use of a variant polypeptide enzyme according to the present invention in a process of preparing a lyso-phospholipid, for example lysolecithin by treatment of a phospholipid (e.g. lecithin) with the enzyme to produce the partial hydrolysis product, i.e. the lyso-phospholipid.

In another aspect of the present invention there is provided a process of preparing a lyso-phospholipid, for example lysolecithin, which process comprises treating a phospholipid (e.g. lecithin) with a variant polypeptide enzyme according to the present invention.

In a further aspect of the present invention provides the use of a variant polypeptide enzyme according to the present invention in a process of preparing a lyso-glycolipid, (for example digalactosyl monoglyceride (DGMG) or monogalactosyl monoglyceride (MGMG)) by treatment of a glycolipid (e.g. digalactosyl diglyceride (DGDG) or monogalactosyl diglyceride (MGDG)) with the lipolytic enzyme according to the present invention to produce the partial hydrolysis product, i.e. the lyso-glycolipid.

In a yet further aspect there is provided a process of preparing a lyso-glycolipid (for example digalactosyl monoglyceride (DGMG) or monogalactosyl monoglyceride (MGMG)), which process comprising treating a glycolipid (e.g. digalactosyl diglyceride (DGDG) or monogalactosyl diglyceride (MGDG)) with a variant polypeptide enzyme according to the present invention.

The present invention also provides a process of enzymatic degumming of vegetable or edible oils, comprising treating the edible or vegetable oil with a variant polypeptide enzyme according to the present invention so as to hydrolyse a major part of the polar lipids (e.g. phospholipid and/or glycolipid).

For the avoidance of doubt, a person of ordinary skill in the art would be aware of methodology suitable for carrying out the enzymatic treatment of edible oils (for instance see EP 0 869 167). Known method may suitably be used when carrying out the present invention, with the proviso that the known enzyme is replaced with the enzyme according to the present invention.

In a further aspect the present invention provides the use of a variant polypeptide enzyme according to the present invention in the manufacture of a vegetable oil or edible oil for reducing the amount phospholipid in the vegetable oil or edible oil whilst maintaining the triglyceride content of the oil and/or preventing or reducing the accumulation of free fatty acids.

In a yet further aspect the present invention provides the use of a variant polypeptide enzyme according to the present invention in a process comprising treatment of a phospholipid so as to hydrolyse fatty acyl groups.

In another aspect the present invention provides the use of a variant polypeptide enzyme according to the present invention in a process for reducing the content of a phospholipid in an edible oil, comprising treating the oil with the fungal lipolytic enzyme according to the present invention so as to hydrolyse a major part of the phospholipid, and separating an aqueous phase containing the hydrolysed phospholipid from the oil.

Preferably, the variant lipolytic enzyme according to the present invention hydrolyses polar lipids (e.g. glycolipids and/or phospholipids). In other words the variant lipolytic enzyme according to the present invention preferably has phospholipase activity (e.g. phospholipase A2 (E.C. 3.1.1.4) activity and/or phospholipase A1 (E.C. 3.1.1.32) activity) and/or galactolipase or glycolipase (E.C. 3.1.1.26) activity. The variant lipolytic enzyme according to the present invention may additionally hydrolyse triglycerides. In other words the variant lipolytic enzyme according to the present invention may additional have triglyceride lipase activity (E.C. 3.1.1.3).

The term "glycolipase activity" as used herein encompasses "galactolipase activity". The terms glycolipids and galactolipids may be used interchangeably herein and include hydrolysis of DGDG and MGDG, which are hydrolysed to DGMG or MGMG, respectively.

The term "polar lipids" as used herein means phospholipids and/or glycolipids. Preferably, the term "polar lipids" as used herein means both phospholipids and glycolipids.

Suitably the variant polypeptide according to the present invention may have phospholipase activity (e.g. phospholipase A2 (E.C. 3.1.1.4) activity and/or phospholipase A1 (E.C. 3.1.1.32) activity) and/or galactolipase or glycolipase (E.C. 3.1.1.26) activity.

The glycolipase activity, phospholipase activity and triacylglyceride lipase activity of an enzyme may be determined using the assays presented hereinbelow.

Determination of Galactolipase Activity (Glycolipase Activity Assay):

Substrate:

0.6% digalactosyldiglyceride (Sigma D 4651), 0.4% Triton-X 100 (Sigma X-100) and 5 mM $CaCl_2$ was dissolved in 0.05M HEPES buffer pH 7.

Assay Procedure:

400 μL substrate was added to an 1.5 mL Eppendorf tube and placed in an Eppendorf Thermomixer at 37° C. for 5 minutes. At time t=0 min, 50 μL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity GLU at pH 7 was calculated as micromoles of fatty acid produced per minute under assay conditions.

Determination of Phospholipase Activity (Phospholipase Activity Assay):

Phospholipase activity was measured using two different methods which give comparable results. Either of these methods can be used to determine phospholipase activity in accordance with the present invention. Preferably, the PLU assay is used for determining the phospholipase activity of any enzyme.

"PLU Assay" for Determination of Phospholipase Activity

Substrate:

0.6% L-α Phosphatidylcholine 95% Plant (Avanti #441601), 0.4% Triton-X 100 (Sigma X-100) and 5 mM $CaCl_2$ was dissolved in 0.05M HEPES buffer pH 7.

Assay Procedure:

400 μL substrate was added to an 1.5 mL Eppendorf tube and placed in an Eppendorf Thermomixer at 37° C. for 5 minutes. At time t=0 min, 50 μL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH. Enzyme activity PLU-7 at pH 7 was calculated as micromoles of fatty acid produced per minute under assay conditions "TIPU Assay" for Determination of Phospholipase Activity 1 TIPU (Titration Phospholipase Unit) is defined as the amount of enzyme, which liberates 1 μmol free fatty acid per minute at the assay conditions.

Phospholipase A1 and A2 catalyse the conversion of lecithin to lyso-lecithin with release of the free fatty acid from position 1 and 2, respectively. Phospholipase activity can be determined by continuous titration of the fatty acids liberated from lecithin during enzymation, since the consumption of alkali equals the amount of fatty acid liberated.

Substrate:

4% lecithin, 4% Triton-X 100, and 6 mM $CaCl_2$: 12 g lecithin powder (Avanti Polar Lipids #44160) and 12 g Triton-X 100 (Merck 108643) was dispersed in approx. 200 ml demineralised water during magnetic stifling. 3.0 ml 0.6 M $CaCl_2$ (p.a. Merck 1.02382) was added. The volume was adjusted to 300 mL with demineralised water and the emulsion was homogenised using an Ultra Thurax. The substrate was prepared freshly every day.

Assay Procedure:

An enzyme solution was prepared to give a slope on the titration curve between 0.06 and 0.18 ml/min with an addition of 300 μL enzyme.

A control sample of known activity is included.

The samples were dissolved in demineralised water and stirred for 15 min. at 300 rpm. 25.00 ml substrate was thermostatted to 37.0° C. for 10-15 minutes before pH was adjusted to 7.0 with 0.05 M NaOH. 300 μL enzyme solution was added to the substrate and the continuous titration with 0.05 M NaOH was carried out using a pH-Stat titrator (Phm 290, Mettler Toledo). Two activity determinations are made on each scaling.

After 8 minutes the titration is stopped and the slope of the titration curve is calculated between 5 and 7 minutes. The detection limit is 3 TIPU/ml enzyme solution.

Calculations:

The phospholipase activity (TIPU/g enzyme) was calculated in the following way:

$$TIPU/\mathrm{g} = \frac{\alpha \cdot N \cdot 10^6 \frac{\mu\mathrm{mol}}{\mathrm{mol}} \cdot 10^3 \frac{1}{\mathrm{ml}} \cdot V_1}{m \cdot V_2} = \frac{\alpha \cdot N \cdot 10^3 \cdot V_1}{m \cdot V_2}$$

Where:

α is the slope of the titration curve between 5 and 7 minutes of reaction time (ml/min)

N is the normality of the NaOH used (mol/l)

V1 is the volume in which the enzyme is dissolved (ml)

m is the amount of enzyme added to V1 (g)

V2 is the volume of enzyme solution added to the substrate (ml)

Determination of Triacylglyceride Lipase Activity: Assay Based on Triglyceride (Tributyrin) as Substrate (LIPU):

Lipase activity based on tributyrin is measured according to Food Chemical Codex, Forth Edition, National Academy Press, 1996, p 803, with the modifications that the sample is dissolved in deionized water instead of glycine buffer, and the pH stat set point is 5.5 instead of 7.

1 LIPU is defined as the quantity of enzyme which can liberate 1 mol butyric acid per minute under assay conditions.

The term "variant" as used herein means a protein which is not found in nature. Typically, the variant polypeptide may be produced by modifying a naturally occurring polypeptide (or nucleotide sequence encoding same). The variant polypeptide therefore comprises one or more amino acid alterations (i.e. amino acid deletions, additions or substitutions) when compared with the natural or wild-type sequence.

Preferably, the variant polypeptide according to the present invention is obtained from a fungal lipolytic enzyme obtainable (preferably obtained) from a filamentous fungus. More preferably, the fungal lipolytic enzyme is obtainable (preferably obtained) from *Fusarium* spp. Preferably, the fungal lipolytic enzyme according to the present invention may be obtainable (preferably obtained) from *Fusarium heterosporum* or *Fusarium oxysporum*. Suitably, the fungal lipolytic enzyme according to the present invention may be obtainable (preferably obtained) from *Fusarium heterosporum* (CBS 782.83) or *Fusarium oxysporum* (taught in WO98/26057 or U.S. Pat. No. 7,465,570).

In one embodiment preferably the modification is not K63N, particularly when the backbone is from *Fusarium oxysporum*.

Thus in one aspect, preferably the lipolytic enzyme and the variant polypeptide according to the present invention is a fungal lipolytic enzyme, preferably a filamentous fungal lipolytic enzyme.

Preferably, the fungal lipolytic enzyme or variant polypeptide according to the present invention is not a fusion protein comprising an amino acid sequence from a *Thermomyces* protein or part thereof fused with an amino acid sequence from a *Fusarium* protein or part thereof. In particular, preferably the fungal lipolytic enzyme according to the present invention is not a fusion protein comprising an amino acid sequence from a *Thermomyces lanuginosa* protein or a part thereof fused with an amino acid sequence from a *Fusarium oxysporum* protein or part thereof.

Preferably, the fungal lipolytic enzyme according to the present invention is not obtained from *Thermomyces lanuginosa* and/or is not a variant of an enzyme obtained from *Thermomyces lanuginosa*.

The variant polypeptides of the present invention were tested in baking tests and compared with the lipolytic enzyme from *Fusarium heterosporum* CBS 782.83 (SEQ ID No. 2—which is the prepro-sequence with the mature sequence being amino acids 33-296 (suitably 31-304 or 31-305 depending on the host organism). This enzyme is also designated herein as KLM1 and constitutes the "wild-type" enzyme or backbone enzyme in respect of the variant polypeptides taught herein) with very good results.

The baking effects of the variant polypeptides were found to be superior to the fungal lipolytic enzyme from *F. heterosporum* CBS 782.83 (an enzyme comprising the amino acids sequence shown as amino acids 33-296 (suitably 31-304 or 31-305) of SEQ ID No. 2; KLM1).

Suitably, the term "foodstuff" as used herein means a substance which is suitable for human and/or animal consumption.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

In a preferred aspect the present invention provides a foodstuff as defined above wherein the foodstuff is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

In one aspect the foodstuff in accordance with the present invention may be a dough product or a baked product, such as a bread, a fried product, a snack, cakes, pies, brownies, cookies, noodles, instant noodles, tortillas, snack items such as crackers, graham crackers, pretzels, and potato chips, and pasta.

In another aspect, the foodstuff in accordance with the present invention may be an animal feed.

In one aspect preferably the foodstuff is selected from one or more of the following: eggs, egg-based products, including mayonnaise, salad dressings, sauces, ice cream, egg powder, modified egg yolk and products made therefrom.

In some of the applications mentioned herein, particularly the food applications, such as the bakery applications, the lipolytic enzyme according to the present invention may be used with one or more conventional emulsifiers, including for example monoglycerides, diacetyl tartaric acid esters of mono- and diglycerides of fatty acids, sodium stearoyl lactylate (SSL) and lecithins.

In addition or alternatively, the enzyme according to the present invention may be used with one or more other suitable food grade enzymes. Thus, it is within the scope of the present invention that, in addition to the lipolytic enzyme of the present invention, at least one further enzyme may be added to the baked product and/or the dough. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases, and acyltransferases (such as those described in WO04/064987 for instance).

It is particularly preferred that the lipolytic enzyme of the invention is used in combination with alpha amylases in producing food products. In particular, the amylase may be a non-maltogenic amylase, such as a polypeptide having non-maltogenic exoamylase activity, in particular, glucan 1,4-alpha-maltotetrahydrolase (EC 3.2.1.60) activity (as disclosed in WO05/003339). A suitable non-maltogenic amylase is commercially available as Powersoft™ (available from Danisco A/S, Denmark). Maltogenic amylases such as Novamyl™ (Novozymes A/S, Denmark) may also be used. In one embodiment, the combined use of alpha amylases and the lipolytic enzyme of the invention may be used in a dough, and/or the production of a baked product, such as bread, cakes, doughnuts, cake doughnuts or bagels. The combination of alpha amylases and the lipolytic enzyme of the invention is also considered as preferable for use in methods of production of tortillas, such as wheat and/or maize tortillas.

In another preferred embodiment, the lipolytic enzyme according to the present invention may be used in combination with a xylanase in producing food products. GRINDAMYL™ and POWERBake 7000 are examples of commercially available xylanase enzymes available from Danisco A/S. Other examples of xylanase enzymes may be found in WO03/020923 and WO01/42433

Preferably, the lipolytic enzyme according to the present invention may be used in combination with a xylanase and an alpha amylase. Suitably the alpha amylase may be a maltogenic, or a non-maltogenic alpha amylase (such as GRINDAMYL™ or POWERSoft, commercially available from Danisco A/S), or a combination thereof.

The lipolytic enzyme of the invention can also preferably be used in combination with an oxidising enzyme, such as a maltose oxidising enzyme (MOX), for example hexose oxidase (HOX). Suitable methods are described in WO03/099016. Commercially available maltose oxidising enzymes GRINDAMYL™ and SUREBake are available from Danisco A/S.

Optionally an alpha-amylase, such as a non-maltogenic exoamylase and/or a maltogenic amylases, and/or a maltose oxidising enzyme (MOX) in combination with the enzyme according to the present invention may be used in methods of preparing a dough, a baked product, tortilla, cake, instant noodle/fried snack food, or a dairy product such as cheese.

The lipolytic enzyme according to the present invention is typically included in the foodstuff or other composition by methods known in the art. Such methods include adding the lipolytic enzyme directly to the foodstuff or composition, addition of the lipolytic enzyme in combination with a stabilizer and/or carrier, and addition of a mixture comprising the lipolytic enzyme and a stabilizer and/or carrier.

Suitable stabilizers for use with the present invention include but is not limited to inorganic salts (such as NaCl, ammonium sulphate), sorbitol, emulsifiers and detergents (such as Tween 20, Tween 80, Panodan AB100 without triglycerides, polyglycerolester, sorbitanmonoleate), oil (such as rape seed oil, sunflower seed oil and soy oil), pectin, trehalose and glycerol.

Suitable carriers for use with the present invention include but is not limited to starch, ground wheat, wheat flour, NaCl and citrate.

Further preferable aspects are presented in the accompanying claims and the in the following description and examples.

Advantages

One advantage of the methods of the present invention, the nucleic acids of the present invention and the variant polypeptides of the present invention is that the expression of the nucleic acids in a commercial host species, e.g. *Trichoderma reesei*, is significantly improved compared with the wild-type enzyme (e.g. KLM 1; encoded by nucleotide sequence SEQ ID No. 1). This has the advantage that it is much cheaper to produce the variants. The increase in production is significant with the wild type in *T. reesei* being inefficiently produced, whereas the variants typically have an improved expression level. Typically the variants are expressed at levels between about 2 to about 25 times, preferably between about 6 times to about 25 times, higher than the wild type enzyme.

The variant enzymes of the present invention have surprisingly been found to have superior functionality when used in baking applications. The use of the variant lipolytic enzymes according to the present invention advantageously results in significantly improved properties to the dough and/or baked products compared with other lipolytic enzymes from fungi, particularly LipopanF™ and/or the wild type enzyme from *Fusarium heterosporum* (comprising the amino acid sequence shown herein as amino acids 33-296 (suitably 31-304 or 31-305) of SEQ ID No. 2 and taught in WO2005/087918).

Another advantage of the variant polypeptides of the present invention is their enhanced activity and/or functionality compared with the wild-type enzyme (e.g. KLM1, comprising the amino acid sequence shown herein as amino acids 33-296 (suitably 31-304 or 31-305) of SEQ ID No.2). This can lead to the "cost-in-use" of the enzyme being reduced. For example the proportion of the units that would be needed with the variant polypeptide in order to achieve the same results/effects compared with the wild-type enzyme would be significantly reduced. For instance, it is envisaged that the variant polypeptide can be dosed at about 25%-75%, preferably about 25%-50%, preferably about 25%, of the level of the wild-type enzyme(s).

The term "modifying" (or "modification") as used herein means substituting or inserting (or substitution or insertion).

Technical Effects

For baked products, such as bread, steam buns and US white pan bread, for example, the addition of a lipolytic enzyme of the present invention may result in one or more of the following: improved bread volume and softness, prolonged shelf life and/or an antistaling effect, improved crumb structure, reduced pore heterogeneity, reduced mean pore size, improved flavour and/or odour, and improved colour of the crust.

Advantageously, the enzyme according to the present invention may be used to replace emulsifiers in foodstuffs, such as dough and/or baked products.

The lipolytic enzyme according to the present invention may have synergy with emulsifiers such as DATEM, SSL, CSL, monoglyceride, polysorbates and Tween. Thus, the lipolytic enzyme according to the present invention may be used in combination with one or more emulsifiers. Advantageously, the use of the lipolytic enzyme according to the present invention in combination with one or more emulsifiers may reduce the overall amount of emulsifier used compared with the amount needed when no enzyme according to the present invention is used.

The lipolytic enzyme according to the present invention may also have synergy with hydrocolloids, Guar, xanthum and pectin, and with maltose oxidising enzymes such as hexose oxidase.

For doughnuts, cake doughnuts, bagels, snack cakes and muffins, for example, the use of a lipolytic enzyme of the present invention may result in a synergistic effect when used in combination with one or more of alpha-amylases, maltogenic alpha-amylase and non-maltogenic alpha-amylase.

For cakes, sponge cakes and palm cakes, for example, the use of the lipolytic enzyme of the present invention may result in a synergistic effect when used in combination with one or more of hydrocolloids such as Guar, and/or one or more emulsifiers such as DATEM.

For biscuits, for example, use of a lipolytic enzyme according to the present invention confers improved rollability and handling properties, particularly when cold (cold rollability).

Advantageously, in mayonnaise and other egg-based products, for example, use of a lipolytic enzyme according to the present invention may lead to improved texture, reduced mean particle size, and/or reduced mean particle distribution, improved heat stability, improved microwave performance and/or stability.

In cakes, use of the present invention advantageously leads to improved softness, volume, improved keeping properties and shelf life.

For noodles or noodle-products, e.g. instant noodles, for example, the lipolytic enzyme of the present invention may confer one or more of the following characteristics: improved colour/yellowness, more stable colour characteristics, reduced brightness, reduced fat content, improved texture and bite (chewiness), reduced water activity, reduced breakage, increased core firmness and improved shape retention during processing.

Preferably, the lipolytic enzyme of the present invention may be used to reduce the fat content of a noodle or a noodle product, for instance an instant noodle.

In tortilla, for example, use of the enzyme according to the present invention may result in one or more of the following: reduced rollability of the tortilla, for instance by increasing pliability, improved antistaling properties, improving softness and/or reducing off flavour.

Advantageously, improved rollability and/or pliability may lead to a reduced likelihood of the tortilla splitting when rolled.

In cheese and/or cheese-based products, for example, the use of the enzyme according to the present invention may result in one or more of the following: an improved flavour, texture and/or stability, a decrease in the oiling-off effect in cheese and/or an increase in cheese yield.

The term "oiling off effect" as used herein refers to the free oil released when cheese is melted.

The lipolytic enzyme according to the present invention may be used to produce a low fat cheese. Advantageously, the enzyme of the present invention may stabilise fat in milk and/or may enhance flavour.

In animal feed, for example, the enzyme according to the present invention advantageously may result in one or more the following: enhanced feed utilisation/conversion efficiency within the animal, improved body weight gain of the animal, improved digestibility of the feed, improved nitrogen uptake by the animal, e.g. from the feed, improved metabolisability of dry matter of the feed and improved palatability of feed.

Uses

The enzyme according to the present invention has many applications.

In particular, the variant polypeptides according to the present invention may be useful in the preparation of a foodstuff.

For example, the variant polypeptides according to the present invention may be particularly useful in the treatment of egg or egg-based products.

Treatment of egg or egg-based products with a fungal lipolytic enzyme according to the present invention can improve the stability, thermal stability under heat treatment such as pasteurisation and result in substantial thickening. Egg-based products may include, but are not limited to cakes, mayonnaise, salad dressings, sauces, ice creams and the like.

The fungal lipolytic enzymes according to the present invention are particularly useful in the preparation of baked products, such as those prepared from a dough, including breads, cakes, sweet dough products, laminated doughs, liquid batters, muffins, doughnuts, biscuits, crackers and cookies.

The fungal lipolytic enzymes according to the present invention may also be used in bread-improving additive, e.g. dough compositions, dough additive, dough conditioners, pre-mixes and similar preparations conventionally added to the flour and/or the dough during processes for making bread or other baked products to provide improved properties to the bread or other baked products.

Thus, the present invention further relates to a bread-improving composition and/or a dough-improving composition comprising a variant polypeptide according to the present invention; and also to a dough or baked product comprising such a bread-improving and/or dough-improving composition.

The bread-improving composition and/or dough-improving composition may comprise, in addition to a fungal lipolytic enzyme according to the present invention, other substances, which substances are conventionally used in baking to improve the properties of dough and/or baked products.

The bread-improving composition and/or dough-improving composition may comprise one or more conventional baking agents, such as one or more of the following constituents: a milk powder, gluten, an emulsifier, granulated fat, an oxidant, an amino acid, a sugar, a salt, flour or starch.

Examples of suitable emulsifiers are: monoglycerides, diacetyl tartaric acid esters of mono- and diglycerides of fatty acids, sugar esters, sodium stearoyl lactylate (SSL) and lecithins.

The bread and/or dough improving composition may further comprise another enzyme, such as one or more other suitable food grade enzymes, including starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases and acyltransferases (such as those described in WO04/064987 for instance).

The term "improved properties" as used herein means any property which may be improved by the action of the variant polypeptide of the present invention. In particular, the use of a variant polypeptide according to the present invention results in one or more of the following characteristics: increased volume of the baked product; improved crumb structure of the baked product; anti-staling properties in the baked product; increased strength, increased stability, reduced stickiness and/or improved machinability of the dough.

The improved properties are evaluated by comparison with a dough and/or a baked product prepared without addition of the variant polypeptide according to the present invention or by comparison with a dough and/or baked product prepared with the addition of a wild-type enzyme (e.g. KLM1; comprising the amino acid sequence shown herein as amino acids 33-296 (suitably 31-304 or 31-305) of SEQ ID No. 2).

The term "baked product" as used herein includes a product prepared from a dough. Examples of baked products (whether of white, light or dark type) which may be advantageously produced by the present invention include one or more of the following: bread (including white, whole-meal and rye bread), typically in the form of loaves or rolls or toast, French baguette-type bread, pitta bread, tortillas, tacos, cakes, pancakes, biscuits, crisp bread, pasta, noodles and the like.

The dough in accordance with the present invention may be a leavened dough or a dough to be subjected to leavening. The dough may be leavened in various ways such as by adding sodium bicarbonate or the like, or by adding a suitable yeast culture such as a culture of *Saccharomyces cerevisiae* (baker's yeast).

The present invention further relates to the use of fungal lipolytic enzymes in accordance with the present invention to produce a pasta dough, preferably prepared from durum flour or a flour of comparable quality.

The variant polypeptides according to the present invention are suitable for use in the enzymatic degumming of vegetable or edible oils. In processing of vegetable or edible oil the edible or vegetable oil is treated with a fungal lipolytic enzyme according to the present invention so as to hydrolyse a major part of the polar lipids (e.g. phospholipid and/or glycolipid). Preferably, the fatty acyl groups are hydrolysed from the polar lipids. The degumming process typically results in the reduction of the content of the polar lipids, particularly of phospholipids, in an edible oil due to hydrolysis of a major part (i.e. more than 50%) of the polar lipid, e.g. glycolipid and/or phospholipid. Typically, the aqueous phase containing the hydrolysed polar lipid (e.g. phospholipid and/or glycolipid) is separated from the oil. Suitably, the edible or vegetable oil may initially (pre-treatment with the enzyme according to the present invention) have a phosphorus content of 50-250 ppm.

Furthermore, the present invention is directed to the use of the variant polypeptides according to the present invention for treatment of cheese products.

The variant polypeptides according to the present invention are also particularly suitable for use in the preparation of an animal feed.

As the skilled person is aware, the term "degumming" as used herein means the refining of oil by converting phosphatides (such as lecithin, phospholipids and occluded oil) into hydratable phosphatides. Oil which has been degummed is more fluid and thus has better handling properties than oil which has not been degummed.

The following table is merely for general guidance and provides an overview of the dosage level for a variant polypeptide according to the present invention which may be needed in different applications. The table further provides guidance in respect of the dosage level for a lipolytic enzyme according to the present invention when used in combination with an emulsifier for example. Of course, as would be apparent to the person of ordinary skill in the art optimisation of enzyme dosage, reaction temperature and reaction time may be readily determined, using routine experimentation, for any given application.

| Application | "Optimal" dosage, TIPU/kg of flour | Optimal dosage in combination with emulsifier | Dosage range, TIPU/KG of flour |
|---|---|---|---|
| Crusty rolls | 50 | 15 | 25-125 |
| Straight dough toast bread | 50 | 15 | 25-125 |
| Straight dough long fermentation | 15 | | 10-50 |
| High speed mixing - Tweedy procedure | | 15 | 25-125 |
| US sponge & dough pan bread on top of DATEM | | 15 | 10-75 |
| Wheat tortilla | 100 | Contains emulsifiers | 50-350 |
| Cakes - sponge cakes | 250 | Contains cake emulsifiers | 125-500 |
| Retarded dough (24 hours) | 15 | Contains emulsifiers | 10-50 |
| Steam buns | 25 | | 20-100 |
| Instant fried noodles | | | 25-1250 |

Glycosylation

It has surprisingly been found that by introducing even one glycosylation site into a lipolytic enzyme (particularly those that do not comprise any glycosylation sites naturally), e.g. such as the lipolytic enzymes taught herein (e.g. the *Fusarium heterosporum* enzyme (sometimes designated herein as KLM1) and/or the *Fusarium oxysporum* lipolytic enzyme (sometimes designated herein as Lipopan F™)) the results on the level of expression and/or the functionality and/or the activity of the enzyme is much improved compared with the wild-type enzymes—particularly when the host cell is *Trichoderma* spp., such as *T. reesei*.

Therefore the present invention provides modifying a lipolytic enzyme (particularly one comprising amino acids 40-290 (preferably 35-300, more preferably 31-305) of the amino acid SEQ ID No. 2) or the nucleotide sequence encoding a lipolytic enzyme (such as the nucleotide sequence shown herein as SEQ ID No. 1) to substitute or insert amino acids in the sequence to produce variant polypeptides comprising an added glycosylation site. Notably, the wild-type enzyme shown as SEQ ID No. 2 (preprosequence for KLM1) or comprising amino acids 33-296 (suitably 31-304 or 31-305) of SEQ ID No. 2 for the mature sequence does not naturally comprise any glycosylation sites. Suitably, the lipolytic enzyme is modified to substitute or insert one or more amino acids selected from Asn, Ser, Thr for the purpose of introducing at least one glycosylation site (suitably more than one glycosylation site).

Notably the wild-type enzyme from *Fusarium heterosporum* CBS 782.83 (designated herein as KLM1 and having the preprosequence shown as SEQ ID No. 2 with the mature sequence comprise amino acids 33-296 (such as 31-304 or 31-305) of SEQ ID No. 2) has no glycosylation sites. It was surprising for the inventors that even a modest addition, i.e. the addition of one glycosylation site, could bring about such a significant improvement with regard to expression, functionality and/or activity.

The term "glycosylation site" as used herein means a sequence Asn-Xxx-Ser or Asn-Xxx-Thr wherein Xxx is any amino acid residue except proline.

When we refer to glycosylation site herein we may mean potential glycosylation site. In other words we provide the appropriate consensus sequence, i.e. Asn-Xxx-Ser or Asn-Xxx-Thr wherein Xxx is any amino acid residue except proline in the variant enzyme and when such a protein carrying the consensus sequence is secreted by the fungal host there is a high probability that the γ-amide of the asparagine will be glycosylated (although tertiary structure of the protein may modulate the efficiency of glycosylation).

Glycosylation is the enzymatic process that links saccharides to produce glycans, either free or attached to proteins and lipids. This enzymatic process produces one of four fundamental components of all cells (along with nucleic acids, proteins, and lipids) and also provides a co-translational and post-translational modification mechanism that modulates the structure and function of membrane and secreted proteins. The majority of proteins synthesized in the rough ER undergo glycosylation. It is an enzyme-directed site-specific process, as opposed to the non-enzymatic chemical reaction of glycation. Glycosylation is also present in the cytoplasm and nucleus as the O-GlcNAc modification. Six classes of glycans are produced: N-linked glycans attached to the amide nitrogen of asparagine side chains, O-linked glycans attached to the hydroxy oxygen of serine and threonine side chains; glycosaminoglycans attached to the hydroxy oxygen of serine; glycolipids in which the glycans are attached to ceramide, hyaluronan which is unattached to either protein or lipid, and GPI anchors which link proteins to lipids through glycan linkages.

In the present invention when we refer to glycosylation we are only referring to N-linked glycosylation. In other words the present invention is not intended to relate to O-linked glycosylation.

For N-linked oligosaccharides, a 14-sugar precursor is first added to the asparagine in the polypeptide chain of the target protein. The structure of this precursor is common to most eukaryotes, and contains 3 glucose, 9 mannose, and 2 N-acetylglucosamine molecules. A complex set of reactions attaches this branched chain to a carrier molecule called dolichol, and then it is transferred to the appropriate point on the polypeptide chain as it is translocated into the ER lumen.

There are three major types of N-linked saccharides: high-mannose oligosaccharides, complex oligosaccharides and hybrid oligosaccharides.

High-mannose is, in essence, just two N-acetylglucosamines with many mannose residues, often almost as many as are seen in the precursor oligosaccharides before it is attached to the protein.

Complex oligosaccharides are so named because they can contain almost any number of the other types of saccharides, including more than the original two N-acetylglucosamines.

Proteins can be glycosylated by both types of oligos on different portions of the protein. Whether an oligosaccharide is high-mannose or complex is thought to depend on its accessibility to saccharide-modifying proteins in the Golgi. If the saccharide is relatively inaccessible, it will most likely stay in its original high-mannose form. If it is accessible, then it is likely that many of the mannose residues will be cleaved off and the saccharide will be further modified by the addition of other types of group as discussed above.

The oligosaccharide chain is attached by oligosaccharyltransferase to asparagine occurring in the tripeptide consensus sequence Asn-Xxx-Ser or Asn-Xxx-Thr where X could be any amino acid except Pro. This sequence is also known as a glycosylation sequon. After attachment, once the protein is correctly folded, the three glucose residues are removed from the chain and the protein is available for export from the ER. The glycoprotein thus formed is then transported to the Golgi where removal of further mannose residues may take place.

In the present invention when we discuss modifying a lipolytic (backbone) enzyme, e.g. a wild-type enzyme such as KLM1 or Lipopan F or the nucleotide sequence encoding same to substitute or insert one or more amino acids such that the variant polypeptide formed comprises at least one glycosylation site (or at least one additional glycosylation site compared with the backbone enzyme)—we mean substituting the amino acids in the backbone enzyme or inserting one or more amino acids into the backbone such that one or more consensus sequences Asn-Xxx-Ser or Asn-Xxx-Thr where X could be any amino acid except Pro are introduced.

In one embodiment, suitably the modification may be the substitution or introduction of a single amino acid in the backbone sequence. For example the backbone sequence may comprise the following: Yyy-Xxx-Ser or Yyy-Xxx-Thr or Asn-Xxx-Zzz (where Xxx is not Pro, Yyy is not Asn and Zzz is not Ser or Thr)—and may simply require the substitution of amino acid Yyy with Asn and the substitution of Zzz with either Ser or Thr or the insertion of Asn after Yyy or the insertion of Ser or Thr before Zzz.

Alternatively, two or three of the amino acids in the backbone may be changed to produce a single glycosylation consensus sequence. For example, the backbone may be modified to substitute or insert three amino acids with Asn-Xxx-Ser or Asn-Xxx-Thr where X could be any amino acid except Pro.

Suitably more than one glycosylation site (potential glycosylation site) may be introduced into the back bone sequence such that the variant polypeptide comprises more than one glycosylation site (or more than additional glycosylation sites compared with the backbone sequence). Obviously the overall number of glycosylation sites (or potential glycosylation sites) in the variant polypeptide will depend on the number of glycosylation sites in the backbone enzyme and then number of glycosylation sites added. For the avoidance of doubt the wild-type KLM1 enzyme (shown herein as SEQ ID No. 2 does not comprise any glycosylation sites and therefore the number of glycosylation sites in the variant polypeptide will be determined by the number of added glycosylation sites.

Stabilisation of the C-Terminal

Suitably, the variant polypeptides according to the present invention may include C-terminal processing, preferably to render the polypeptide more stable. Suitably the C-terminal processing may comprise removal of the C-terminal KEX2 sites. Without wishing to be bound by theory it is thought that removal of the KEX2 site causes cessation or a decrease in the rate of proteolytic processing and improved stability of the enzyme without compromising its activity. One KEX2 site may be found at position 306 (when aligned with SEQ ID No. 2). Another KEX2 site may be found at positions 311-312 (when aligned with SEQ ID No. 2).

Suitably the C-terminal of the polypeptide commences at amino acid position 306 onwards.

External Loops Distal to the Active Site

In the present application it is taught that amino acid modifications (e.g. substitutions and/or insertions) are made to surface amino acids of the polypeptide which are located in external loops distal to the active site of the polypeptide in order to either introduce hydrophilic amino acids or to introduce one or more glycosylation sites.

When selecting a site for modification preferably the site is a) a surface location, b) a non-conservative amino acid, and c) at a location not in the immediate vicinity of the active site (catalytic tria) or the active site lid.

By the term "external loops" it is meant that a portion of the amino acid sequence which in the tertiary structure of the protein is exposed on the outer surface of the protein in a loop. The external loops are not involved in forming the catalytic triad or the lid region of the enzyme.

The term "active site" as used herein is synonymous with the term catalytic triad. For the avoidance of doubt the catalytic triad in the lipolytic enzymes taught herein are at positions The catalytic triad of the KLM1 enzyme is formed from S174, D228 and H287.

Preferably the external loops are more than about 15 Å, preferably more than about 16 Å, such as more than about 17 Å, more than about 18 Å, more than about 19 Å, preferably more than about 20 Å from the α-carbon of Ser174. For the avoidance of doubt both the catalytic triad and the lid region of the enzyme are less than 15 Å from the α-carbon of Ser174.

In one embodiment the external loops distal to the active site of the polypeptide correspond with the one or more of the following amino acid regions (with the amino acid positions Corresponding with the numbering shown in SEQ ID No. 2—i.e. obtained by aligning the lipolytic enzyme with SEQ ID No. 2 shown herein): 54-66, 75-79, 99-103, 127-135, 162-167, 188-195 and 213-221.

By the term "distal to the active site" it is meant remote to or at a distance from the active site of the protein. Preferably the external loops are at least about 15 Å, preferably more than about 16 Å, such as more than about 17 Å, more than about 18 Å, more than about 19 Å, preferably more than about 20 Å from the α-carbon of Ser174.

Hydrophilic Amino Acids

Depending on the polarity of the side chain, amino acids vary in their hydrophilic or hydrophobic character. Selecting amino acids which are more hydrophilic than other amino acids should be routine a person of ordinary skill in the art. In any event, guidance is provided in the below table:

| Amino Acid | 3-Letter | 1-Letter | Side chain polarity | Side chain charge (pH 7) | Hydropathy index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | | |

Lipolytic Enzyme

Preferably, the lipolytic enzyme or variant lipolytic enzyme according to the present invention has hydrolytic activity towards an ester bond in a polar lipid.

Preferably, the lipolytic enzyme or variant lipolytic enzyme according to the present invention hydrolyses polar lipids (e.g. glycolipids and/or phospholipids). In other words the variant lipolytic enzyme according to the present invention preferably has phospholipase activity (e.g. phospholipase A2 (E.C. 3.1.1.4) activity and/or phospholipase A1 (E.C. 3.1.1.32) activity) and/or galactolipase or glycolipase (E.C. 3.1.1.26) activity. The variant lipolytic enzyme according to the present invention may additionally hydrolyse triglycerides. In other words the variant lipolytic enzyme according to the present invention may additional have triglyceride lipase activity (E.C. 3.1.1.3).

The term "glycolipase activity" as used herein encompasses "galactolipase activity". The terms glycolipids and galactolipids may be used interchangeably herein and include hydrolysis of DGDG and MGDG, which are hydrolysed to DGMG or MGMG, respectively.

The term "polar lipids" as used herein means phospholipids and/or glycolipids. Preferably, the term "polar lipids" as used herein means both phospholipids and glycolipids.

Suitably the variant polypeptide according to the present invention may have phospholipase activity (e.g. phospholipase A2 (E.C. 3.1.1.4) activity and/or phospholipase A1 (E.C. 3.1.1.32) activity) and/or galactolipase or glycolipase (E.C. 3.1.1.26) activity.

The glycolipase activity, phospholipase activity and triacylglyceride lipase activity of an enzyme can be determined using the assays presented hereinabove.

In some embodiments the lipolytic enzyme prior to modification in accordance with the present invention does not comprise a glycosylation site.

In one embodiment the lipolytic enzyme prior to modification in the accordance with the present invention (i.e. the fungal lipolytic enzyme) is one which belongs to the family 23 of alpha/beta hydrolases, more specifically to the subfamily 23.01 (as classified by the lipase engineering database from the University of Stuttgart—see http://www.led.uni-stuttgart.de/). This database integrates information on the sequence and structure of lipases and related proteins sharing the same a/b hydrolase fold.

Isolated

In one aspect, preferably the sequence is in an isolated form. The term "isolated" means that the sequence is at least substantially free from at least one other component with which the sequence is naturally associated in nature and as found in nature.

In one embodiment the polypeptides and/or nucleotides sequences of the present invention are isolated.

Purified

In one aspect, preferably the sequence is in a purified form. The term "purified" means that the sequence is in a relatively pure state—e.g. at least about 90% pure, or at least about 95% pure or at least about 98% pure.

In one embodiment the polypeptides and/or nucleotides sequences of the present invention are purified.

Nucleotide Sequence

The scope of the present invention encompasses nucleotide sequences encoding enzymes having the specific properties as defined herein.

The term "nucleotide sequence" as used herein refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Preparation of the Nucleotide Sequence

Typically, the nucleotide sequence encompassed by scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding an enzyme which has the specific properties as defined herein may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for the enzyme (e.g. maltose for a glucosidase (maltase) producing enzyme), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence. However, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The enzyme encompassed in the present invention may be used in conjunction with other enzymes. Thus the present invention also covers a combination of enzymes wherein the combination comprises the enzyme of the present invention and another enzyme, which may be another enzyme according to the present invention.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95, 98% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95, 98% or 99% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI Advance™ 11 (Invitrogen Corp.). Examples of other software that can perform sequence comparisons include, but are not limited to, the BLAST package (see Ausubel et al 1999 Short Protocols in Molecular Biology, 4th Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI Advance™ 11 program. A new tool, called BLAST 2 Sequences is also available for comparing protein and nucleotide sequence (see FEMS Microbiol Lett 1999 174(2): 247-50; and FEMS Microbiol Lett 1999 177(1): 187-8.).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI Advance™ 11 package.

Alternatively, percentage homologies may be calculated using the multiple alignment feature in Vector NTI Advance™ 11 (Invitrogen Corp.), based on an algorithm, analogous to CLUSTAL (Higgins DG & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the default parameters for the programme are used for pairwise alignment. For example, the following parameters are the current default parameters for pairwise alignment for BLAST 2:

| FOR BLAST2 | DNA | PROTEIN |
|---|---|---|
| EXPECT THRESHOLD | 10 | 10 |
| WORD SIZE | 11 | 3 |
| SCORING PARAMETERS | | |
| Match/Mismatch Scores | 2, −3 | n/a |
| Matrix | n/a | BLOSUM62 |
| Gap Costs | Existence: 5 | |
| Extension: 2 | Existence: 11 | |
| Extension: 1 | | |

In one embodiment, preferably the sequence identity for the nucleotide sequences and/or amino acid sequences may be determined using BLAST2 (blastn) with the scoring parameters set as defined above.

For the purposes of the present invention, the degree of identity is based on the number of sequence elements which are the same. The degree of identity in accordance with the present invention for amino acid sequences may be suitably determined by means of computer programs known in the art such as Vector NTI Advance™ 11 (Invitrogen Corp.). For pairwise alignment the scoring parameters used are preferably BLOSUM62 with Gap existence penalty of 11 and Gap extension penalty of 1.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or 13-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses the use of sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences that are complementary to sequences that are capable of hybridising under high stringency conditions or intermediate stringency conditions to nucleotide sequences encoding polypeptides having the specific properties as defined herein.

More preferably, the present invention encompasses the use of sequences that are complementary to sequences that are capable of hybridising under high stringency conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridise to the nucleotide sequences discussed herein (including complementary sequences of those discussed herein).

The present invention also relates to the use of nucleotide sequences that are complementary to sequences that can hybridise to the nucleotide sequences discussed herein (including complementary sequences of those discussed herein).

Also included within the scope of the present invention are the use of polynucleotide sequences that are capable of hybridising to the nucleotide sequences discussed herein under conditions of intermediate to maximal stringency.

In a preferred aspect, the present invention covers the use of nucleotide sequences that can hybridise to the nucleotide sequences discussed herein, or the complement thereof, under stringent conditions (e.g. 50° C. and 0.2×SSC).

In a more preferred aspect, the present invention covers the use of nucleotide sequences that can hybridise to the nucleotide sequences discussed herein, or the complement thereof, under high stringency conditions (e.g. 65° C. and 0.1×SSC).

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual, Second Edition, Books* 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Enzymes

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences e.g. regulatory sequences.

The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

In one embodiment the pTrex 3 expression vector may be used as described in the Examples.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of an enzyme having the specific properties as defined herein.

Thus, a further embodiment of the present invention provides host cells transformed or transfected with a nucleotide sequence that expresses the enzyme of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the enzyme of the present invention, and/or the desirability for further processing of the expressed protein, eukaryotic hosts such as yeasts or other fungi may be preferred. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNA's, and modification of the reductive potential in the cytoplasm to enhance disulphide bond formation.

For example, the host cell *E. coli* may overexpress rare tRNA's to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favouring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

In a preferred embodiment the host cell is a fungal host cell, preferably a filamentous fungi host cell, preferably from the genus *Trichoderma*. In a preferred embodiment preferably the host cell is *Trichoderma reesei*.

It has surprisingly been found that the expression of the variant polypeptides of the present invention can be substantially increased by using *T. reesei* as the host cell.

Before the present invention lipolytic enzymes from *Fusarium heterosporum* (i.e. the wt KLM1) had been produced by expression in the yeast *Hansenula polymorpha*. When considering alternative expression systems with the aim to scale the production for mass enzyme production expression in *T. reesei* was considered. However, the wt KLM1 enzyme is inefficiently produced in *T. reesei*.

Surprisingly, however, it has been found that variant polypeptides according to the present invention have significantly improved expression levels in *T. reesei*—12 to 25 times better than the wild type KLM 1 enzyme. This is a significant improvement which can lead to significant cost reductions in production on a commercial scale of the enzyme.

In one embodiment the present invention provides a method for expressing variant lipolytic enzymes in *Trichoderma reesei* comprising transforming *T. reesei* with a nucleotide sequence encoding a polypeptide having hydrolytic activity towards an ester bond in a polar lipid (such as a nucleotide sequence according to the present invention) and culturing the *T. reesei* to obtain expression of the nucleotide sequence and harvesting the polypeptide.

Organism

The term "organism" in relation to the present invention includes any organism that could comprise the nucleotide sequence coding for the enzyme according to the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the enzyme according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the enzyme according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the enzyme of the present invention under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023. In one embodiment preferably *Trichoderma reesei* is the host organism.

Another host organism can be a plant. A review of the general techniques used for transforming plants may be found in articles by Potrykus (*Annu Rev Plant Physiol Plant Mol Biol [*1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like. In one embodiment preferably *Trichoderma* is the host organism, preferably *T. reesei.*

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

Gene expression in filamentous fungi has been reviewed in Punt et al. (2002) Trends Biotechnol 2002 May; 20(5):200-6, Archer & Peberdy *Crit. Rev Biotechnol* (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisiae* or *Pichia pastoris* or *Hansenula polymorpha* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts, Vol* 5, Anthony H Rose and J Stuart Harrison, Eds., 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, *J Bacteriology* 153, 163-168).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* 42:205-225) and Christou (Agro-Food-Industry Hi-Tech March/April 1994 17-27).

Culturing and Production

Host cells transformed with the nucleotide sequence of the present invention may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The enzyme may be secreted from the host cells and may conveniently be recovered from the culture medium using well-known procedures.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

The amino acid sequence for use according to the present invention may be produced as a fusion protein, for example to aid in extraction and purification. Examples of fusion protein partners include glutathione-S-transferase (GST), 6×His (SEQ ID NO: 43), GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Large Scale Application

In one preferred embodiment of the present invention, the amino acid sequence is used for large scale applications.

Preferably the amino acid sequence is produced in a quantity of from 1 g per liter to about 25 g/liter, preferably from above 2.5 g/liters to about 18 g/liter, preferably above 8 g per liter of the total cell culture volume after cultivation of the host organism.

Food/Foodstuff

The composition of the present invention may be used as—or in the preparation of—a food or foodstuff. Here, the term "food" or "foodstuff" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

Food Ingredient

The composition of the present invention may be used as a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the form of a solution or as a solid—depending on the use and/or the mode of application and/or the mode of administration.

Food Products

The composition of the present invention can be used in the preparation of food products such as one or more of: confectionery products, dairy products, poultry products, fish products and bakery products.

The present invention also provides a method of preparing a food or a food ingredient, the method comprising admixing a lipolytic enzyme according to the present invention with another food ingredient.

EXAMPLES

The present invention will now be described, by way of example only, in which reference may be made to the following figures:

FIG. 1 shows SEQ ID No. 1 a synthetic DNA fragment encoding a lipolytic enzyme from *Fusarium heterosporum* CBS 782.83 (wild type);

FIG. 2 shows a protein preprosequence SEQ ID No. 2 of a lypolytic enzyme from *Fusarium heterosporum* CBS 782.83 (wild type)—the preprosquence undergoes translational modification such that the mature form of the enzyme comprises amino acids 31-305 of SEQ ID No. 2, and preferably consists of amino acids 31-305 of SEQ ID No. 2. However in some host organisms the protein may be N-terminally processes such that a number of additional amino acids are added onto the N- or C-terminus. Thus the mature form of the enzyme may an enzyme comprising at least amino acids 31-305 of the SEQ ID No. 2. The mature form of the enzyme may be referred to herein as KLM 1. This enzyme is considered to be the wild-type enzyme;

FIGS. 3A-3C show SEQ ID No. 3 the DNA sequence of expression vector pTrex3 which is shown in graphical from in FIG. 23;

FIG. 4 shows SEQ ID No. 4 which is the DNA sequence for the polypeptide variant designated "mut 3";

FIG. 5 shows SEQ ID No. 5 which is the protein preprosequence for the polypeptide variant designated "mut 3";

FIG. 6 shows SEQ ID No. 6 which is the DNA sequence for the polypeptide variant designated "mut 4";

FIG. 7 shows SEQ ID No. 7 which is the protein preprosequence for the polypeptide variant designated "mut 4";

FIG. 8 shows SEQ ID No. 8 which is the DNA sequence for the polypeptide variant designated "mut 5";

FIG. 9 shows SEQ ID No. 9 which is the protein preprosequence for the polypeptide variant designated "mut 5";

FIGS. 10A-10B show SEQ ID No. 10 which is the DNA sequence for the polypeptide variant designated "mut 345";

FIG. 11 shows SEQ ID No. 11 which is the protein preprosequence for the polypeptide variant designated "mut 345";

FIG. 12 shows SEQ ID No. 12 which is the DNA sequence for the polypeptide variant designated "mut 3459";

FIG. 13 shows SEQ ID No. 13 which is the protein preprosequence for the polypeptide variant designated "mut 3459";

FIG. 14 shows SEQ ID No. 14 which is the DNA sequence for the polypeptide variant designated "mut 9";

FIG. 15 shows SEQ ID No. 15 which is the protein preprosequence for the polypeptide variant designated "mut 9";

FIG. 16 shows SEQ ID No. 16 which is the DNA sequence for the polypeptide variant designated "mut 10";

FIG. 17 shows SEQ ID No. 17 which is the protein preprosequence for the polypeptide variant designated "mut 10";

FIG. 18 shows SEQ ID No. 18 which is the DNA sequence for the polypeptide variant designated "mut 11";

FIG. 19 shows SEQ ID No. 19 which is the protein preprosequence for the polypeptide variant designated "mut 11";

FIG. 20 shows SEQ ID No. 20 which is the DNA sequence for the polypeptide variant designated "mut 12";

FIG. 21 shows SEQ ID No. 21 which is the protein preprosequence for the polypeptide variant designated "mut 12";

FIG. 22 shows an alignment of the acid sequences of the polypeptide variants (preprosequences) (SEQ ID NOS 25, 5, 7, 9, 41, 11, 13, 17, 19 and 42, respectively, in order of appearance) and wild type enzymes (shown herein as a) SEQ ID No. 2—designated as the preprosequence for KLM1 wt, b) the *Fusarium oxysporum* lipase as taught in EP 0 867 167—shown herein as SEQ ID No. 22; this enzyme is sometimes referred to herein as Lipopan F™ or "F.ox EP"; and a further amino acid sequence for a *Fusarium oxysporum* lipase as taught in U.S. Pat. No. 7,465,570—shown herein as SEQ ID No. 23; this enzyme is sometimes referred to herein as Lipopan F™ or "F.ox US".

Figure 23:
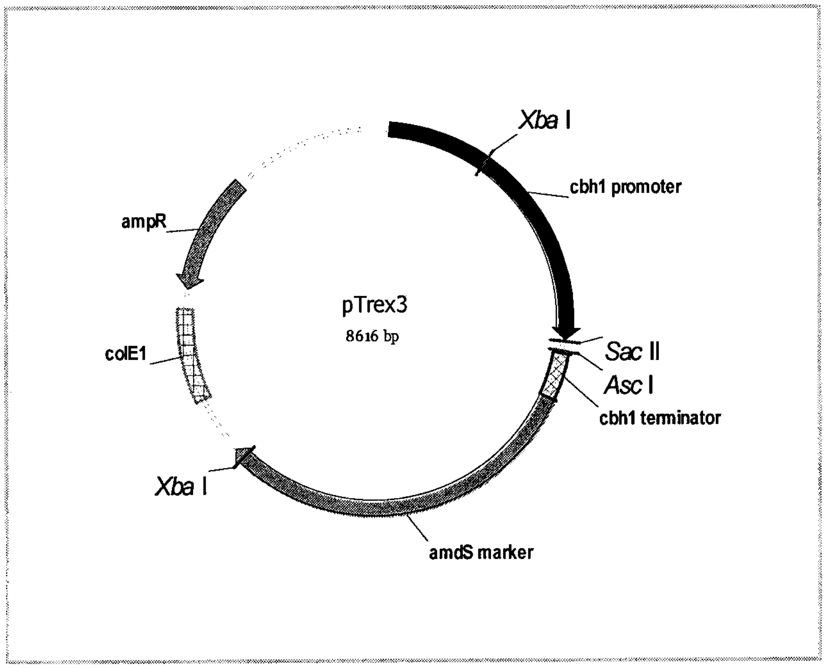
Figure 24:
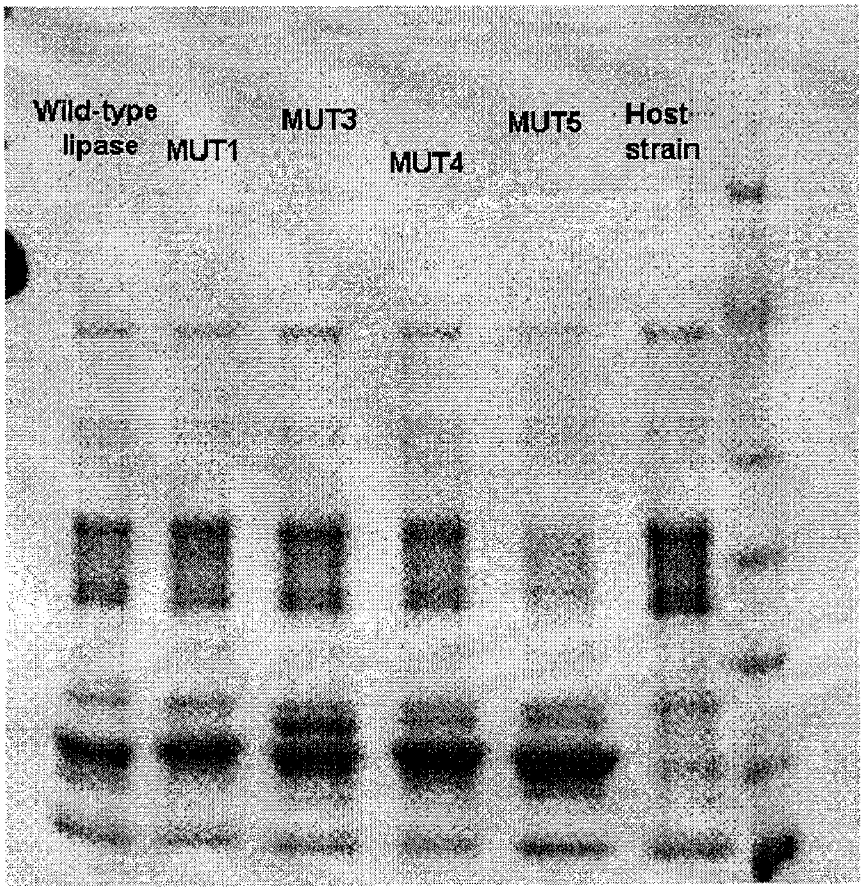
Figure 25:
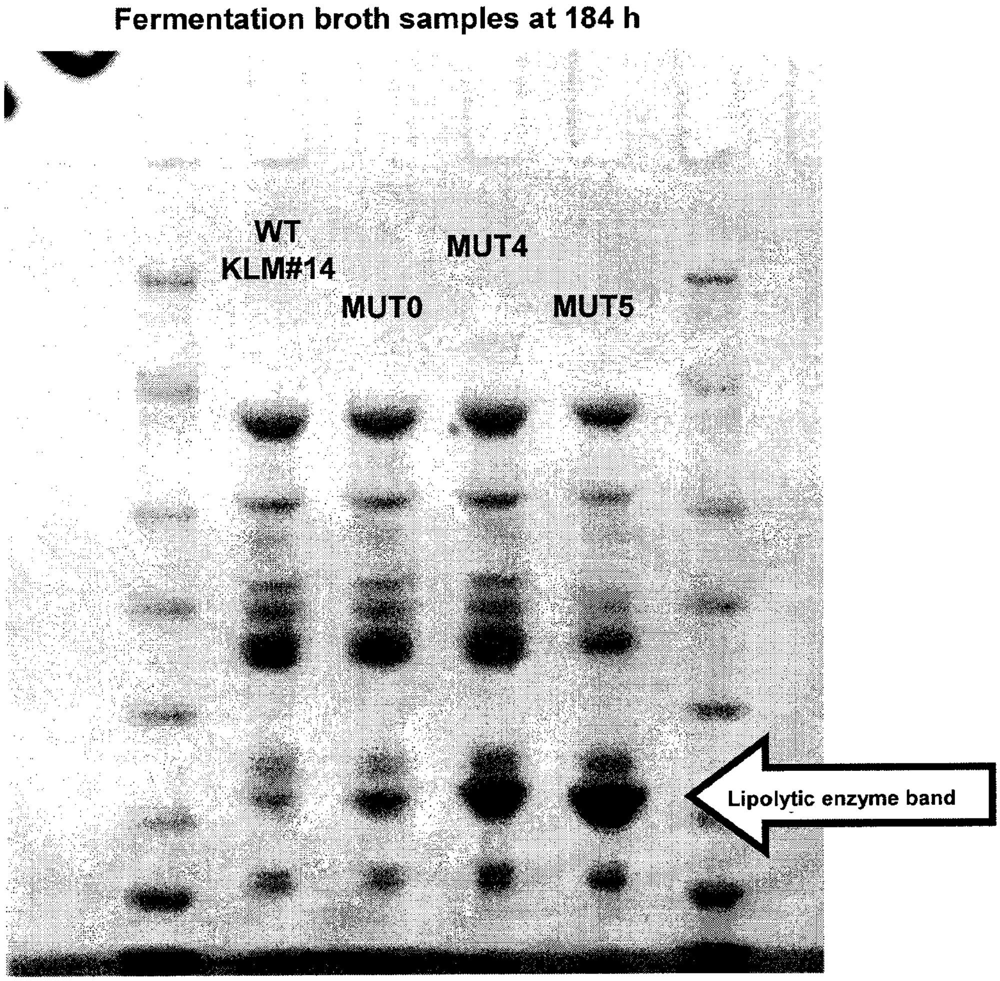
Figure 26:
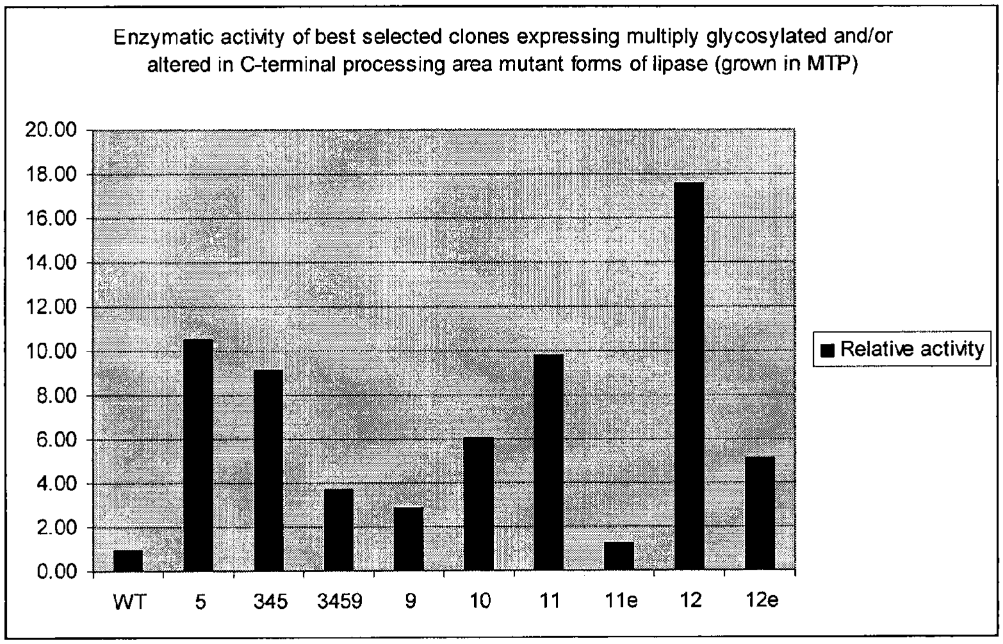
Figure 27:
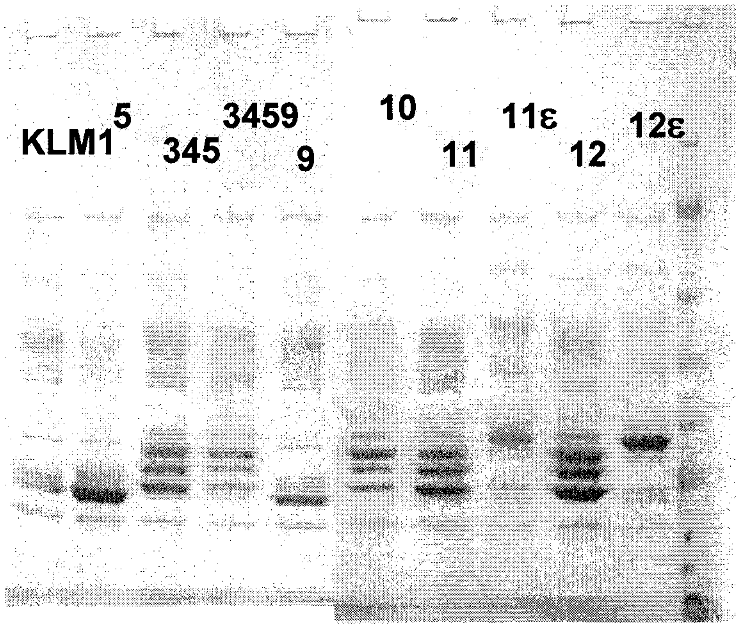
Figure 28:
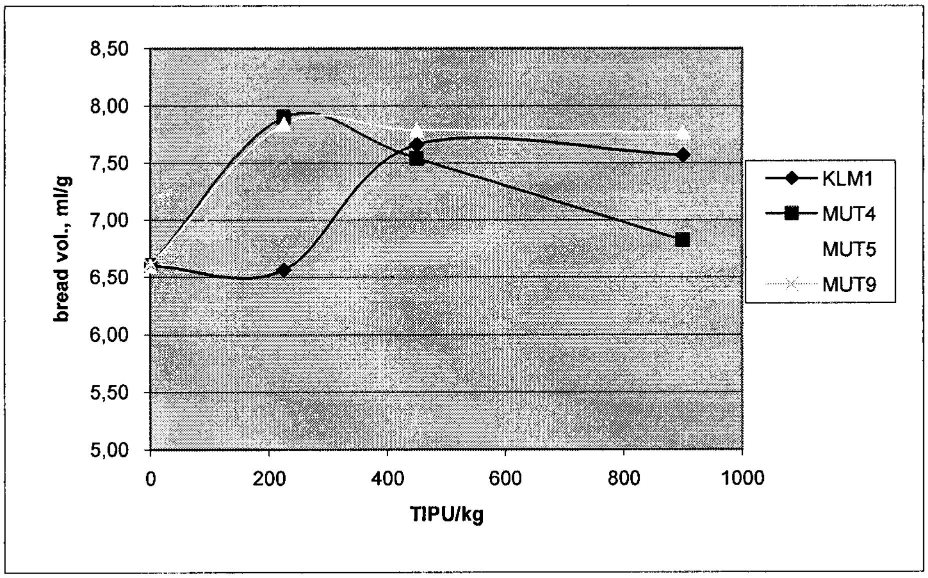
Figure 29:
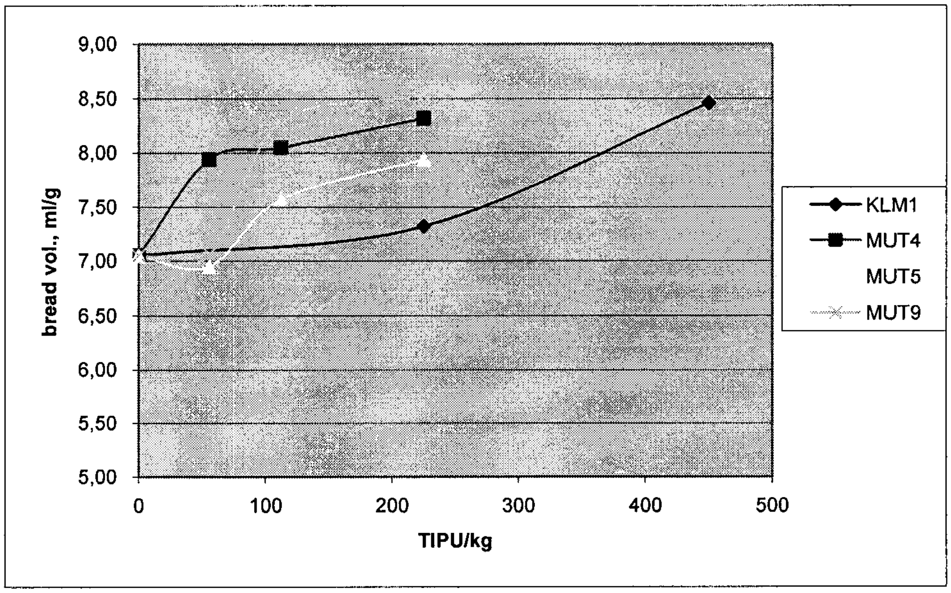

FIG. 23 depicts the structure of the expression vector pTrex3 in graphical form wherein the synthetic DNA fragment encoding the lipase from *Fusarium heterosporum* CBS 782.83 (DNA sequence SEQ ID No: 1 has been digested with SacII and AscI and cloned between SacII and AscI restriction sites;

FIG. 24 shows the expression of wild type lipolytic enzyme and four single-site glycosylation mutants in microtiter plates;

FIG. 25 shows the expression of wild type KLM 1 lipolytic enzyme, C-terminal processing site mutant and two single-site glycosylation mutants in fed batch fermentation (184 h);

FIG. 26 shows expression levels of multiply glycosylated and/or modified in the C-terminal processing area mutants of lipolytic enzyme from CBS 782.83 measured in DGGR assay (Example 1). Activities are expressed relative to the activity of wt lipolytic enzyme;

FIG. 27 shows expression levels of multiply glycosylated and/or modified in the C-terminal processing area mutants of lipolytic enzyme from CBS 782.83. KLM1: wild type lipolytic enzyme. 5, 345, 3459, 9, 10, 11 and 12: mutants MUT 5, MUT 345, MUT 3459, MUT 9, MUT 10, MUT 11, MUT 12 expressed in quad-deleted *T. reesei* strain. 11ϵ and 12ϵ: MUT11 and MUT 12 expressed in Endo-T deleted strain of *T. reesei*;

FIG. 28 show the results of the first baking trial—showing bread volume (ml/g) as a function of lipolytic enzyme (KLM1, Mut4, Mut5 and Mut9) and dose (TIPU/kg flour);

FIG. 29 shows the results from the second baking trial, bread volume (ml/g) as a function of lipolytic enzyme (KLM1, Mut4, Mut5 and Mut9) and dose (TIPU/kg flour);

FIG. 30 shows the amino acid sequence for *Fusarium oxysporum* lipase as taught in EP 0 867 167—shown herein as SEQ ID No. 22; this enzyme is sometimes referred to herein as Lipopan F™ or "F.ox EP".

Figure 31:
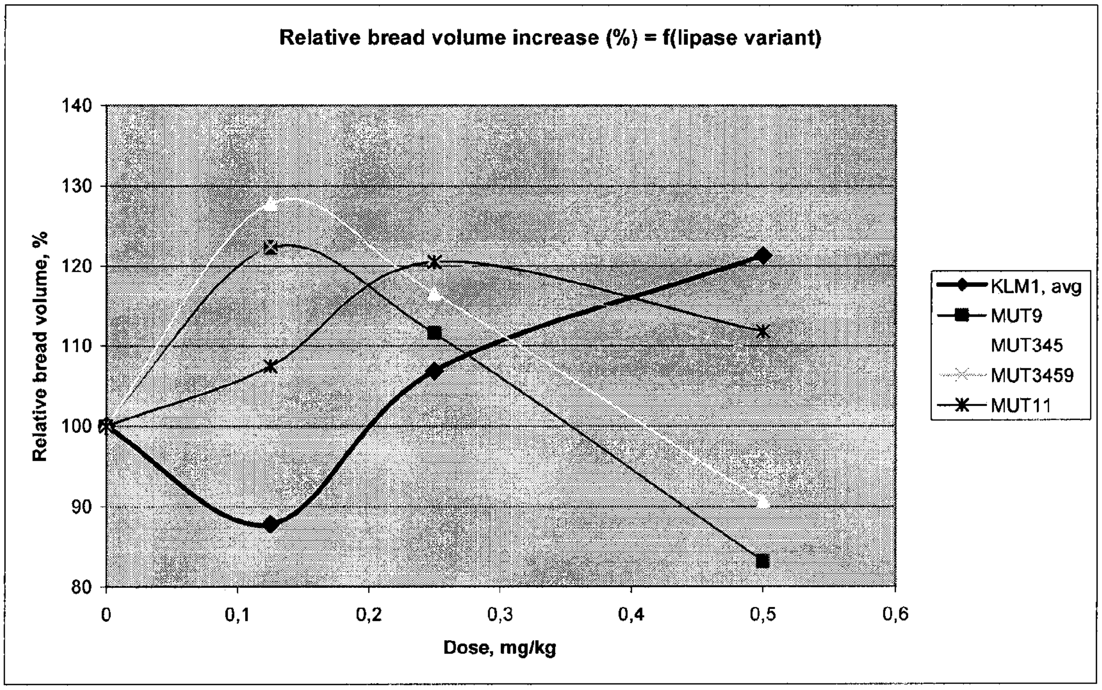
Figure 32:
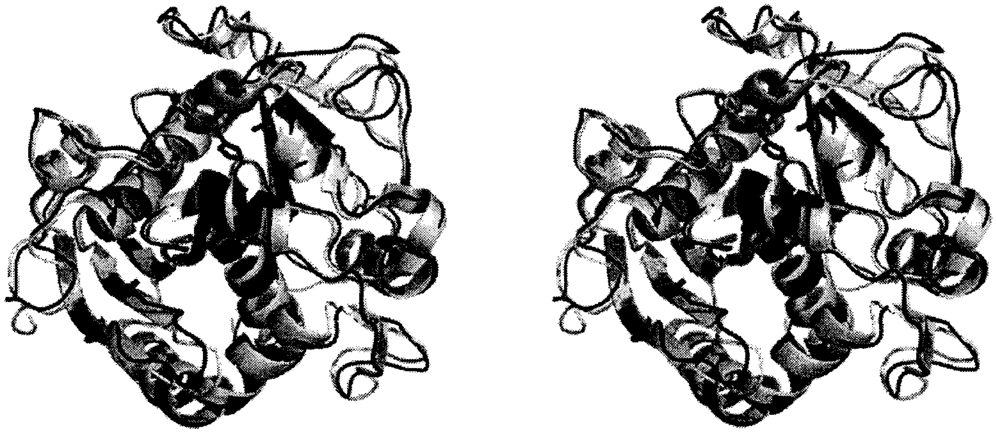
Figure 33:
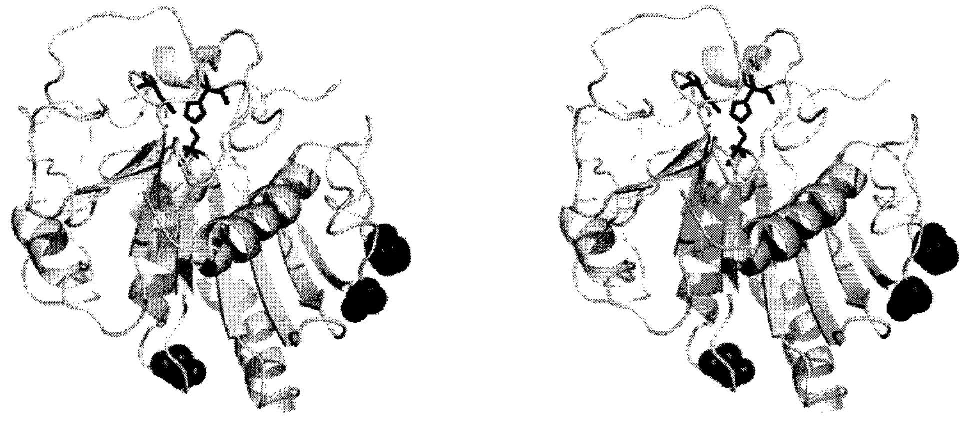
Figure 34:

FIG. 31 shows the results of baking trials for Mut 9, Mut345, Mut3459 and Mut 11, the graph depicting relative bread volume (%) of bread baked with different variants in different doses (mg/kg flour);

FIG. 32 shows a stereoview comparing the homology model of residues 33-296 of the KLM1 lipolytic enzyme (dark lines) with the structure of the *Thermomyces* lipase (pdb entry 1DT3) in light lines. The two structure share a high conservation of secondary structure with the catalytic traid of the homology model found at the location relative to common features of secondary structure found in the *Thermomyces* lipase;

FIG. 33 shows a stereoview showing the relative location of the substitutions at positions 63, 78 and 190 (shown in space filing representation) relative to the catalytic triad shown in the stick representation. It can be seen that these position are found in Loops that are distal to the catalytic triad;

FIG. 34 shows a stereoview showing the location of distal loops in the KLM1 lipolytic enzyme based on the homology model. These loops incorporate the position of substitutions at positions 63, 78 and 190 shown in space filling representation and are distal to the catalytic triad shown as stick figures. These loops comprise residues 54-66, 75-79, 99-103, 127-135, 162-167, 188-195 and 213-221;

FIG. 35 shows an amino acid sequence for a *Fusarium oxysporum* lipase as taught in U.S. Pat. No. 7,465,570 as SEQ ID No. 1—shown herein as SEQ ID No. 23; this enzyme is sometimes referred to herein as Lipopan F™ or "F.ox US";

FIG. 36 shows a nucleotide sequence for the *Fusarium oxysporum* lipase as taught in EP 0 867 167—shown herein as SEQ ID No. 24; this enzyme is sometimes referred to herein as Lipopan F™ or "F.ox EP";

FIG. 37 shows SEQ ID No. 25 which is the protein preprosequence for the polypeptide variant designated "mut 1"; and FIG. 38 shows SEQ ID No. 26 which is the DNA sequence for the polypeptide variant designated "mut 1".

Example 1

Lipase Assay Using
1,2-O-dilauryl-rac-glycero-3-glutaric-resorufin ester
(DGGR Assay)

A substrate solution was prepared by mixing of 4 parts of buffer (50 mM HEPES pH 8, 0.4 mg/ml $MgCl_2$, 1.2 mg/ml $CaCl_2$, 2% Gum Arabic) and 1 part of substrate (664 µM 1,2-O-dilauryl-rac-glycero-3-glutaric-resorufin ester (DGGR, Fluka) in dimethylsulfoxide). A suitably diluted aliquot of lipase was added to 200 µl of the substrate solution in a well of a microtiter plate. The hydrolysis of DGGR results in a change of absorption at 572 nm that was followed in real time using a microtiter plate reader.

Example 2

Expression of the Wild-Type Lipolytic Enzyme from
*Fusarium heterosporum* CBS 782.83 (KLM1).

A synthetic DNA fragment encoding the lipolytic enzyme from *Fusarium heterosporum* CBS 782.83 (DNA sequence—SEQ ID No: 1; prepro protein sequence SEQ ID No: 2) has been digested with SacII and AscI and cloned between SacII and AscI restriction sites of the expression vector pTrex3.

pTrex3 comprises the following functional regions:
1. The *T. reesei* cbh1 promoter and part of the coding region. This DNA sequence begins at a naturally occurring XbaI site approximately 1500 bp upstream of the coding region and ends at the naturally occurring SfiI site within the cbh1 gene coding sequence corresponding to the signal peptide of CBHI.
2. An engineered AscI site followed by the *T. reesei* cbh1 transcription terminator region (approx. 0.36 kb)
3. A 2.75 kb fragment of *Aspergillus nidulans* genomic DNA including the promoter, coding region and terminator of the amdS (acetamidase) gene. A natural XbaI site occurs near the 3'-end of this fragment
4. About 3.2 kb fragment of bacterial DNA comprising the colE1 origin of replication and ampicillin resistance gene.

FIG. 23 depicts the structure of pTrex3 in graphical form. The DNA sequence of pTrex3 is listed as SEQ ID No: 3 (see FIG. 3).

The vector resulting from cloning the lipolytic enzyme gene in pTrex3 (pTrex3(KLM1)) has been digested with XbaI and SspI and a 4.5 kb XbaI-XbaI DNA fragment comprising the lipolytic expression cassette and amdS marker has been purified by agarose gel electrophoresis. The purified fragment was used to transform the spores of a quad-deleted strain of *T. reesei* (Δcbh1, Δcbh2, Δeg11, Δeg12, described in WO05/001036) by electroporation (A. N. Miasnikov, S. Kim. Transformation of *T. reesei* spores by electroporation. Poster No 598. Abstracts of 25th Fungal Genetics Conference at Asilomar. Mar. 17-22, 2009, p 266). The transformants were selected on a medium containing acetamide as a sole source of nitrogen (acetamide 0.6 g/l; cesium chloride 1.68 g/l; glucose 20 g/l; potassium dihydrogen phosphate 15 g/l; magnesium sulfate heptahydrate 0.6 g/l; calcium chloride dihydrate 0.6 g/l; iron (II) sulfate 5 mg/l; zinc sulfate 1.4 mg/l; cobalt (II) chloride 1 mg/l; manganese (II) sulfate 1.6 mg/l; agar 20 g/l; pH 4,25). Transformed colonies appeared in about 1 week. Individual transformants were transferred onto fresh acetamide selective plates and allowed to grow for 2-4 days. Isolates showing stable growth on selective medium were used to inoculate 0.2 ml of glucose-sophorose medium (1% sophorose, 0.6% glucose, 0.6% glycine, 3.3% PIPPS buffer, 0.47% $(NH_4)_2SO_4$, 0.5% $KH_2PO_4$, 0.3% citric acid, 0.1% $MgSO_4$, 500 mg/l $FeSO_4$, 40 mg/l $ZnSO_4$, 8 mg/l $CuSO_4$, 3.5 mg/l $MnSO_4$, 2 mg/l boric acid) in the wells of a microtiter plate equipped with a microfilter at the bottom (Millipore MultiScreen—GVT™). The plates were incubated for 4-6 days at 25-28° C. in an atmosphere of pure oxygen. The culture media were separated by filtration and analyzed by polyacrylamide gel electrophoresis in the presence of sodium dodecylsulfate (SDS PAGE) or the DGGR assay. A number of transformants produced a new protein band on the SDS gels. The estimated molecular weight of this band (about 28 kDa) corresponded to the expected molecular weight of the N- and C-terminals (Nagao et al. J. Biochem. 124, 1124-1129 (1998)) processed KLM1 lipase (28.6 kDa). Culture media of transformant clones that produced the 28 kDa band also contained substantial lipase activity (measured in DGGR assay). Essentially no lipase activity was detectable in the culture medium of the untransformed *T. reesei* strain used as the recipient in transformation.

Example 3

Expression of Mutant Forms of Lipolytic Enzyme from *Fusarium heterosporum* CBS 782.83

The mutant forms of lipolytic enzyme gene were constructed using standard PCR-based techniques. The DNA and protein sequences of the mutant genes and the prepro-forms of lipolytic enzymes are listed as indicated by Table 1. All mutants carry R306S mutation (Mutant j). Mutants 1, 3, 4 and 5 have a single N-linked glycosylation site consensus sequence introduced at different locations (the wild-type lipolytic enzyme (KLM1) has no N-linked glycosylation sites). Mutant 9 carries a deletion of two amino acid residues ($K_{311}R_{312}$). All other mutants contain multiple glycosylation sites.

TABLE 1

*Fusarium heterosporum* CBS 782.83 lipolytic enzyme mutants: nucleotide and prepro protein sequences and expression vectors

| Mutant | DNA sequence of the gene(*) | Protein sequence of the prepro-lipase | Expression vector |
|---|---|---|---|
| MUT 1 | SEQ ID No. 26 | SEQ ID No. 25 | pTrex3 (MUT1) |
| MUT 3 | SEQ ID No: 4 | SEQ ID No: 5 | pTrex3 (MUT3) |
| MUT 4 | SEQ ID No: 6 | SEQ ID No: 7 | pTrex3 (MUT4) |
| MUT 5 | SEQ ID No: 8 | SEQ ID No: 9 | pTrex3 (MUT5) |
| MUT 345 | SEQ ID No: 10 | SEQ ID No: 11 | pTrex3 (MUT345) |
| MUT 3459 | SEQ ID No: 12 | SEQ ID No: 13 | pTrex3 (MUT3359) |
| MUT 9 | SEQ ID No: 14 | SEQ ID No: 15 | pTrex3 (MUT9) |
| MUT 10 | SEQ ID No: 16 | SEQ ID No: 17 | pTrex3 (MUT10) |
| MUT 11 | SEQ ID No: 18 | SEQ ID No: 19 | pTrex3 (MUT11) |
| MUT 12 | SEQ ID No: 20 | SEQ ID No: 21 | pTrex3 (MUT12) |

(*)Confirmed by DNA sequencing.

The modifications in each of the mutant or variant lipolytic enzymes compared with the wild-type enzyme (KLM1; SEQ ID No. 2) is shown below in Table 2. All numbering is according to the sequence of wt prepro-KLM1 (shown herein as SEQ ID No. 2)

TABLE 2

| | |
|---|---|
| MUT 1 | R306S + G33N |
| MUT 3 | R306S + K63N |
| MUT 4 | R306S + G78N |
| MUT 5 | R306S + A190N |
| MUT 345 | R306S + K63N + G78N + A190N |
| MUT 9 | R306S + ΔKR311-312 |
| MUT 3459 | R306S + K63N + G78N + A190N + Δ311-312 |
| MUT 10 | R306S + K63N + G78N + A190N + Δ307-319 |
| MUT 11 | R306S + K63N + G78N + A190N + Δ307-319 + T320E |
| MUT 12 | R306S + K63N + G78N + A190N + Δ307-319 + R305N |

All of the mutant forms of the lipolytic enzyme gene have been cloned in pTrex3 in the same way as the wild type lipolytic enzyme gene (using SacII and AscI restrictions sites). Transformation of *T. reesei*, selection and cultivation of transformants were done as described in Example 2. At least 50 stable transformants expressing each of the mutants were analyzed. One transformant of each type producing the highest level of lipase was selected.

Example 4

Construction of a Disruption Cassette for the Endo T Gene of *T. reesei*

Endo T gene was identified in the genomic sequence of *T. reesei* (http://genome.jgi-psf.org/Trire2/Trire2.home.html) using the information of the patent application WO 2006/050584. Its 5' flanking region (1.9 Kb) was amplified by PCR using primers SK915 (5'-CTGATATCCTGGCATGGTGAATCTCCGTG-3' (SEQ ID NO: 27)) and S K916 (5'-CATGGCGCGCCGAGGCAGATAGGCGGACGAAG-3' (SEQ ID NO: 28)). The 3' flanking region (1.7 Kb) was amplified by PCR using primers SK917 (5'-CATGGCGCGCCGTGTAAGTGCGTGGCTGCAG-3' (SEQ ID NO: 29)) and SK918 (5'-CTGATATCGATCGAGTCGAACTGTCGCTTC-3' (SEQ ID NO: 30)). Pfull Ultra (Stratagene) was used as the polymerase in all PCR reactions. The products of the PCR reaction were purified with the QIAquick PCR purification kit (Qiagen) by following the protocol listed in the manual. Both amplified DNA fragments were digested with restriction endonuclease AscI, followed by purification of digested DNA using QIAquick kit. The two DNA fragments were mixed and used as a template for a fusion PCR reaction with primers SK915 and SK918. The product of this reaction, a 3.6 kb DNA fragment, was cloned into pCR-Blunt II TOPO vector using the Zero Blunt TOPO PCR Cloning Kit (Invitrogen). The structure of the resulting plasmid (pCR-BluntII-TOPO(5'-3' flank)) was confirmed by restriction analysis. A mutant form of the *T. reesei* acetolactate synthase (ALS) gene conferring resistance to chlorimuron ethyl (WO 2008/039370) has been amplified using PCR primers SK949 (5'-GTTTCGCATGGCGCGCCTGAGACAATGG-3' (SEQ ID NO: 31)) and SK946 (5'-CACAGGCGCGCCGATCGCCATCCCGTCGCGTC-3' (SEQ ID NO: 32)) and pTrex-Glucoamylase vector (WO 2008/039370, Example 2) as the template. The product of the PCR reaction was purified with QIAquick kit, digested with AscI, purified again and ligated with pCR-BluntII-TOPO(5'-3' flank) digested with the same enzyme and purified similarly. The orientation of the insert in the resulting plasmid pCR-BluntII-TOPO(5' flank-ALS marker-3' flank) was established by restriction analysis. An additional fragment of *T. reesei* chromosomal sequence (referred to as "3'-repeat") was amplified using the same techniques and primers MC40 (5'-CTATGACATGCCCTGAGGCGATGCTGGCCAGGTACGAGCTG-3' (SEQ ID NO: 33)) and MC41 (5'-CAGCCTCGCGGTCACAGTGAGAGGAACGGGGTGAAGTCGTATAAG-3' (SEQ ID NO: 34)). This sequence is located on *T. reesei* chromosome further downstream of the 3'-flank area that is contained within pCR-BluntII-TOPO(5'-3' flank). The 0.46 kb product of this PCR (3'-repeat) was cloned upstream of the ALS gene in the pCR-BluntII-TOPO(5' flank-ALS marker-3' flank) using In-Fusion Dry-Down PCR Cloning Kit (Clontech). pCR-BluntII-TOPO(5' flank-ALS marker-3' flank) was digested with PasI and BstEII for insertion of the 3' repeat. The resulting construct pCR-BluntII-TOPO(5' flank-ALS marker-3' repeat-3' flank) was used as the template for a PCR with primers SK1008 (CTAGCGATCGCGTGTGCACA TAGGTGAGTTCTCC (SEQ ID NO: 35)) and SK1009: (CTAGCGATCGCGCAGACTGGCATGCCTCAAT CAC (SEQ ID NO: 36)). The 7.5 kb DNA product was cloned into pCR-BluntII-TOPO vector using the corresponding kit from Invitrogen. The resulting plasmid was digested with AsiSI and a 7.5 kb DNA fragment (the Endo-T deletion cassette) was purified by preparative agarose gel electrophoresis.

Example 5

Disruption of the Endo-T gene in *T. reesei* and Transformation of the Resulting Mutant with Lipolytic Enzyme Expression Constructs A quad deleted strain of *T. reesei* (Δcbh1, Δcbh2, Δegl1, Δeg12) is described in WO05/001036 This strain was transformed with the deletion cassette (of Example 4) using transformation method described by Penttilä et al. (Penttilä M. et al. 1987. A versatile transformation system for the cellulolytic filamentous fungus *Trichoderma reesei*. Gene 61: 155-164). The transformants were selected on a Modified Vogel's medium containing 200 ppm chlorimuron ethyl (WO 2008/039370). Transformants were cultured in liquid medium and culture supernatants were analyzed by SDS gel electrophoresis. Two clones (#11 and #74) displaying an upward shift in mobility of most of the protein bands on the gel were identified. Chromosomal DNA was isolated from these two strains as well as the parent quad deleted strain of *T. reesei*. PCR analyses were performed on these DNA preparations using primer pairs MC 42 plus MC 48 (5'-CTCGCCATCTGACAACCTACAAATC-3' (SEQ ID NO: 37))and 5'-CTAGTACCCTGAGTTGTCTCGCCTCC-3' (SEQ ID NO: 38)) and MC 45 plus MC 50 (5'-CCTCTACCATAACAGGATCCATCTG-3' (SEQ ID NO: 39)and 5'-CGTGAGCTGATGAAGGAGAGAAC AAAGG-3' (SEQ ID NO: 40)). Products of the expected size (2.9 and 2.3 kb) were obtained with DNA isolated from clone #74. This clone was subjected to two successive rounds of purification (by isolation of progeny of a single spore). DNA was isolated from the purified transformant #74. PCR analyses were repeated confirming successful deletion of the Endo-T gene. The resulting mutant strain of *T. reesei* was transformed with pTrex3(MUT10), pTrex3(MUT11) and pTrex3(MUT12). Screening and spore-purification of the transformants were done as described in Example 3.

Example 6

Production of the Mutant Forms of Lipolytic Enzyme from *Fusarium heterosporum* CBS 782.83 Carrying Single Engineered Glycosylation Site The best selected transformants expressing wild-type lipolytic enzyme as well as mutants 3, 4 and 5 (see Examples 2 and 3) were cultivated for 4 days in microtiter plates as described above (in Example 2). Production of two of these mutants as well as the wild-type lipolytic enzyme and MUT 0 (carrying only R306S mutation) was also tested in a fermentor using the standard fed-batch process (WO 2004/035070). All three mutants containing a single engineered glycosylation site were expressed at higher level than wild-type lipolytic enzyme, especially under conditions of prolonged (184 hours) fed batch cultivation in fermentor (see FIG. 24 and FIG. 25 and Table 3).

TABLE 3

| Lipolytic enzyme variant | Expression level in MTP, 4 days(*) | Expression level in fermentor(*) |
|---|---|---|
| Wild type | 1.0 | 1.0 |
| MUT0 | n.d. | 1.2 |
| MUT 1 | 1.3 | n.d. |
| MUT 3 | 1.9 | n.d. |
| MUT4 | 2.3 | 8.3 |
| MUT5 | 2.1 | 10.8 |

(*)Relative activity values (wild type = 1) measured in DGGR assay (Example 1)

Example 7

Production of the Mutant Forms of Lipolytic Enzyme from *Fusarium heterosporum* CBS 782.83 Carrying Multiple Glycosylation Sites and Modification of the C-Terminal Proteolytic Processing Site Genes encoding mutants MUT345, MUT3459, MUT9, MUT10, MUT11 and MUT12 (Table 1) were expressed in quad deleted strain of *T. reesei* as described in Example 2. Genes encoding mutants MUT 11 and MUT 12 were additionally expressed in Endo-T deleted strain of *T. reesei* (see Example 5). At least 50 stable transformants were screened for lipolytic enzyme production as described in Example 2. Typically, each set of transformants would contain 5-6 clones expressing the lipolytic enzyme at similar level, highest for the given mutant. One such transformant was selected for each type of mutant. Selected best transformants were all cultivated in MTP for 7 days in one experiment and analysed by SDS PAGE and activity assays (see Example 1). The results (FIG. 25 and Table 4) indicate that all tested mutants are expressed at higher level than wild-type lipolytic enzyme. Multiply glycosylated mutants as a group do not show a substantial improvement in expression level compared to MUT 5 that carries only a single engineered N-linked glycosylation site. A notable exception is MUT 12 that produces about twice as much recombinant protein as MUT 5 or other mutants in this series.

TABLE 4

| Lipolytic enzyme variant | Expression level in MTP, 7 days(*) |
|---|---|
| Wild type | 1.0 |
| MUT5 | 10.52 |
| MUT 345 | 9.12 |
| MUT 3459 | 3.74 |
| MUT 9 | 2.90 |
| MUT 10 | 6.08 |
| MUT 11 | 9.80 |
| MUT 11 in Endo-T mutant strain | 1.25 |
| MUT 12 | 17.55 |
| MUT 12 in Endo-T mutant strain | 5.10 |

(*)Relative activity values (wild type = 1) measured in DGGR assay (Example 1)

Example 8

Application of Mutant Forms of Lipolytic Enzyme from *Fusarium heterosporum* CBS 782.83

To evaluate the functionality of the variants of the lipolytic enzyme, these were evaluated in pilot baking applications as described below.

Material and Methods

Enzymes

The following enzymes were used for the baking trials (Table 5)

TABLE 5

Enzyme samples used in application trials and their activity (TIPU/ml). KLM1 is identical to the mature form of wild-type lipolytic enzyme from *Fusarium heterosporum* CBS 782.93 expressed in *T. reesei* with the amino acid comprising amino acids 31-305 of the sequence shown herein as SEQ ID No. 2, Mut4, Mut5 and Mut9 are the variants described in Example 3 expressed in *T. reesei* and thus post-translationally modified into the mature form of the enzyme. The expression product was used in the following trials.

| Sample ID | TIPU/ml |
|---|---|
| KLM1 | 500 |
| Mut4 | 125 |
| Mut5 | 111 |
| Mut9 | 610 |

Enzymes Assays (TIPU)

Phospholipase activity determination of the enzymes used was performed using the following assay:

1 TIPU (Titration Phospholipase Unit) is defined as the amount of enzyme, which liberates 1 mmol free fatty acid per minute at the assay conditions.

Phospholipase A1 and A2 catalyse the conversion of lecithin to lyso-lecithin with release of the free fatty acid from position 1 and 2, respectively. Phospholipase activity can be determined by continuous titration of the fatty acids liberated from lecithin during enzymation, since the consumption of alkali equals the amount of fatty acid liberated.

Substrate:

4% lecithin, 4% Triton-X 100, and 6 mM $CaCl_2$: 12 g lecithin powder (Avanti Polar Lipids #44160) and 12 g Triton-X 100 (Merck 108643) was dispersed in approx. 200 ml demineralised water during magnetic stifling. 3.0 ml 0.6 M CaCl2 (p.a. Merck 1.02382) was added. The volume was adjusted to 300 mL with demineralised water and the emulsion was homogenised using an Ultra Thurax. The substrate was prepared freshly every day.

Assay Procedure:

An enzyme solution was prepared to give a slope on the titration curve between 0.06 and 0.18 ml/min with an addition of 300 μL enzyme.

A control sample of known activity is included.

The samples were dissolved in demineralised water and stirred for 15 min. at 300 rpm. 25.00 ml substrate was thermostatted to 37.0° C. for 10-15 minutes before pH was adjusted to 7.0 with 0.05 M NaOH. 300 μL enzyme solution was added to the substrate and the continuous titration with 0.05 M NaOH was carried out using a pH-Stat titrator (Phm 290, Mettler Toledo). Two activity determinations are made on each scaling. After 8 minutes the titration is stopped and the slope of the titration curve is calculated between 5 and 7 minutes. The detection limit is 3 TIPU/ml enzyme solution.

Calculations:

The phospholipase activity (TIPU/g enzyme) was calculated in the following way:

$$TIPU/\text{g} = \frac{\alpha \cdot N \cdot 10^6 \frac{\mu\text{mol}}{\text{mol}} \cdot 10^{-3} \frac{1}{\text{ml}} \cdot V_1}{m \cdot V_2} = \frac{\alpha \cdot N \cdot 10^3 \cdot V_1}{m \cdot V_2}$$

Where:

α is the slope of the titration curve between 5 and 7 minutes of reaction time (ml/min).

N is the normality of the NaOH used (mol/l).

V1 is the volume in which the enzyme is dissolved (ml).

m is the amount of enzyme added to V1 (g).

V2 is the volume of enzyme solution added to the substrate (ml).

Baking Protocol:

Recipe:

| Ingredients | % | G |
|---|---|---|
| Wheat flour | 100 | 2000 |
| Compressed fresh yeast | 6 | 120 |
| Salt | 1.6 | 32 |
| Sugar | 1.6 | 32 |
| Water | 400 BU - 2% | 1090 |

Equipment:

Mixer: Diosna

Heating cabinet

Moulding: Glimek rounder

Proofing cabinet

Oven:/MIWE

Procedure:

1. Mix all dry ingredients in the bowl for 1 min.—add water
2. Mixing program: 2 min. slow—5.5 min. fast
3. Dough temperature must be approx. 26° C.
4. Scale 1350 g—mould
5. Rest in heating cabinet for 10 min. at 30° C.
6. Mould on "Glimek rounder"—settings according to table on machine
7. Proof for 45 min. at 34°, 85% RH
8. Bake
9. After baking cool the rolls for 25 min. before scaling and measuring of the volume Baking trials:

Two baking trials were conducted using the wildtype- and the variant lipases. Trial setup are listed in Table 6 and Table 7.

TABLE 6

First baking trial set including 12 doughs dosed with different lipolytic enzymes (KLM1 (wt), Mut4, Mut5 or Mut9) at different doses (TIPU/kg flour).

| Baking | Variant ID | TIPU/kg flour |
|---|---|---|
| 1 | KLM1 | 225 |
| 2 | KLM1 | 450 |
| 3 | KLM1 | 900 |
| 4 | Control | 0 |
| 5 | MUT4 | 225 |
| 6 | MUT4 | 450 |
| 7 | MUT4 | 900 |
| 8 | MUT5 | 225 |
| 9 | MUT5 | 450 |
| 10 | Control | 0 |
| 11 | MUT5 | 900 |
| 12 | MUT9 | 225 |

TABLE 7

| Second baking trial set including 12 doughs dosed different lipolytic enzymes (KLM1 (wt), Mut4, Mut5 or Mut9) at different doses (TIPU/kg flour). | | |
|---|---|---|
| Baking | Mutant ID | TIPU/kg flour |
| 1 | KLM1 | 225 |
| 2 | KLM1 | 450 |
| 3 | MUT4 | 56 |
| 4 | MUT4 | 112 |
| 5 | MUT4 | 225 |
| 6 | MUT5 | 56 |
| 7 | MUT5 | 112 |
| 8 | MUT5 | 225 |
| 9 | Control | 0 |
| 10 | MUT9 | 56 |
| 11 | MUT9 | 112 |
| 12 | MUT9 | 225 |

Analysis of Lipid Modification:

Dough were collected after proofing (see baking recipe) and immediately frozen. Hereafter the frozen dough samples were lyophilised and milled in a coffee mill. Lipids were extracted from the dough samples and analysed by the following protocol:

Lipid Extraction 6.0 mL water saturated Butanol:Ethanol (85:15 (v/v)) was added to the 1 g sample and then mixed for 15 sec. on a vortex before being placed on a rotormixer at 35 rpm for 5 min. Afterwards the sample was placed in a water bath at 97° C. for 10 minutes, followed by mixing on a rotormixer at 35 rpm for one hour. The sample was then centrifuged at 1370 g for ten minutes. The supernatant being the organic phase containing the extracted lipid was then transferred to new glass tube.

For HPTLC 1.5 mL of the extracted lipid was evaporated at 70° C. under nitrogen cover and then redispersed in 400 μL hexane:isopropanol (3:2 (v/v)). 3 μL redispersed extracted lipid was applied to the TLC plate, see below.

HPTLC Procedure:

HPTLC plates (20×10 cm, Merck no. 1.05641) were activated by drying (160° C., 20-30 minutes) and standard and samples were applied using an Automatic HPTLC Applicator (ATS4, CAMAG). Plate elution was performed using an Automatic Developing Chamber (ADC2, CAMAG) (7 cm). After elution, plates were dried (160° C., 10 minutes), cooled, and immersed (10 seconds) in developing fluid (6% cupric acetate in 16% $H_3PO_4$). After drying (160° C., 6 minutes) plates were evaluated visually using a TLC scanner (TLC Scanner 3, CAMAG).

Results:

Results from the first baking trial is represented in table 8 and FIG. 28.

TABLE 8

| First baking trial. Bread volume (ml/g) as a function of lipolytic enzymes (KLM1, Mut4, Mut5 and Mut9) and dose (TIPU/kg flour) | | | | |
|---|---|---|---|---|
| | Bread volume = f(Enzyme × dose) | | | |
| TIPU/kg flour | KLM1 | MUT4 | MUT5 | MUT9 |
| 0 | 6.6 | 6.6 | 6.6 | 6.6 |
| 225 | 6.56 | 7.9 | 7.84 | 7.55 |
| 450 | 7.66 | 7.54 | 7.79 | na. |
| 900 | 7.57 | 6.82 | 7.77 | na. |

FIG. 28 show the results of the first baking trial—showing bread volume (ml/g) as a function of lipolytic enzyme (KLM1, Mut4, Mut5 and Mut9) and dose (TIPU/kg flour).

As can be see from Table 8 and FIG. 28, all three lipolytic variants increased the bread volume at significantly lower enzyme dose than the wildtype (KLM1). Based on the results obtained in the first baking trial, a second baking trial was performed, dosing the lipolytic variant lower than the wild-type lipase (KLM1). Results from this experiment are represented in Table 9 and FIG. 29.

TABLE 9

| Second baking trial: Bread volume (ml/g) as a function of lipases (KLM1, Mut4, Mut5 and Mut9) and dose (TIPU/kg flour) | | | | |
|---|---|---|---|---|
| | Bread volume = f(Enzyme × dose) | | | |
| TIPU/kg flour | KLM1 | MUT4 | MUT5 | MUT9 |
| 0 | 7.05 | 7.05 | 7.05 | 7.05 |
| 56 | na | 7.94 | 6.95 | 7.06 |
| 112 | na | 8.05 | 7.57 | 8.28 |
| 225 | 7.32 | 8.32 | 7.94 | 8.53 |
| 450 | 8.46 | na | na | na |

FIG. 29 shows the results from the second baking trial, bread volume (ml/g) as a function of lipolytic enzyme (KLM1, Mut4, Mut5 and Mut9) and dose (TIPU/kg flour)

As can be seen from the second baking trial, the lipolytic enzyme variants facilitate the same bread volume as the wild-type lipolytic enzyme with much less activity dosed, indicating that their performance in breadmaking is superior to the wildtype lipolytic enzyme.

The above baking performance of the variant lipolytic enzyme and the wildtype (KLM1) correlated nicely to lipid modification demonstrated by the lipid analysis. All three variant lipolytic enzymes facilitated a significantly higher modification of the galactolipid fraction (di-galactosyl-di-glyceride (DGDG)) generating the resulting lyso component (di-galactosyl-mono-glyceride (DGMG)).

In addition to the above trials, a baking trial was also conducted using the same methods and materials for Mut 9, Mut345, Mut3459 and Mut 11 and FIG. 31 shows the results of this trial, namely the relative bread volume (%) of bread baked with different variants in different doses (mg/kg flour).

As can be seen from these data the baking performance of the variant lipolytic enzymes facilitate the same or better bread volume as the wild type lipolytic enzyme with much less activity dosed, indicating that their performance in bread making is superior to the wildtype lipolytic enzyme (KLM1).

Example 8

Homology Model of KLM1 Lipolytic Enzyme

A 3-D model showing the 3-D structure of the KLM1 lipolytic enzyme was prepared in order to identify sites for modification.

The amino acid sequence for the lipolytic enzyme (shown herein as SEQ. ID No. 2 (KLM1) was compared to all known enzyme structures in the Protein Data Bank (www.rcsb.org) and the known structure having the highest sequence homology was found to be the *Thermomyces lanuginosa* lipase entry 1DT3. The amino acid sequence of the KLM1 lipolytic enzyme shares only 40% sequence identity with the *Thermomyces* lipase over the 269 residues present in the protein data bank structure.

Using the Homology modelling features of the Computer program suite MOE© provided by Chemical Computing Group of Montreal, Quebec Canada, a model of the residues 33-296 of the KLM1 lipolytic enzyme was generated, using program defaults in the MOE program suite. The resulting model is compared with the basis structure of the *Thermomyces* lipase in FIG. 32. Overall there is very good agreement of the overall fold and the catalytic triad residues of the KLM1 lipolytic enzyme, S174, D228 and H287 superpose the *Thermomyces* lipase triad.

The catalytic triad for KLM1 is S174, D228 and H287.

FIG. 32 shows a stereoview comparing the homology model of residues 33-296 of the KLM1 lipolytic enzyme (dark lines) with the structure of the *Thermomyces* lipase (pdb entry 1DT3) in light lines. The two structure share a high conservation of secondary structure with the catalytic traid of the homology model found at the location relative to common features of secondary structure found in the *Thermomyces* lipase.

The positions of the three substitutions (namely at K63, G78 and A190) were located in the homology model.

K63N, G78N and A190N introduce glycosylation sites in loops that are distal to the catalytic triad. The locations of these sites relative to the catalytic triad are shown in FIG. 33. The substitution at position 63 is in a loop formed by a disulfide bond between C54 and C66. Position 78 is found in an adjacent loop between an expected helix ending at position 75 and a β strand of the central mixed β sheet beginning with residue 79. Position 190 is found in another loop extending from the residue 188 and the end of a helix and residue 195 which is the start of another β strand of the central mixed β sheet.

FIG. 33 shows a stereoview showing the relative location of the substitutions at positions 63, 78 and 190 (shown in space filing representation) relative to the catalytic triad shown in the stick representation. It can be seen that these position are found in Loops that are distal to the catalytic triad.

In addition to the loops having substitutions at positions 63, 78 and 190 several others loops can be identified in the model that share a similar juxtaposition relative the active site of the enzyme. Three of these loops are found between loops 75-79 and 188-195, these are formed by residues 99-103 occurring between two β strands of the central sheet, between C129-C135 forming another disulfide linked loop and 162-167 which occurs between the end of a helix and the beginning of another strand of the central helix. There is one other such loop again between the helix and a strand of the central helix residues 213-221. The location of these loops relative to the catalytic triad are shown in FIG. 34.

FIG. 34 shows a stereoview showing the location of distal loops in the KLM1 lipolytic enzyme based on the homology model. These loops incorporate the position of substitutions at positions 63, 78 and 190 shown in space filling representation and are distal to the catalytic triad shown as stick figures. These loops comprise residues 54-66, 75-79, 99-103, 127-135, 162-167, 188-195 and 213-221.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention is further described by the following numbered paragraphs:

1. A method for preparing a variant lipolytic enzyme comprising expressing in a host organism a nucleotide sequence which has at least 90% identity with a nucleotide sequence encoding a fungal lipolytic enzyme and comprises at least one modification at a position which corresponds in the encoded amino acid sequence to the introduction of at least one glycosylation site (or one additional glycosylation site) in the amino acid sequence compared with the original fungal lipolytic enzyme wherein each amino acid position corresponds to the position of the amino acid sequence when aligned with SEQ ID No. 2; wherein when the nucleotide sequence has at least 90% identity with a nucleotide sequence encoding the fungal lipolytic enzyme shown in SEQ ID No. 22 or SEQ ID No. 23 the modification is not a substitution at position 63 and the deletion is not at position 311-312; wherein the nucleotide sequence has at least 90% identity with SEQ ID No. 1, with SEQ ID No. 24, or with a nucleotide sequence shown in positions 23-106 of SEQ ID No. 24, or with a nucleotide sequence shown in positions 113-1063 of SEQ ID No. 24 or with a nucleotide sequence shown in positions 113-929 of SEQ ID No. 24.

2. A method according to paragraph 1 wherein the fungal lipolytic enzyme before modification does not comprise any glycosylation sites.

3. A method of producing a lipolytic enzyme comprising expressing in a host organism a nucleotide sequence comprising SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleotide sequence having at least 98% identity therewith; or a nucleic acid which is related to the nucleotide sequence of SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26 by the degeneration of the genetic code.

4. A method according to paragraph 1 or paragraph 2 wherein the modification corresponds with the introduction of at least one glycosylation site at a surface position on the polypeptide and at a location in an external loop distal to the active site of the enzyme.

5. A method according to any one of paragraphs 1-3 wherein the nucleotide sequence is modified such that one or more amino acids located at a surface position on the polypeptide and at a location in an external loop which is distal to the active site of the enzyme is substituted with an amino acid which is more hydrophilic than the original amino acid.

6. A method according to any one of the preceding paragraphs wherein the nucleotide sequence is modified such that one or more hydrophilic amino acids are inserted at a surface position on the polypeptide and at a location in the external loop distal to the active site of the enzyme.

7. A method according any one of the preceding paragraphs wherein the nucleotide sequence is modified such that in the encoded amino acid one or more amino acids are substituted or inserted to provide one or more consensus sequences Asn-Xxx-Ser or Asn-Xxx-Thr, where Xxx could be any amino acid except Pro.

8. A method according to any one of the preceding paragraphs wherein the nucleotide sequence is modified such that in the encoded amino acid sequence one or more Asn, Ser or Thr are introduced.

9. A method according to any one of the preceding paragraphs wherein at least two, preferably at least three, glycosylation sites are introduced.

10. A method according to any one of the preceding paragraphs wherein the nucleotide sequence is further modified to enhance C-terminal processing of the protein compared with SEQ ID No. 2.

11. A method according to paragraph 9 wherein the C-terminus is from amino acid position 306 onwards, wherein said position corresponds to the position in the amino acid sequence of SEQ ID No. 2 when aligned.

12. A method according to any one of paragraphs 9 or 10 wherein the C-terminal processing comprises one or more of the following: a substitution or insertion at positions 306 or 320 or a deletion at one or more KEX2 positions in the C-terminus, wherein each position corresponds to the position of the amino acid sequence of SEQ ID No. 2.

13. A method according to any one of paragraphs 9 to 11 wherein the C-terminal processing comprises one or more of the following: a substitution at positions 306 or 320 or a deletion at one or more positions 311-312 or 307-319, wherein each position corresponds to the position of the amino acid sequence of SEQ ID No. 2.

14. A method according to any one of the preceding paragraphs wherein nucleotide sequence is modified such that there is a substitution at one or more of positions 33, 63, 78, 190 and 305, wherein the amino acid is substituted with N, wherein said position corresponds to the position in the amino acid sequence of SEQ ID No. 2 when aligned.

15. The method according to any one of the preceding paragraphs wherein the nucleotide sequence is modified such that there is a substitution at position 306, wherein the amino acid is substituted with any amino acid other than K or R or A, preferably the substitution at position 306 is with amino acid S, wherein said position corresponds to the position in the amino acid sequence of SEQ ID No. 2 when aligned.

16. The method according to any one of the preceding paragraphs wherein the nucleotide sequence is modified such that there is a substitution at position 320, wherein the amino acid is substituted with any amino acid other than T, preferably the substitution at position 320 is with amino acid E, wherein said position corresponds to the position in the amino acid sequence of SEQ ID No. 2 when aligned.

17. A method according to any one of the preceding paragraphs wherein the host organism is a fungi, preferably from the genus *Trichoderma*, more preferably from the species *Trichoderma reesei.*

18. A polypeptide (prepro-polypeptide or lipolytic enzyme) obtained by the method according to any one of the preceding paragraphs.

19. A nucleic acid comprising a nucleotide sequence encoding a lipolytic enzyme and comprises at least one modification at a position which corresponds in the encoded amino acid sequence to the introduction of at least one glycosylation site in the amino acid sequence wherein each amino acid position corresponds to the position of the amino acid sequence of SEQ ID No. 2, wherein when the nucleotide sequence encodes the fungal lipolytic enzyme shown as SEQ ID No. 22 or SEQ ID No. 23 the modification is not a substitution at position 63 and the deletion is not at position 311-312; wherein the nucleotide sequence has at least 90% identity with SEQ ID No. 1, with SEQ ID No. 24, or with a nucleotide sequence shown in positions 23-106 of SEQ ID No. 24, or with a nucleotide sequence shown in positions 113-1063 of SEQ ID No. 24 or with a nucleotide sequence shown in positions 113-929 of SEQ ID No. 24.

20. A nucleic acid according to paragraph 19 wherein the fungal lipolytic enzyme before modification does not comprise any glycosylation sites.

21. A nucleic acid according to paragraph 19 or paragraph 20 wherein the nucleotide sequence comprises at least one modification corresponding with the substitution of one or more amino acids located at a surface position on the polypeptide and at a location in an external loop which is distal to the active site of the enzyme with an amino acid which is more hydrophilic than the original amino acid.

22. A nucleic acid according to any one of paragraphs 19 to 21 wherein the nucleotide sequence comprises at least one modification corresponding with the insertion of one or more hydrophilic amino acids at a surface position on the polypeptide and at a location in the external loop distal to the active site of the enzyme.

23. A nucleic acid according to any one of paragraphs 19 to 22 wherein the nucleotide sequence comprises at least one modification corresponding to the substitution or insertion of one or more amino acids to provide one or more consensus sequences Asn-Xxx-Ser or Asn-Xxx-Thr, where Xxx could be any amino acid except Pro in the encoded protein.

24. A nucleic acid according to any one of paragraphs 19 to 23 wherein the nucleotide sequence comprises a modification corresponding with the introduction of one or more Asn, Ser or Thr into the encoded protein.

25. A nucleic acid according to any one of paragraphs 19 to 24 comprising codons encoding for at least two, preferably at least three, glycosylation sites.

26. A nucleic acid according to any one of paragraphs 19 to 25 wherein the nucleotide sequence comprises a modification in the C-terminal region of the sequence to enhance C-terminal processing of the protein compared with SEQ ID No. 2.

27. A nucleic acid according to paragraph 26 wherein the C-terminus is comprises of the nucleotide sequence encoding amino acid position 306 onwards, wherein said position corresponds to the position in the amino acid sequence of SEQ ID No. 2 when aligned.

28. A nucleic acid according to any one of paragraphs 26 to 27 wherein the modification in the C-terminal region comprises one or more modifications that result in a substitution or insertion at positions 306 or 320 or a deletion at one or more KEX2 positions in the C-terminus of the encoded protein, wherein each position corresponds to the position of the amino acid sequence of SEQ ID No. 2.

29. A nucleic acid according to any one of paragraphs 26 to 28 wherein the modification comprises a modification that results in one or more of the following: a substitution at positions 306 or 320 or a deletion at one or more positions 311-312 or 307-319, wherein each position corresponds to the position of the amino acid sequence of SEQ ID No. 2.

30. A nucleic acid according to any one of paragraphs 19-29 wherein nucleotide sequence comprises a modification that results in a substitution at one or more of positions 63, 78, 190 and 305, wherein by the amino acid is substituted with N, in the encoded protein, wherein said position corresponds to the position in the amino acid sequence of SEQ ID No. 2 when aligned.

31. The nucleic acid according to any one of paragraphs 19 to 30 wherein nucleotide sequence comprises a modification that results in a substitution at position 306 in the encoded protein, wherein the substitution is with any amino acid other than K or R or A, preferably the substitution at position 306 is with amino acid S, wherein said position corresponds to the position in the amino acid sequence of SEQ ID No. 2 when aligned.

32. The nucleic acid according to any one of the paragraphs 19 to 31 wherein the nucleotide sequence wherein nucleotide sequence comprises a modification that results in a substitution at position 320, wherein the amino acid is substituted with any amino acid other than T, preferably the substitution at position 320 is with amino acid E, wherein said position corresponds to the position in the amino acid sequence of SEQ ID No. 2 when aligned.

33. A nucleotide sequence encoding a polypeptide having hydrolytic activity towards an ester bond in a polar lipid which nucleotide sequence comprises SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleotide sequence having at least 98% (preferably at least 99%, more preferably at least 99.5%, more preferably at least 99.8%) identity with SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26; or a nucleic acid which is related to the nucleotide sequence of SEQ ID No. 8, SEQ ID No. 6, SEQ ID No. 4, SEQ ID No. 10, SEQ ID No. 12, SEQ ID No. 14, SEQ ID No. 16, SEQ ID No. 18, SEQ ID No. 20 or SEQ ID No. 26 by the degeneration of the genetic code.

34. A variant polypeptide encoded by the nucleic acid or nucleotide sequence according to any one of paragraphs 19-33.

35. A variant polypeptide which has hydrolytic activity towards an ester bond in a polar lipid and comprises an amino acid sequence which has at least 90% identity with amino acids 33-296 of SEQ ID No. 2 and which has been modified compared with the sequence shown in SEQ ID No. 2 to introduce at least one glycosylation site in the amino acid sequence, wherein each amino acid position corresponds to the position of the amino acid sequence shown in SEQ ID No. 2.

36. A polypeptide according to paragraph 35 wherein one or more amino acids located at a surface position on the polypeptide and at a location in an external loop which is distal to the active site of the enzyme is substituted with an amino acid which is more hydrophilic than the original amino acid.

37. A polypeptide according to any one of paragraphs 35 or 36 wherein one or more hydrophilic amino acids are inserted at a surface position on the polypeptide and at a location in the external loop distal to the active site of the enzyme.

38. A polypeptide according any one of paragraphs 35 to 37 wherein one or more amino acids are substituted or inserted to provide one or more consensus sequences Asn-Xxx-Ser or Asn-Xxx-Thr, where Xxx could be any amino acid except Pro.

39. A polypeptide according to any one of paragraphs 35-38 wherein one or more Asn, Ser or Thr are introduced.

40. The polypeptide according to any one of paragraphs 35-39 wherein the modification at one or more of positions 33, 63, 78, 190 is substitution of the amino acid at that position with the amino acid N, wherein said position corresponds to the position in the amino acid sequence of SEQ ID No. 2 when aligned.

41. A polypeptide according to any one of paragraphs 35-40 wherein at least two, preferably at least three, glycosylation sites are introduced.

42. The polypeptide according to any one of paragraphs 18, 34-43 wherein the variant polypeptide has phospholipase activity or galactolipase activity.

43. The polypeptide according to any one of paragraphs 18, 34-43 wherein the polypeptide comprises amino acids 33-296 of the amino acid sequence shown as SEQ ID No. 2 except for the following modifications:

| |
|---|
| G33N |
| K63N; |
| G78N; |
| A190N; |
| K63N + G78N + A190N; |

44. A prepropolypeptide which when post-translationally processed in a host organism produces a polypeptide which has hydrolytic activity towards an ester bond in a polar lipid, wherein the prepropolypeptide comprises an amino acid sequence shown as SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25.

45. A polypeptide which has hydrolytic activity towards an ester bond in a polar lipid, which polypeptide is obtainable from the prepro-polypeptide comprising an amino acid sequence shown as SEQ ID No. 9, SEQ ID No. 7, SEQ ID No. 5, SEQ ID No. 11, SEQ ID No. 13, SEQ ID No. 15, SEQ ID No. 17, SEQ ID No. 19, SEQ ID No. 21 or SEQ ID No. 25.

46. Use of a nucleic acid according to any one of paragraphs 19-33 to enhance expression of a lipolytic enzyme from a host organism.

47. Use according to paragraph 46 wherein the host organism is a fungi, preferably *Trichoderma* spp., preferably *Trichoderma reesei.*

48. A method of making a foodstuff comprising adding a polypeptide according to any one of paragraphs 18 or 34-43 or 45 to one or more ingredients of the foodstuff.

49. A method of making a baked product comprising adding a polypeptide according to any one of paragraphs 18 or 34-43 or 45 to a dough and baking the dough to make the baked product.

50. A method according to paragraph 48 wherein the foodstuff is one or more of: egg or an egg-based product; a baked product; noodles; tortilla; a dough; confectionery; a frozen product; a dairy product including a cheese; a mousse; a whipped vegetable cream; an edible oil and fat; an aerated and non-aerated whipped product; an oil-in-water emulsions and water-in-oil emulsions; margarine; shortening; a spread, including low fat and very low fat spreads; a dressing; mayonnaise; a dip; a cream based sauce; a cream based soup; a beverage; a spice emulsion and a sauce.

51. A method of preparing a lyso-phospholipid comprising treating a phospholipid with a polypeptide according to any one of paragraphs 18 or 34-43 or 45 to produce the lyso-phospholipid.

52. A method of preparing a lyso-glycolipid comprising treating a glycolipid with a polypeptide according to any one of paragraphs 18 or 34-43 or 45 to produce a lyso-glycolipid.

53. A process of enzymatic degumming of vegetable or edible oils, comprising treating the edible or vegetable oil with a polypeptide according to any one of paragraphs 18 or 34-43 or 45 so as to hydrolyse a major part of the polar lipids present therein.

54. A foodstuff obtained by the method according to paragraph 48 or 50.

55. A baked product obtained by the method of paragraph 49.

56. A bread-improving composition or a dough-improving composition comprising a variant polypeptide according to any one of paragraphs 18 or 34-43 or 45.

57. A dough or baked product comprising a bread-improving or dough-improving composition according to paragraph 52.

58. A variant polypeptide as generally defined herein with reference to the Examples and Figures.

59. A method as generally defined herein with reference to the Examples and Figures.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for preparing a variant lipolytic enzyme with improved lipase activity as compared with the precursor wild-type KLM1enzyme having the amino acid sequence SEQ ID NO: 2 comprising expressing in a host organism a nucleotide sequence encoding a variant lipolytic enzyme the precursor amino acid sequence of which has at least 85% identity with the amino acid sequence of the precursor lipase amino acid sequence from position 31 through position 348 of SEQ ID No. 2 wherein the encoded precursor variant lipolytic enzyme is modified such that one or more amino acids located at a surface position within an external loop distal to the active site of the variant precursor lipolytic enzyme is substituted with an amino more hydrophilic than the original amino acid (i) at a position corresponding to any of positions 54-66 of SEQ ID No. 2, (ii) at a position corresponding to any of positions 75-79 of SEQ ID No. 2, (iii) at a position corresponding to any of positions 99-103 of SEQ ID No. 2, (iv) at a position corresponding to any of positions 127-135 of SEQ ID No. 2, (v) at a position corresponding to any of positions 162-167 of SEQ ID No. 2, (vi) at a position corresponding to any of positions 188-195 of SEQ ID No. 2, and/or (vii) at a position corresponding to any of positions 213-221 of SEQ ID No. 2;

wherein the modification is not a substitution at position 63.

2. The method according to claim 1, wherein the encoded variant lipolytic enzyme precursor amino acid sequence further comprises at least one modification which corresponds to (a) an introduction of at least one glycosylation site not present in the amino acid sequence of the original lipolytic enzyme wherein one or more amino acids are substituted or inserted to provide one or more consensus sequences Asn-Xxx-Ser or Asn-Xxx-Thr, where Xxx could be any amino acid except Pro; including a substitution of an asparagine replacing the amino acid at one or more amino acid positions corresponding to positions 33, 63, 78, 190 and 305 in the amino acid sequence of SEQ ID No. 2; or (b) a substitution replacing the amino acid at a position corresponding to position 306 of SEQ ID No. 2 with any amino acid other than lysine, arqinine or alanine; or (c) a substitution replacing the amino acid at a position corresponding to position 320 of SEQ ID No. 2 with any amino acid other than threonine; or (d) where the host organism is a fungi and C-terminal processing of the encoded mature variant lipolytic enzyme occurs at a position corresponding to position 306 of SEQ ID No. 2, or at an amino acid position carboxyl-proximal thereto, the encoding nucleotide sequence is further modified to enhance the C-terminal processing of the variant lipolytic enzyme by the fungal host organism compared to C-terminal processing of the wild type KLM1enzyme of SEQ ID No: 2 by introducing (i) an amino acid insertion at a position in the amino acid sequence of the variant precursor lipolytic enzyme corresponding to position 306 and/or position 320 of the amino acid sequence of SEQ ID No. 2, or (ii) an amino acid deletion within one or more KEX2 sites at a position corresponding to position 306 of SEQ ID No.2 or at an amino acid position carboxyl-proximal thereto, or (iii) a deletion of amino acids at positions corresponding to positions 311-312 or positions 307-319 of the amino acid sequence of SEQ ID No. 2, thereby increasing the lipase activity and/or expression of the encoded variant lipolytic enzyme by comparison with the lipase activity and expression of the wild type KLM1 enzyme of SEQ ID No: 2.

3. The method according to claim 2 wherein at least two glycosylation sites are introduced.

4. The method according to claim 3 wherein at least three glycosylation sites are introduced.

5. A nucleic acid comprising a nucleotide sequence encoding a variant lipolytic enzyme the mature amino acid sequence of which has at least 85% identity with the amino acid sequence of the mature lipase amino acid sequence from position 31 through position 348 of SEQ ID No. 2 and having improved lipase activity compared with the wild-type KLM1 enzyme wherein the nucleic acid sequence is modified to encoded precursor lipolytic enzyme is modified such that one or more amino acids located at a surface position within an external loop distal to the active site of the enzyme is substituted with an amino more hydrophilic than the original amino acid (i) at a position corresponding to any of positions 54-66 of SEQ ID No. 2, (ii) at a position corresponding to any of positions 75-79 of SEQ ID No. 2, (iii) at a position corresponding to any of positions 99-103 of SEQ ID No. 2, (iv) at a position corresponding to any of positions 127-135 of SEQ ID No. 2, (v) at a position corresponding to any of positions 162-167 of SEQ ID No. 2, (vi) at a position corresponding to any of positions 188-195 of SEQ ID No. 2, and/or (vii) at a position corresponding to any of positions 213-221 of SEQ ID No. 2;

wherein the modification is not a substitution at position 63.

6. The nucleic acid according to claim 5, encoding a variant lipolytic enzyme further comprising (a) an introduction of at least one glycosylation site not present in the amino acid sequence of the original lipolytic enzyme wherein one or more amino acids are substituted or inserted to provide one or more consensus sequences Asn-Xxx-Ser or Asn-Xxx-Thr, where Xxx could be any amino acid except Pro, in the encoded variant lipolytic enzyme, including a substitution of an asparaqine replacing the amino acid at one or more amino acid positions corresponding to positions 33, 63, 78, 190 and 305 in the amino acid sequence of SEQ ID No. 2, or (b) a substitution replacing the amino acid at a position corresponding to position 306 of SEQ ID No. 2 with any amino acid other than lysine, arqinine or alanine; or (c) a substitution replacing the amino acid at a position corresponding to position 320 of SEQ ID No. 2 with any amino acid other than threonine; or (d) where C-terminal processing of the encoded mature variant precursor lipolytic enzyme occurs at a position corresponding to position 306 of SEQ ID No.2, or at an amino acid position carboxyl-proximal thereto, the encoding nucleotide sequence is further modified to enhance the C-terminal processing of the variant precursor lipolytic enzyme compared to C-terminal processing of the wild type KLM1 enzyme of SEQ ID No: 2 by introducing one or more of (i) an amino acid insertion at a position in the amino acid sequence of the variant precursor lipolytic enzyme corresponding to position 306 and/or position 320 of the amino acid sequence of SEQ ID No. 2, (ii) an amino acid deletion within one or more KEX2 sites at a position corresponding to position 306 of SEQ ID No.2 or at an amino acid position carboxyl-proximal thereto, and (iii) a deletion of amino acids at positions corresponding to positions 311-312 or positions 307-319 of the amino acid sequence of SEQ ID No. 2, thereby increasing the lipase activity and/or expression of the encoded variant lipolytic enzyme by comparison with the lipase activity and expression of the wild type KLM1 enzyme of SEQ ID No: 2.

7. The nucleic acid according to claim 6 wherein at least two qlycosylation sites are introduced.

8. The nucleic acid according to claim 7 wherein at least three qlycosylation sites are introduced.

9. The nucleic acid according to claim 6 wherein the nucleotide sequence comprises a modification that results in the substitution of a serine replacing the amino acid at the position corresponding to position 306 of SEQ ID No. 2.

10. The nucleic acid according to claim 6 wherein the nucleotide sequence comprises a modification that results in the substitution of a glutamic acid replacing the amino acid at the position corresponding to position 320 of SEQ ID No. 2.

11. A method of expression of a variant lipolytic enzyme encoded by the nucleic acid or nucleotide sequence according to claim 5 or 6 comprising transforming a eukaryotic host organism with said nucleic acid or nucleotide sequence and cultivating the transformed host cell under conditions where the nucleic acid is expressed and harvesting the lipolytic enzyme, wherein secretion is enhanced as compared with secretion of the wild-type KLM1 enzyme having the amino acid sequence SEQ ID No. 2.

12. The method according to claim 11 wherein the host organism is a fungi.

13. The method according to claim 11 wherein at least three glycosylation sites are introduced.

14. A method according to claim 2 or 12 wherein the fungi is a *Trichoderma spp.*

15. The method according to claim 14 wherein the *Trichoderma spp.* is *Trichoderma reesei.*

16. A variant precursor lipolytic enzyme with improved expression and/or lipase activity compared with the wild-type KLM1 enzyme of SEQ ID No. 2 obtained by the method according to claim 2.

17. A variant lipolytic enzyme encoded by the nucleic acid or nucleotide sequence according to claim 5 or 6 having improved expression and/or lipase activity compared with the wild type KLM1 enzyme having the amino acid sequence SEQ ID No. 2.

* * * * *